US012653558B2

(12) United States Patent
Childs et al.

(10) Patent No.: US 12,653,558 B2
(45) Date of Patent: Jun. 16, 2026

(54) METHODS FOR CLOT REMOVAL

(71) Applicant: Inquis Medical, Inc., Menlo Park, CA (US)

(72) Inventors: Richard Childs, Santa Rosa, CA (US); Richard Christian Ewers, Fullerton, CA (US); William Jason Fox, San Mateo, CA (US); Vahid Saadat, Atherton, CA (US)

(73) Assignee: Inquis Medical, Inc., Menlo Park, CA (US)

( * ) Notice: Subject to any disclaimer, the term of this patent is extended or adjusted under 35 U.S.C. 154(b) by 0 days.

(21) Appl. No.: 19/192,303

(22) Filed: Apr. 28, 2025

(65) Prior Publication Data

US 2025/0255626 A1     Aug. 14, 2025

Related U.S. Application Data

(63) Continuation of application No. 18/859,162, filed as application No. PCT/US2023/066140 on Apr. 24, 2023, now Pat. No. 12,502,186.

(Continued)

(51) Int. Cl.
A61B 17/22 (2006.01)
A61B 17/00 (2006.01)

(52) U.S. Cl.
CPC ........ A61B 17/22 (2013.01); A61B 17/00234 (2013.01); A61B 2017/00238 (2013.01);
(Continued)

(58) Field of Classification Search
CPC .............. A61B 17/22; A61B 17/00234; A61B 2017/00238; A61B 2017/00305;
(Continued)

(56) References Cited

U.S. PATENT DOCUMENTS 4,368,730 A     1/1983     Sharrock
4,733,669 A     3/1988     Segal
(Continued)

FOREIGN PATENT DOCUMENTS

CN     103932756 A     7/2014
DE     212015000300 U1     9/2017
(Continued)

OTHER PUBLICATIONS

Patil et al; Characterising acute ischaemic stroke thrombi: insights from histology, imaging and emerging impedance-based technologies; Stroke and Vencular Neurology; 7(4); pp. 353-363; Aug. 2022.
(Continued)

*Primary Examiner* — Sarah Al Hashimi
*Assistant Examiner* — Nhu Q. Tran
(74) *Attorney, Agent, or Firm* — Shay Glenn LLP

(57) ABSTRACT

Aspiration catheters for removing clot material from a patient, systems including these catheter as well as methods of making and using these aspiration catheters may be configured to remove clot material in long, continuous strips that prevent release of smaller clot fragments back into the vessel. Also described herein are blood collection apparatuses that may allow safe and easy reperfusion of collected blood.

22 Claims, 26 Drawing Sheets

Related U.S. Application Data

(60) Provisional application No. 63/334,075, filed on Apr. 22, 2022.

(52) U.S. Cl.
CPC .............. *A61B 2017/00305* (2013.01); *A61B 2017/22079* (2013.01); *A61B 2217/005* (2013.01)

(58) Field of Classification Search
CPC .... A61B 2017/22079; A61B 2217/005; A61B 2218/001; A61B 2218/007; A61M 1/3601; A61M 1/3621
See application file for complete search history.

(56) References Cited

U.S. PATENT DOCUMENTS

| | | | |
|---|---|---|---|
| 4,828,543 A | 5/1989 | Weiss et al. | |
| 4,967,753 A | 11/1990 | Haase et al. | |
| 4,976,682 A | 12/1990 | Lane et al. | |
| 5,248,297 A | 9/1993 | Takase et al. | |
| 5,417,703 A | 5/1995 | Brown et al. | |
| 5,569,275 A | 10/1996 | Kotula et al. | |
| 5,603,703 A | 2/1997 | Elsberry et al. | |
| 5,662,671 A | 9/1997 | Barbut et al. | |
| 5,730,752 A | 3/1998 | Alden et al. | |
| 5,749,914 A | 5/1998 | Janssen | |
| 5,772,402 A | 6/1998 | Goodman | |
| 5,827,229 A | 10/1998 | Auth et al. | |
| 5,954,737 A | 9/1999 | Lee | |
| 6,027,450 A | 2/2000 | Brown et al. | |
| 6,059,745 A | 5/2000 | Gelbfish | |
| 6,089,235 A | 7/2000 | Hastings et al. | |
| 6,152,882 A | 11/2000 | Prutchi | |
| 6,428,551 B1 | 8/2002 | Hall et al. | |
| 6,589,227 B2 | 7/2003 | Klint | |
| 6,638,293 B1 | 10/2003 | Makower et al. | |
| 6,719,717 B1 | 4/2004 | Johnson et al. | |
| 6,719,718 B2 | 4/2004 | Bonnette et al. | |
| 6,849,068 B1 | 2/2005 | Bagaoisan et al. | |
| 6,979,318 B1 | 12/2005 | McDonald et al. | |
| 7,294,117 B2 | 11/2007 | Provost-tine et al. | |
| 7,608,063 B2 | 10/2009 | Le et al. | |
| 7,655,016 B2 | 2/2010 | Demarais et al. | |
| 7,699,790 B2 | 4/2010 | Simpson | |
| 7,713,235 B2 | 5/2010 | Torrance et al. | |
| 7,734,332 B2 | 6/2010 | Sher | |
| 7,771,445 B2 | 8/2010 | Heitzmann et al. | |
| 7,854,740 B2 | 12/2010 | Carney | |
| 7,927,346 B2 | 4/2011 | VanCamp et al. | |
| 7,938,820 B2 | 5/2011 | Webster et al. | |
| 7,942,852 B2 | 5/2011 | Mas et al. | |
| 7,947,012 B2 | 5/2011 | Spurchise et al. | |
| 8,048,032 B2 | 11/2011 | Root et al. | |
| 8,133,214 B2 | 3/2012 | Hayase et al. | |
| 8,150,499 B2 | 4/2012 | Gelbart et al. | |
| 8,208,990 B2 | 6/2012 | Maschke | |
| 8,246,640 B2 | 8/2012 | Rosenthal et al. | |
| 8,252,020 B2 | 8/2012 | Hauser et al. | |
| 8,265,745 B2 | 9/2012 | Hauck et al. | |
| 8,273,023 B2 | 9/2012 | Razavi | |
| 8,298,252 B2 | 10/2012 | Krolik et al. | |
| 8,343,084 B2 | 1/2013 | Nowakowski et al. | |
| 8,366,615 B2 | 2/2013 | Razavi | |
| 8,409,237 B2 | 4/2013 | Galdonik et al. | |
| 8,430,837 B2 | 4/2013 | Jenson et al. | |
| 8,465,452 B2 | 6/2013 | Kassab | |
| 8,496,653 B2 | 7/2013 | Steinke | |
| 8,613,717 B2 | 12/2013 | Aklog et al. | |
| 8,771,289 B2 | 7/2014 | Mohiuddin et al. | |
| 8,814,890 B2 | 8/2014 | Miyata et al. | |
| 8,920,402 B2 | 12/2014 | Nash et al. | |
| 8,920,448 B2 | 12/2014 | To et al. | |
| 9,050,126 B2 | 6/2015 | Rivers et al. | |
| 9,055,964 B2 | 6/2015 | Cartier et al. | |
| 9,060,895 B2 | 6/2015 | Hartley et al. | |
| 9,084,857 B2 | 7/2015 | Cully et al. | |
| 9,248,221 B2 | 2/2016 | Look et al. | |
| 9,254,140 B2 | 2/2016 | Song et al. | |
| 9,259,290 B2 | 2/2016 | Jenkins et al. | |
| 9,282,992 B2 | 3/2016 | Levine et al. | |
| 9,402,938 B2 | 8/2016 | Aklog et al. | |
| 9,415,188 B2 | 8/2016 | He et al. | |
| 9,433,427 B2 | 9/2016 | Look et al. | |
| 9,492,226 B2 | 11/2016 | Fish et al. | |
| 9,510,854 B2 | 12/2016 | Mallaby | |
| 9,655,633 B2 | 5/2017 | Leynov et al. | |
| 9,668,767 B2 | 6/2017 | To et al. | |
| 9,700,216 B2 | 7/2017 | Razavi et al. | |
| 9,801,527 B2 | 10/2017 | Ferren et al. | |
| 9,801,642 B2 | 10/2017 | Thor et al. | |
| 9,808,266 B2 | 11/2017 | Ray et al. | |
| 9,883,877 B2 | 2/2018 | Look et al. | |
| 10,130,386 B2 | 11/2018 | Simpson et al. | |
| 10,226,263 B2 | 3/2019 | Look et al. | |
| 10,226,268 B2 | 3/2019 | Ulm | |
| 10,238,456 B2 | 3/2019 | Murphy et al. | |
| 10,271,873 B2 | 4/2019 | Steingisser et al. | |
| 10,285,720 B2 | 5/2019 | Gilvarry et al. | |
| 10,383,983 B2 | 8/2019 | Aklog et al. | |
| 10,413,317 B2 | 9/2019 | Whiseant | |
| 10,517,617 B2 | 12/2019 | Aklog et al. | |
| 10,661,053 B2 | 5/2020 | Yang et al. | |
| 10,716,586 B2 | 7/2020 | Krolik et al. | |
| 10,722,238 B2 | 7/2020 | Sutton et al. | |
| 10,743,907 B2 | 8/2020 | Bruzzi et al. | |
| 10,751,159 B2 | 8/2020 | Janardhan et al. | |
| 10,835,257 B2 | 11/2020 | Ferrera et al. | |
| 10,888,337 B2 | 1/2021 | Shen et al. | |
| 10,912,482 B2 | 2/2021 | Bozsak et al. | |
| 10,945,758 B1 | 3/2021 | Davis et al. | |
| 11,013,523 B2 | 5/2021 | Arad Hadar | |
| 11,089,947 B2 | 8/2021 | Govari | |
| 11,096,712 B2 | 8/2021 | Teigen et al. | |
| 11,197,683 B1 | 12/2021 | Teigen et al. | |
| 11,253,277 B2 | 2/2022 | Buck et al. | |
| 11,259,821 B2 | 3/2022 | Buck et al. | |
| 11,376,028 B1 | 7/2022 | Saadat et al. | |
| 11,383,064 B2 | 7/2022 | Garrison et al. | |
| 11,395,665 B2 | 7/2022 | Yang et al. | |
| 11,400,255 B1 | 8/2022 | Chou et al. | |
| 11,464,528 B2 | 10/2022 | Brady et al. | |
| 11,510,577 B2 | 11/2022 | Bozsak et al. | |
| 11,568,990 B2 | 1/2023 | Lebedev et al. | |
| 11,730,924 B2 | 8/2023 | Saadat et al. | |
| 11,730,925 B2 | 8/2023 | Saadat et al. | |
| 11,779,238 B2 | 10/2023 | Sweeney et al. | |
| 11,849,963 B2 | 12/2023 | Quick | |
| 11,969,332 B2 | 4/2024 | Merritt et al. | |
| 12,053,192 B2 | 8/2024 | Baron et al. | |
| 12,076,036 B2 | 9/2024 | Baron et al. | |
| 12,246,141 B2 | 3/2025 | Saadat et al. | |
| 12,274,834 B2 | 4/2025 | Saadat et al. | |
| 2001/0049486 A1 | 12/2001 | Evans et al. | |
| 2002/0165575 A1 | 11/2002 | Saleh | |
| 2002/0177800 A1 | 11/2002 | Bagaoisan et al. | |
| 2003/0069549 A1 | 4/2003 | MacMahon et al. | |
| 2003/0191493 A1 | 10/2003 | Epstein et al. | |
| 2004/0019310 A1* | 1/2004 | Hogendijk .......... A61M 1/3621 604/1 |
| 2004/0049225 A1 | 3/2004 | Denison | |
| 2006/0004325 A1 | 1/2006 | Hamatake et al. | |
| 2006/0122575 A1 | 6/2006 | Wakabayashi | |
| 2006/0264988 A1 | 11/2006 | Boyle | |
| 2007/0060944 A1 | 3/2007 | Boldenow et al. | |
| 2007/0083195 A1 | 4/2007 | Werneth et al. | |
| 2007/0106211 A1 | 5/2007 | Provost-Tine et al. | |
| 2007/0129679 A1 | 6/2007 | Bonnette et al. | |
| 2007/0191812 A1 | 8/2007 | Nishide et al. | |
| 2008/0161840 A1 | 7/2008 | Osiroff et al. | |
| 2008/0228231 A1 | 9/2008 | Raphael et al. | |
| 2008/0243153 A1 | 10/2008 | Nguyen et al. | |
| 2009/0069828 A1 | 3/2009 | Martin et al. | |

(56) References Cited

U.S. PATENT DOCUMENTS

| | | |
|---|---|---|
| 2009/0177069 A1 | 7/2009 | Razavi |
| 2009/0221957 A1 | 9/2009 | Bowman et al. |
| 2010/0023033 A1 | 1/2010 | Mauch et al. |
| 2010/0041984 A1 | 2/2010 | Shapland et al. |
| 2010/0185048 A1 | 7/2010 | Lonky et al. |
| 2010/0204712 A1 | 8/2010 | Mallaby |
| 2010/0286708 A1 | 11/2010 | Rittman |
| 2011/0130714 A1 | 6/2011 | Wells |
| 2011/0137399 A1 | 6/2011 | Chomas et al. |
| 2011/0160740 A1 | 6/2011 | Makower et al. |
| 2011/0230799 A1 | 9/2011 | Christian et al. |
| 2012/0041474 A1 | 2/2012 | Eckhouse et al. |
| 2012/0071838 A1 | 3/2012 | Fojtik |
| 2013/0158578 A1 | 6/2013 | Ghodke et al. |
| 2013/0178790 A1 | 7/2013 | Tekulve |
| 2013/0268048 A1 | 10/2013 | Watson et al. |
| 2013/0317589 A1 | 11/2013 | Martin et al. |
| 2014/0046244 A1 | 2/2014 | Ray et al. |
| 2014/0051968 A1 | 2/2014 | Isham et al. |
| 2014/0058294 A1 | 2/2014 | Gross et al. |
| 2014/0094741 A1 | 4/2014 | Bellisario et al. |
| 2014/0217030 A1 | 8/2014 | Meyer et al. |
| 2014/0222049 A1 | 8/2014 | Fruland et al. |
| 2014/0303658 A1 | 10/2014 | Bonnette et al. |
| 2015/0005781 A1 | 1/2015 | Lund-Clausen et al. |
| 2015/0011856 A1 | 1/2015 | Arevalos |
| 2015/0250982 A1 | 9/2015 | Osypka |
| 2015/0305765 A1 | 10/2015 | Fojtik et al. |
| 2015/0327875 A1 | 11/2015 | Look et al. |
| 2015/0374405 A1 | 12/2015 | Takuma |
| 2016/0000499 A1 | 1/2016 | Lennox et al. |
| 2016/0067464 A1 | 3/2016 | Kim et al. |
| 2016/0089227 A1 | 3/2016 | Loh |
| 2016/0113676 A1 | 4/2016 | Tada et al. |
| 2016/0166265 A1 | 6/2016 | Nita |
| 2016/0166266 A1 | 6/2016 | Nita |
| 2016/0184562 A1 | 6/2016 | Ludin et al. |
| 2016/0220298 A1 | 8/2016 | Paul et al. |
| 2016/0278856 A1 | 9/2016 | Panescu et al. |
| 2016/0310020 A1 | 10/2016 | Warnking et al. |
| 2016/0346037 A1 | 12/2016 | Truckai et al. |
| 2016/0354100 A1 | 12/2016 | Darian |
| 2017/0035445 A1 | 2/2017 | Nguyen et al. |
| 2017/0043137 A1 | 2/2017 | Felkins et al. |
| 2017/0056581 A1 | 3/2017 | Deak et al. |
| 2017/0065396 A1 | 3/2017 | Look et al. |
| 2017/0224283 A1 | 8/2017 | Kassab et al. |
| 2017/0258512 A1 | 9/2017 | Germain et al. |
| 2017/0290598 A1 | 10/2017 | Culbert et al. |
| 2018/0042623 A1 | 2/2018 | Batiste |
| 2018/0206865 A1 | 7/2018 | Martin et al. |
| 2018/0235644 A1 | 8/2018 | Jaffe et al. |
| 2018/0344248 A1 | 12/2018 | Zeng et al. |
| 2018/0353194 A1 | 12/2018 | Shaffer et al. |
| 2018/0360479 A1 | 12/2018 | Hofmann et al. |
| 2019/0142453 A1 | 5/2019 | Efremkin |
| 2019/0167287 A1 | 6/2019 | Vale et al. |
| 2019/0175210 A1 | 6/2019 | Wittens |
| 2019/0192175 A1 | 6/2019 | Chida et al. |
| 2019/0262031 A1 | 8/2019 | Efremkin |
| 2019/0269538 A1 | 9/2019 | Chou et al. |
| 2019/0298396 A1 | 10/2019 | Gamba et al. |
| 2019/0313941 A1 | 10/2019 | Radjabl |
| 2019/0358387 A1 | 11/2019 | Elbrady et al. |
| 2019/0365469 A1 | 12/2019 | Efremkin |
| 2019/0380651 A1 | 12/2019 | Carreel et al. |
| 2019/0388002 A1 | 12/2019 | Bozsak et al. |
| 2020/0054432 A1 | 2/2020 | Martin |
| 2020/0100839 A1 | 4/2020 | Efremkin |
| 2020/0129202 A1 | 4/2020 | Schoenle et al. |
| 2020/0129741 A1 | 4/2020 | Kawwas et al. |
| 2020/0164117 A1 | 5/2020 | Culhane et al. |
| 2020/0170666 A1 | 6/2020 | Trosper et al. |
| 2020/0188016 A1 | 6/2020 | Miller et al. |
| 2020/0205738 A1 | 7/2020 | Adawi et al. |
| 2020/0246029 A1 | 8/2020 | Singleton et al. |
| 2020/0253670 A1 | 8/2020 | Doisneau et al. |
| 2020/0261112 A1 | 8/2020 | Jamous et al. |
| 2020/0281612 A1 | 9/2020 | Kelly et al. |
| 2020/0281648 A1 | 9/2020 | Schultheis et al. |
| 2020/0297362 A1 | 9/2020 | Deville et al. |
| 2020/0305900 A1 | 10/2020 | Vale et al. |
| 2020/0323546 A1 | 10/2020 | Skujins et al. |
| 2021/0007760 A1 | 1/2021 | Reisin |
| 2021/0068852 A1 | 3/2021 | Spence |
| 2021/0161544 A1 | 6/2021 | Casey |
| 2021/0161545 A1 | 6/2021 | Bhogal et al. |
| 2021/0220528 A1 | 7/2021 | Jalgaonkar et al. |
| 2021/0236257 A1 | 8/2021 | Walzman |
| 2021/0267613 A1 | 9/2021 | Follmer et al. |
| 2021/0316127 A1 | 10/2021 | Buck et al. |
| 2021/0353314 A1 | 11/2021 | Porter |
| 2021/0361305 A1 | 11/2021 | Mogi et al. |
| 2022/0001141 A1 | 1/2022 | Yourgenlow et al. |
| 2022/0211429 A1 | 7/2022 | Taff et al. |
| 2022/0226555 A1 | 7/2022 | Sunenshine et al. |
| 2022/0233264 A1 | 7/2022 | Klem et al. |
| 2022/0280171 A1 | 9/2022 | Teigen et al. |
| 2022/0338887 A1 | 10/2022 | Nair et al. |
| 2022/0339339 A1* | 10/2022 | Nair ...................... A61M 1/74 |
| 2022/0361901 A1 | 11/2022 | De Leon et al. |
| 2022/0379084 A1 | 12/2022 | Look et al. |
| 2022/0409857 A1* | 12/2022 | Saadat .......... A61B 17/320783 |
| 2023/0310751 A1 | 10/2023 | Merritt et al. |
| 2023/0310804 A1 | 10/2023 | Saadat et al. |
| 2023/0355125 A1 | 11/2023 | Wang et al. |
| 2023/0364319 A1 | 11/2023 | Vale et al. |
| 2024/0016505 A1 | 1/2024 | Horowitz et al. |
| 2024/0197347 A1 | 6/2024 | Saadat et al. |
| 2024/0245414 A1 | 7/2024 | Calderon et al. |
| 2024/0299048 A1 | 9/2024 | Saadat et al. |
| 2024/0307659 A1 | 9/2024 | Saadat et al. |
| 2025/0058084 A1 | 2/2025 | Saadat et al. |
| 2025/0099116 A1 | 3/2025 | Saadat et al. |
| 2025/0107813 A1 | 4/2025 | Childs et al. |
| 2025/0204934 A1* | 6/2025 | Thio ................. A61B 17/3207 |
| 2025/0339160 A1 | 11/2025 | Fox et al. |
| 2025/0339161 A1 | 11/2025 | Nauleau et al. |
| 2025/0339599 A1 | 11/2025 | Pare et al. |

FOREIGN PATENT DOCUMENTS

| | | |
|---|---|---|
| EP | 1292244 B1 | 1/2007 |
| EP | 2138200 A1 | 12/2009 |
| EP | 2782514 B1 | 12/2016 |
| EP | 2787893 B1 | 2/2017 |
| EP | 3244813 A1 | 11/2017 |
| EP | 3311875 A1 | 4/2018 |
| EP | 2231256 B1 | 5/2018 |
| EP | 1617893 B1 | 6/2018 |
| EP | 2299916 B1 | 8/2018 |
| EP | 2309934 B1 | 11/2018 |
| EP | 3705067 A2 | 9/2020 |
| EP | 3787523 A1 | 3/2021 |
| EP | 2908901 B1 | 5/2021 |
| EP | 4119069 A1 | 1/2023 |
| FR | 2903292 A1 | 1/2008 |
| JP | 2019187457 A | 10/2019 |
| JP | 2022062169 A | 4/2022 |
| JP | 2023022170 A | 2/2023 |
| KR | 20160026345 A | 3/2016 |
| WO | WO98/38929 A1 | 9/1998 |
| WO | WO2014/147815 A1 | 9/2014 |
| WO | WO2015/003134 A1 | 1/2015 |
| WO | WO2017/072663 A1 | 5/2017 |
| WO | WO2017/154748 A1 | 9/2017 |
| WO | WO2017/161204 A1 | 9/2017 |
| WO | WO2019/070782 A1 | 4/2019 |
| WO | WO2020/160179 A1 | 8/2020 |
| WO | WO2021/016213 A1 | 1/2021 |
| WO | WO2021/180826 A1 | 9/2021 |
| WO | WO2021/263033 A1 | 12/2021 |
| WO | WO2022/157270 A1 | 7/2022 |
| WO | WO2022/221643 A1 | 10/2022 |

(56)                    References Cited

FOREIGN PATENT DOCUMENTS

WO      WO2022/261448 A1     12/2022
WO      WO2023/278495 A2     1/2023
WO      WO2023/020961 A1     2/2023
WO      WO2024/092054 A2     5/2024

OTHER PUBLICATIONS

PCR Online; First-in-human data for sensome clot-sensing guidewire used in ischemic stroke treatment demonstrate ability to automate clot characterization with no safety issues; 4 pages; retrieved from the internet (https://www.pcronline.com/News/Press-releases/2024/First-in-human-data-for-Sensome-clot-sensing-guidewire-used-in-ischemic-stroke-treatment-demonstrate-ability-to-automate-clot-characterization-with-no-safety-issues?utm_source=chatgpt.com) on Feb. 18, 2025.

PCR Online; Sensome announces data from two new studies showing clot-sensing guidewire successfully identifies fresh clot to support decision-making in peripheral artery disease treatment; 4 pages; retrieved from the internet (https://www.pcronline.com/News/Press-releases/2024/Sensome-announces-data-from-two-new-studies-showing-clot-sensing-guidewire-successfully-identifies-fresh-clot-to-support-decision-making-in-peripheral-artery-disease-treatment?utm_source=chatgpt.com) on Feb. 18, 2025.

Rice et al.; CLOTILD a smart guidewire sensing clot characteristics during the mechanical thrombectomy procedure—results from the Clot Out study; 1 page; retrieved from the internet (https://www.sensome.com/_files/ugd/9575e7_0370965f17994ee193753e4b4df10e1a.pdf) on Feb. 18, 2025.

Santilli et al.; Superficial femoral popliteal vein: an anatomic study; Journal of vascular surgery; 31(3); pp. 450-455; Mar. 1, 2000.

Saadat et al.; U.S. Appl. No. 19/253,642 entitled "Apparatuses and methods for tracking obstructive material within a suction catheter," filed Jun. 27, 2025.

* cited by examiner

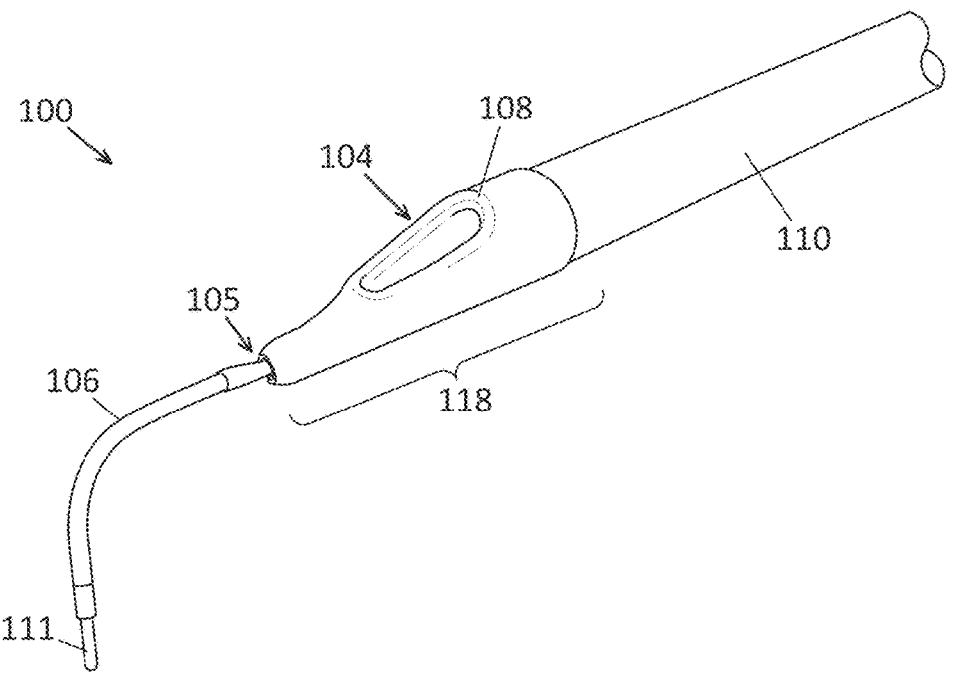
FIG. 1
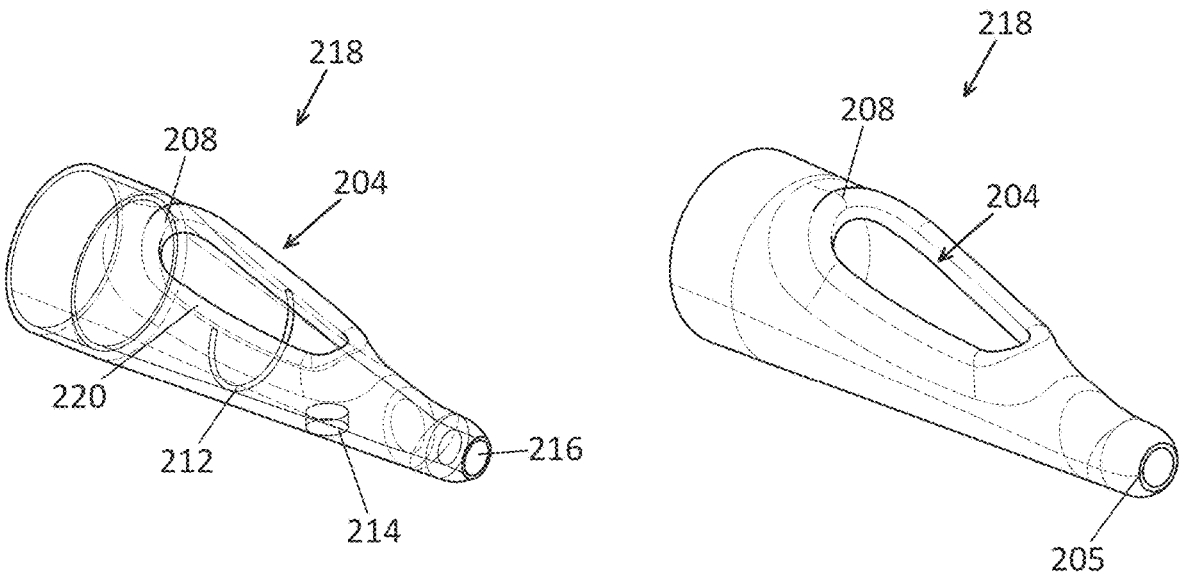
FIG. 2A                          FIG. 2B

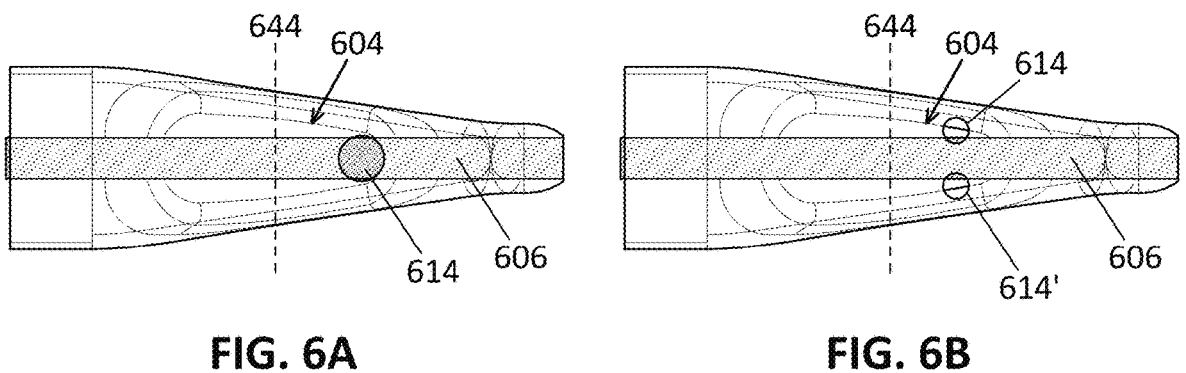
FIG. 6A                    FIG. 6B
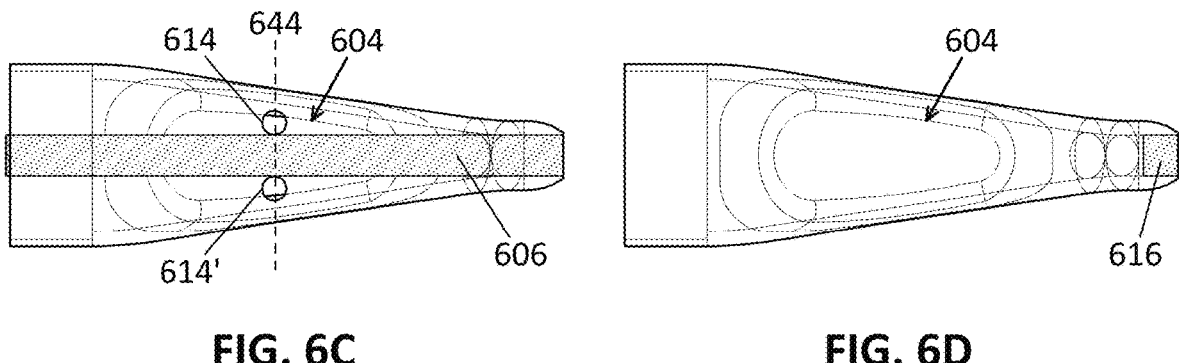
FIG. 6C                    FIG. 6D
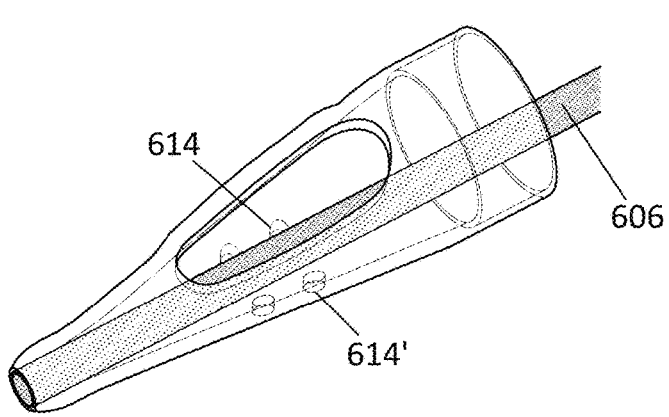
FIG. 6E

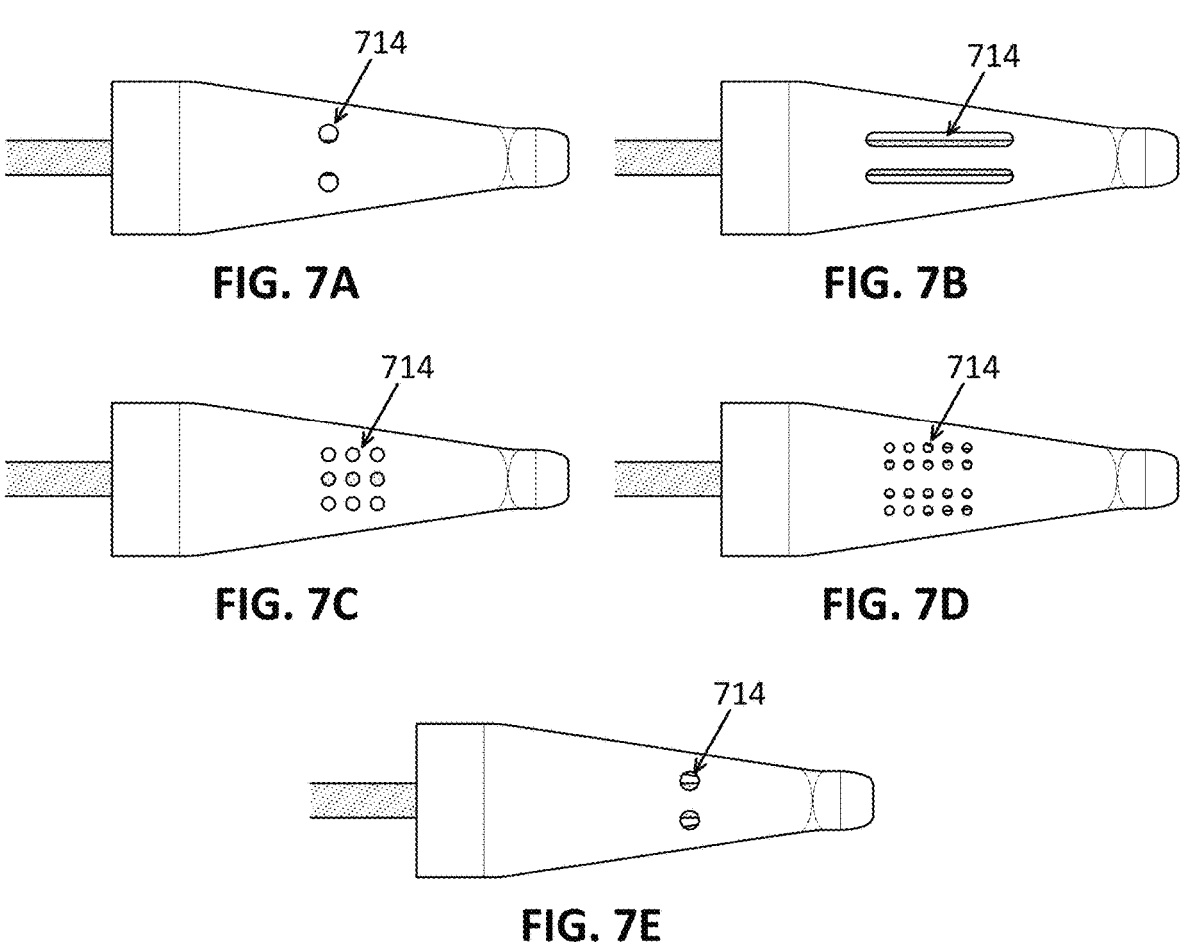
FIG. 7A
FIG. 7B
FIG. 7C
FIG. 7D
FIG. 7E
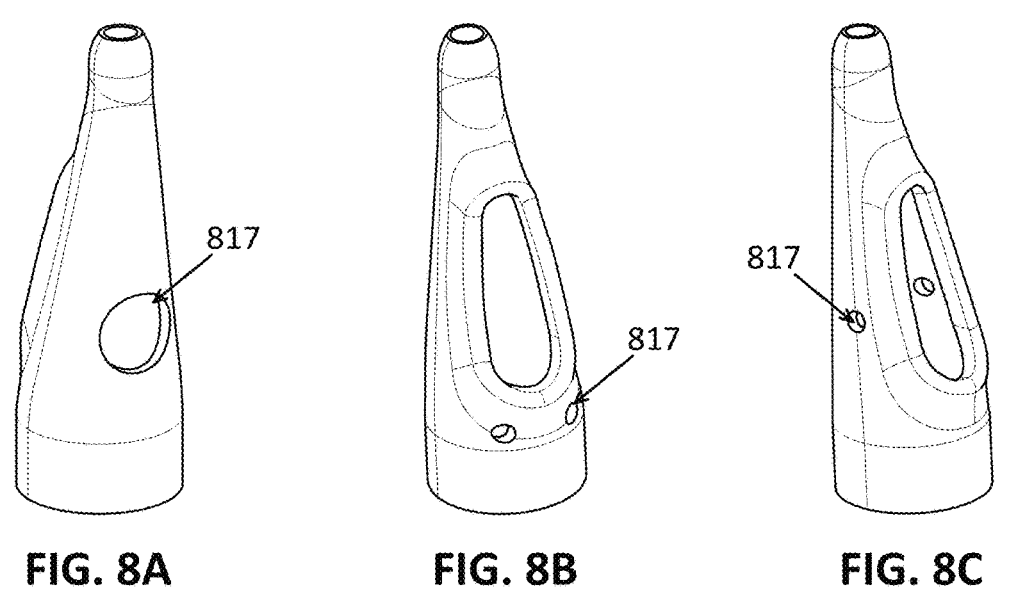
FIG. 8A
FIG. 8B
FIG. 8C

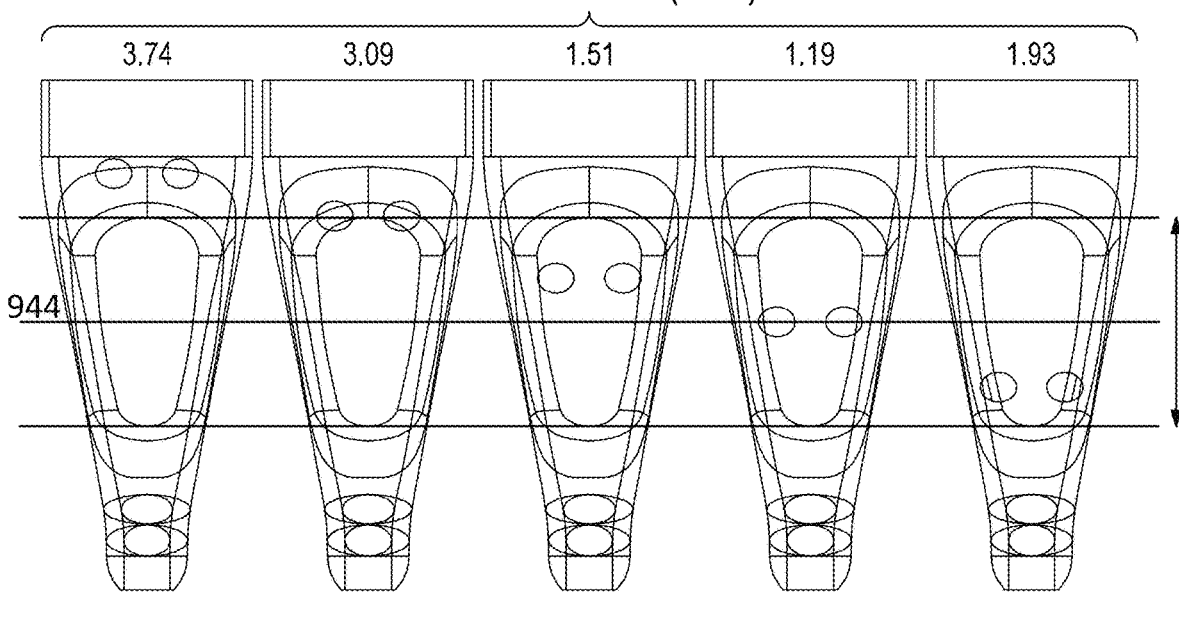
TIME TO ASPIRATE (SECS)
| 3.74 | 3.09 | 1.51 | 1.19 | 1.93 |
944
FIG. 9A    FIG. 9B    FIG. 9C    FIG. 9D    FIG. 9E
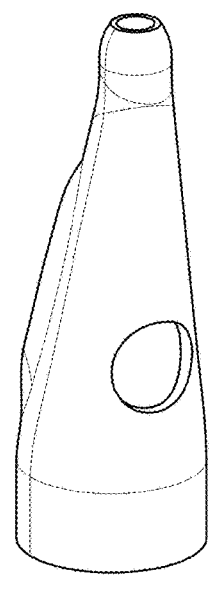
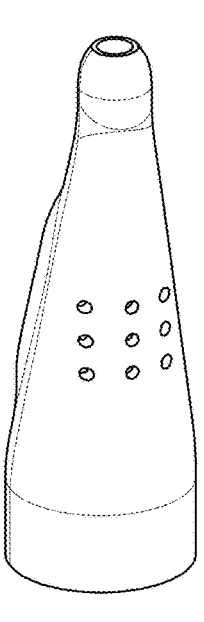
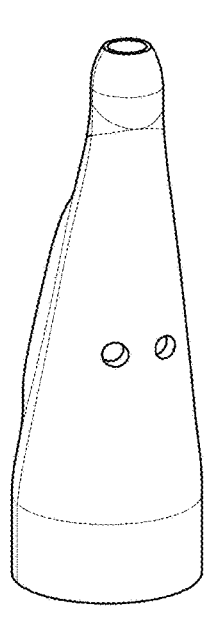
FIG. 10A              FIG. 10B              FIG. 10C

| RATIO | ORIFICE AREA (mm²) | CFE AREA (mm²) | HOLE DIA (mm) | HOLE DIA (in) |
|---|---|---|---|---|
| 8 | 35.63 | 4.4537 | 1.68 | 0.066 |
| 10 | 35.63 | 3.563 | 1.51 | 0.059 |
| 12 | 35.63 | 2.9691 | 1.37 | 0.054 |
| 14 | 35.63 | 2.545 | 1.27 | 0.050 |
| 18 | 35.63 | 1.9794 | 1.12 | 0.044 |
| 22 | 35.63 | 1.6195 | 1.02 | 0.040 |

| RATIO | 8 | 10 | 12 | 14 | 16 | 18 | 22 |
|---|---|---|---|---|---|---|---|
| TRIAL 1 | 2.08 | 1.53 | 1.20 | 1.09 | 1.56 | 2.16 | 1.3 |
| TRIAL 2 | 3.14 | 2.34 | 0.81 | 1.67 | 1.85 | 1.5 | 1.82 |
| TRIAL 3 | 2.1 | 1.86 | 1.58 | 1.29 | 1.77 | 1.96 | 2.45 |

1444

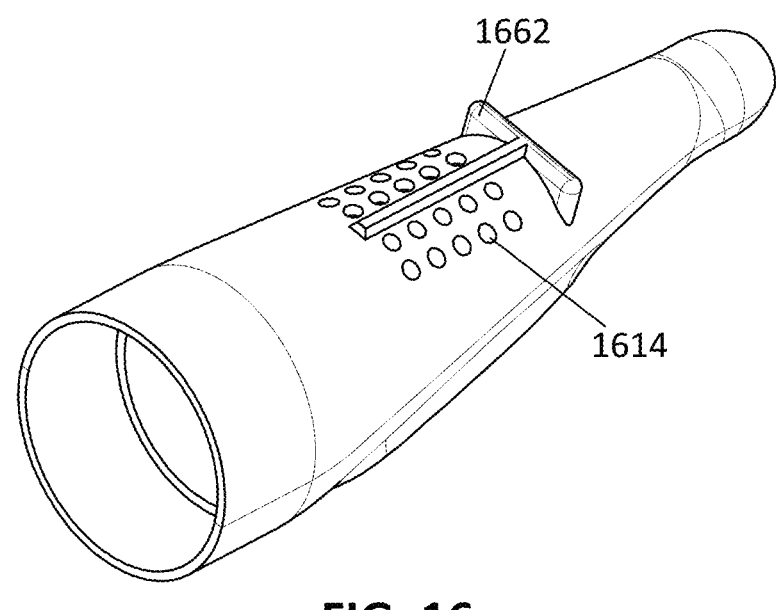
FIG. 16
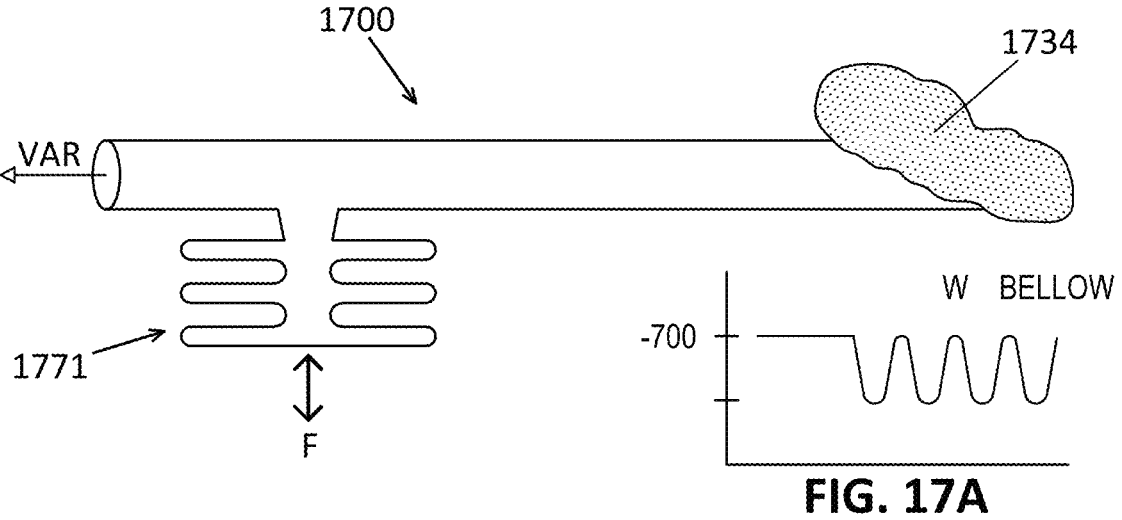
FIG. 17
FIG. 17A
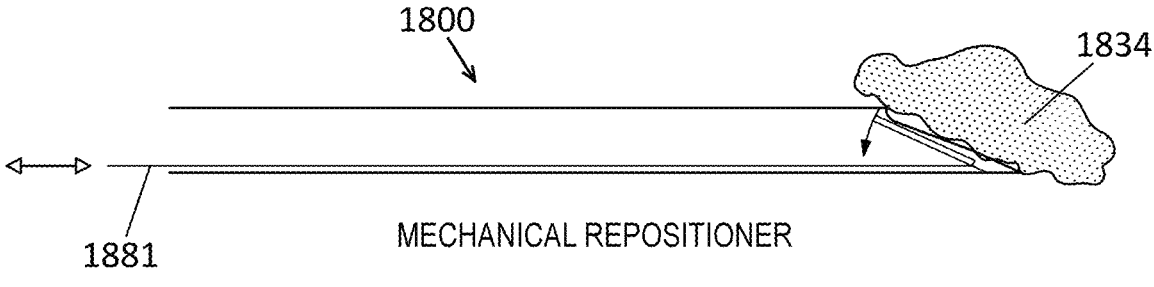
MECHANICAL REPOSITIONER
FIG. 18

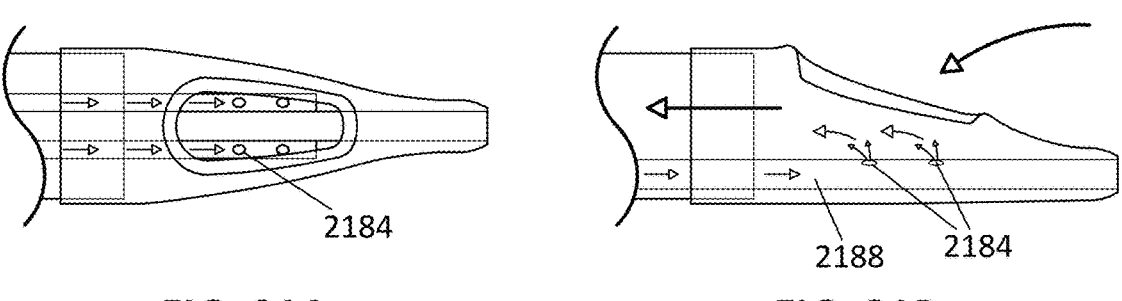
2184
FIG. 21A
2188  2184
FIG. 21B
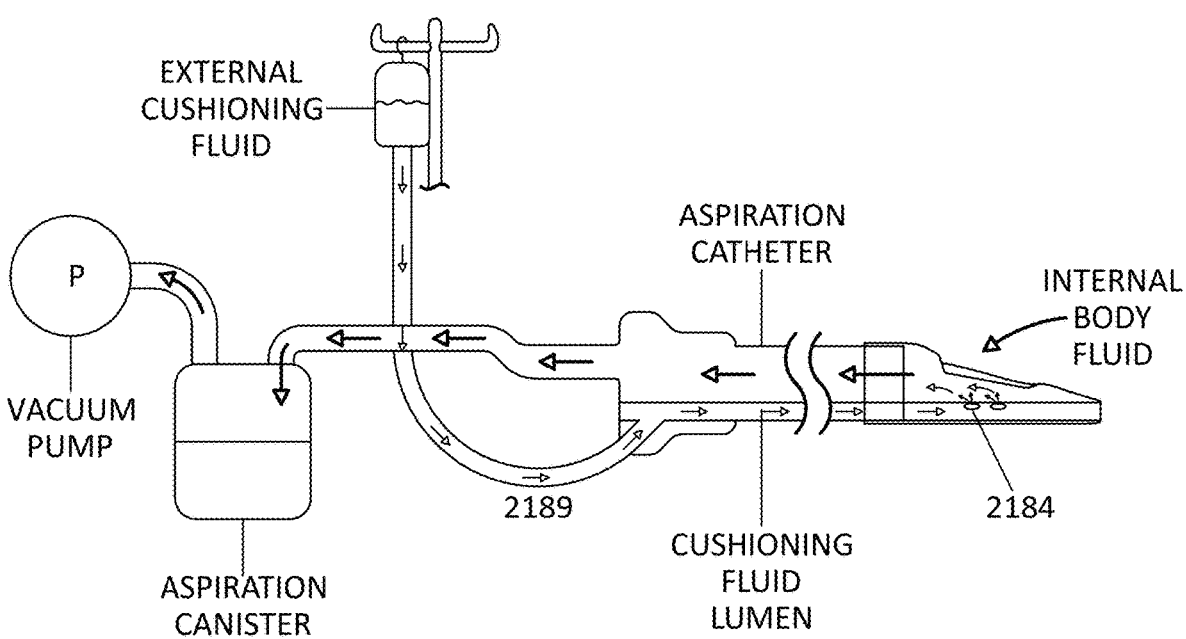
EXTERNAL
CUSHIONING
FLUID
ASPIRATION
CATHETER
INTERNAL
BODY
FLUID
P
VACUUM
PUMP
2189
2184
ASPIRATION
CANISTER
CUSHIONING
FLUID
LUMEN
FIG. 21C

A-A

POSITIONING LATERAL ASPIRATION OPENING NEAR CLOT WITHIN LUMEN OF VESSEL
2201

APPLY ASPIRATION THROUGH SUCTION LUMEN TO DRAW CLOT INTO ASPIRATION LUMEN WHILE IMPARTING ROTATIONAL MOMENT ON CLOT BY DRAWING FLUID FROM CUSHIONING FLOW OPENINGS THAT ARE DISTAL TO THE SUCTION LUMEN AND/OR LATERALLY OPPOSITE DISTAL END PORTION OF SUCTION LUMEN
2203

CONTINUE ASPIRATION TO ROTATE CLOT AND DRIVE CLOT AGAINST THE PROXIMAL EDGE OF SUCTION LUMEN (E.G., FLIPPING THE CLOT RELATIVE TO THE ASPIRATION OPENING)
2205

CONTINUE TO ASPIRATION TO REMOVE LONG STRANDS OF CLOT MATERIAL
2207

FIG. 22

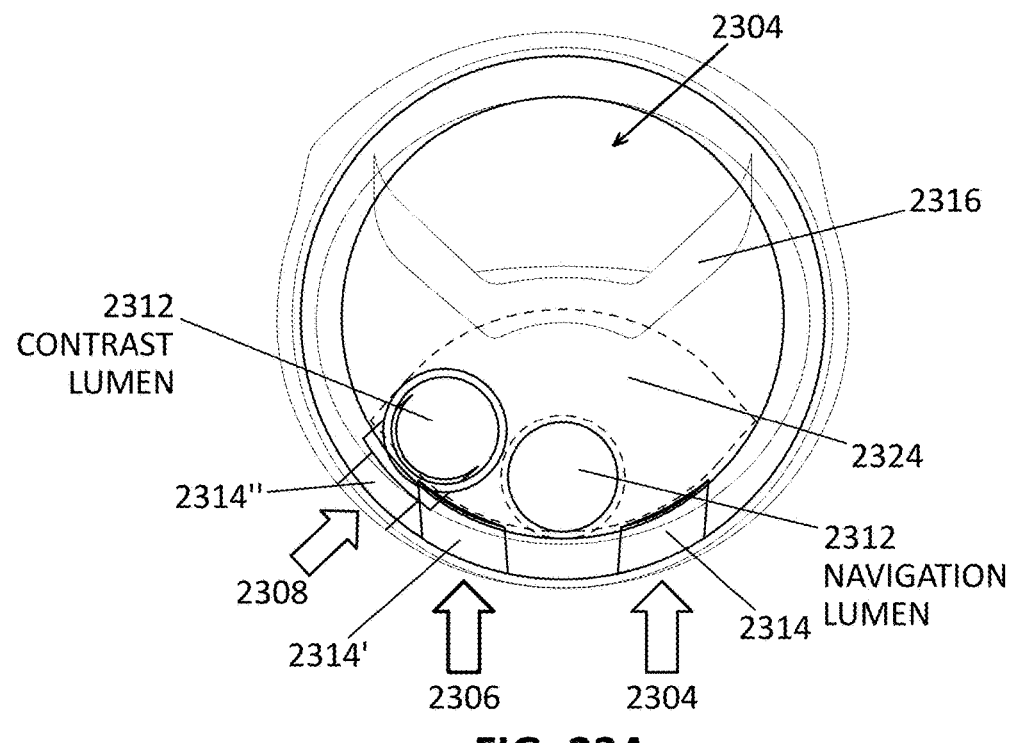

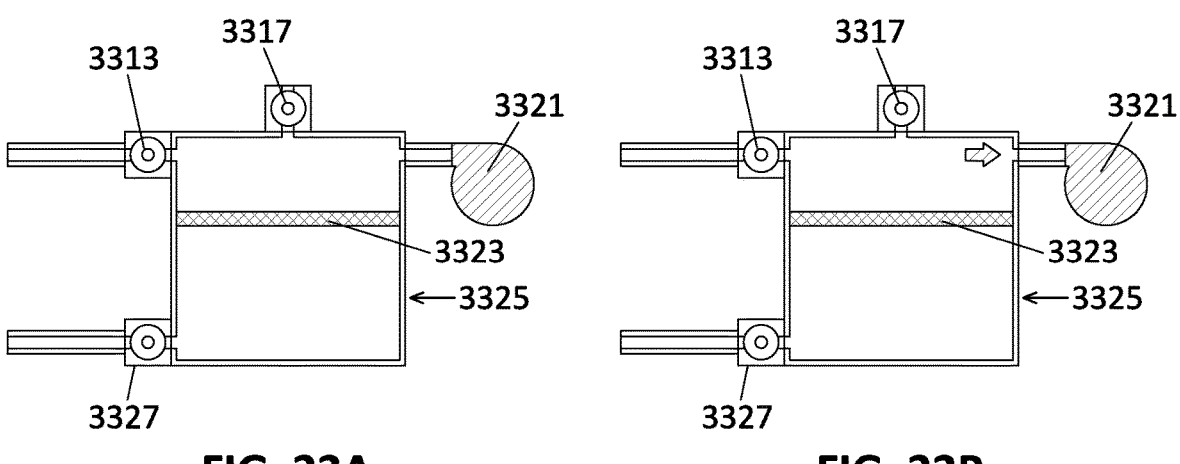
FIG. 33A          FIG. 33B
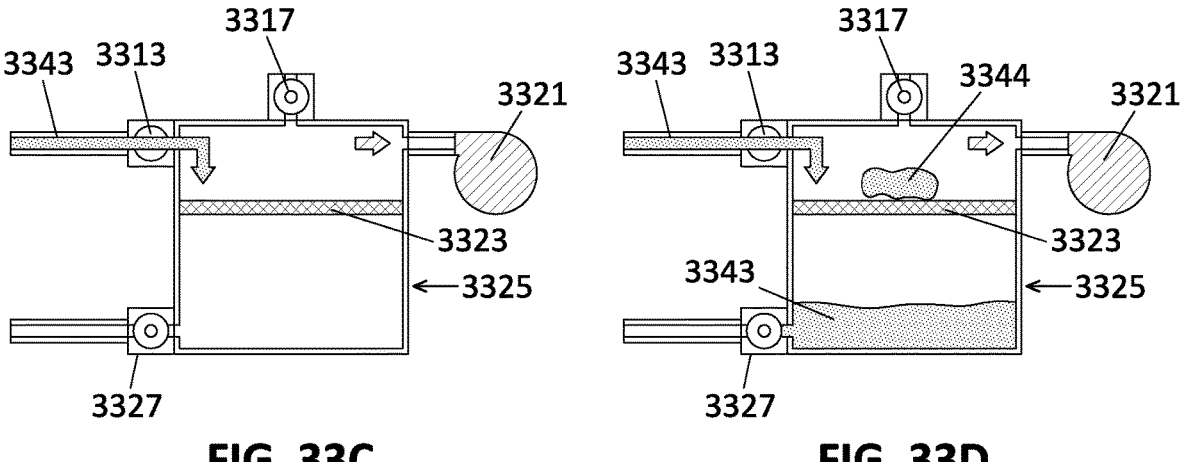
FIG. 33C          FIG. 33D
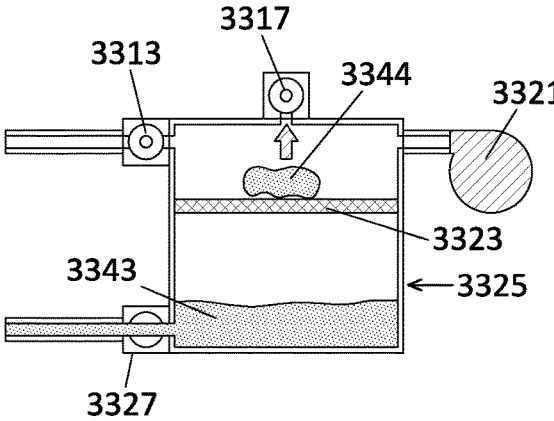
FIG. 33E

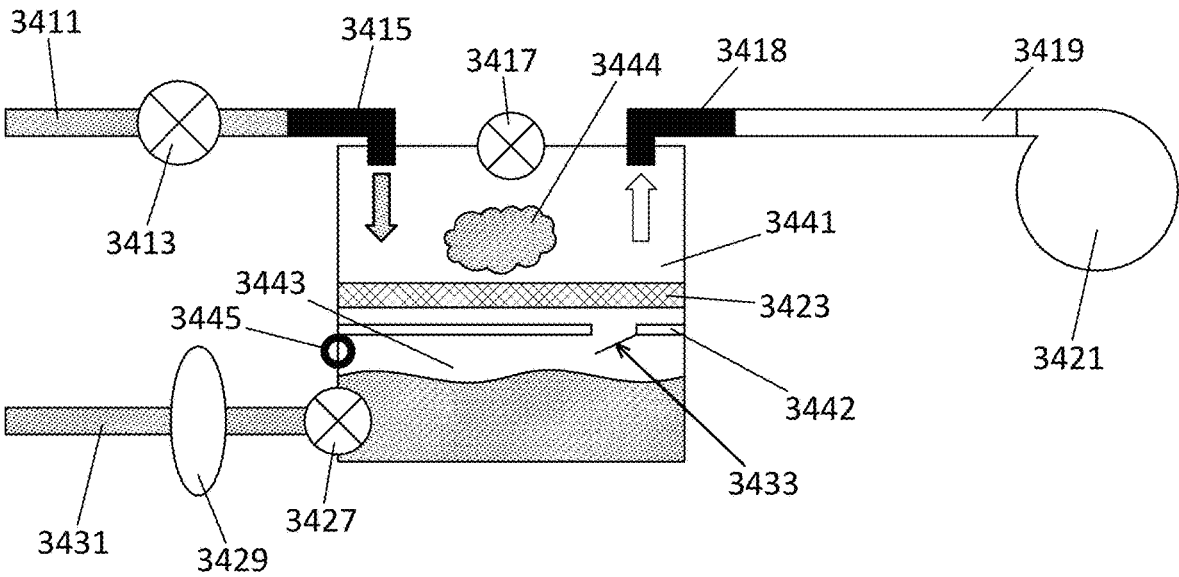
FIG. 34
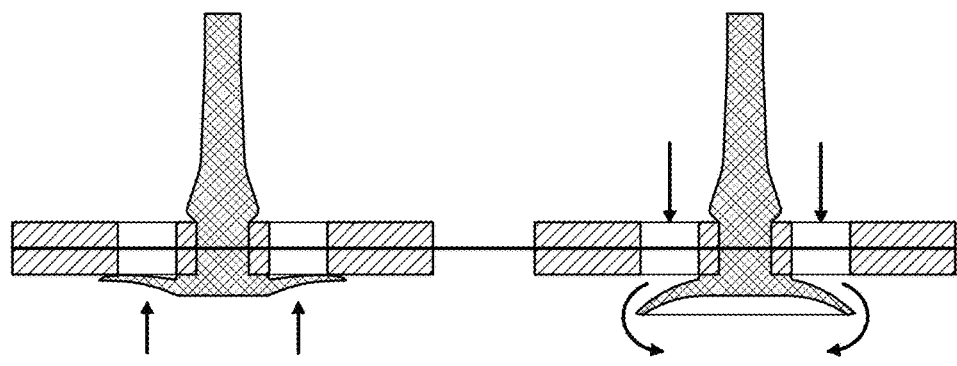
FIG. 35A          FIG. 35B

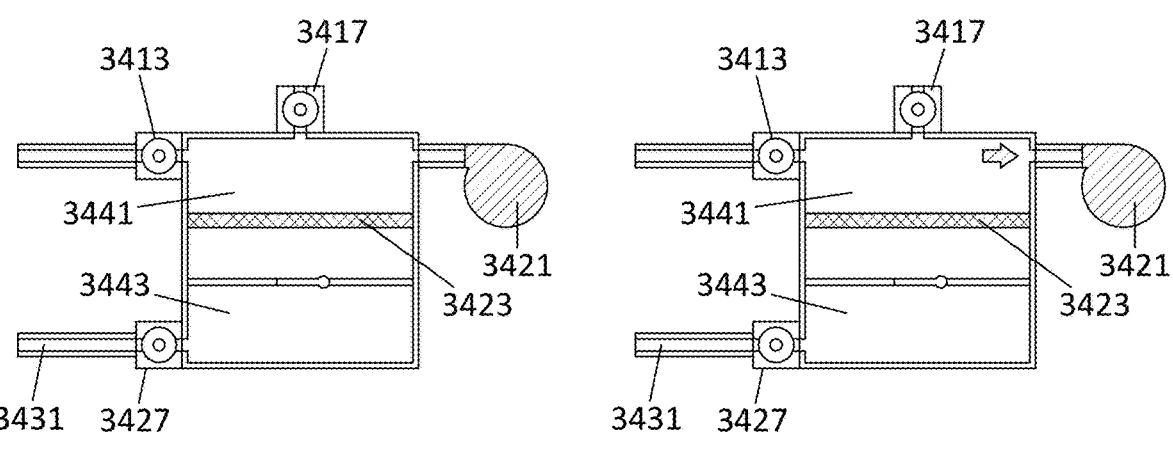
FIG. 36A          FIG. 36B
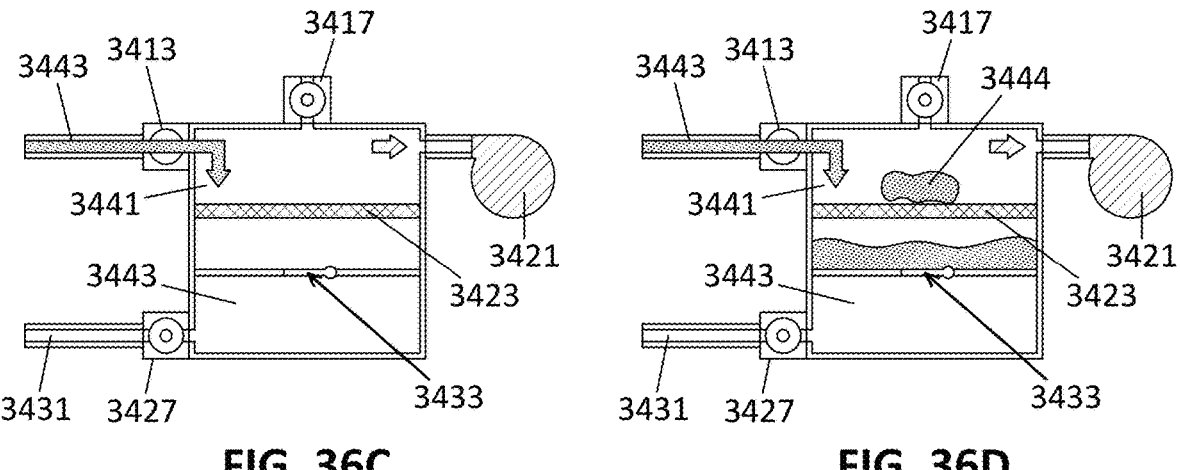
FIG. 36C          FIG. 36D
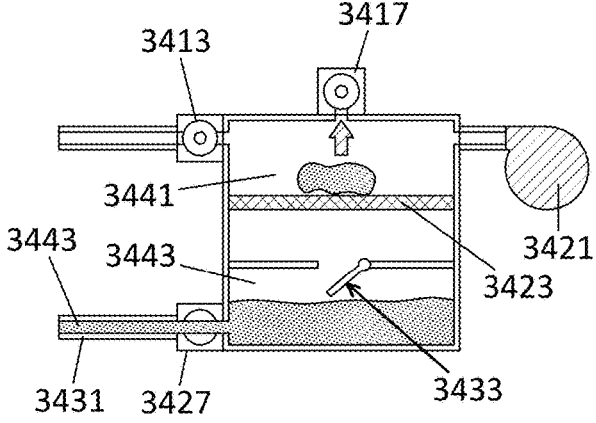
FIG. 36E

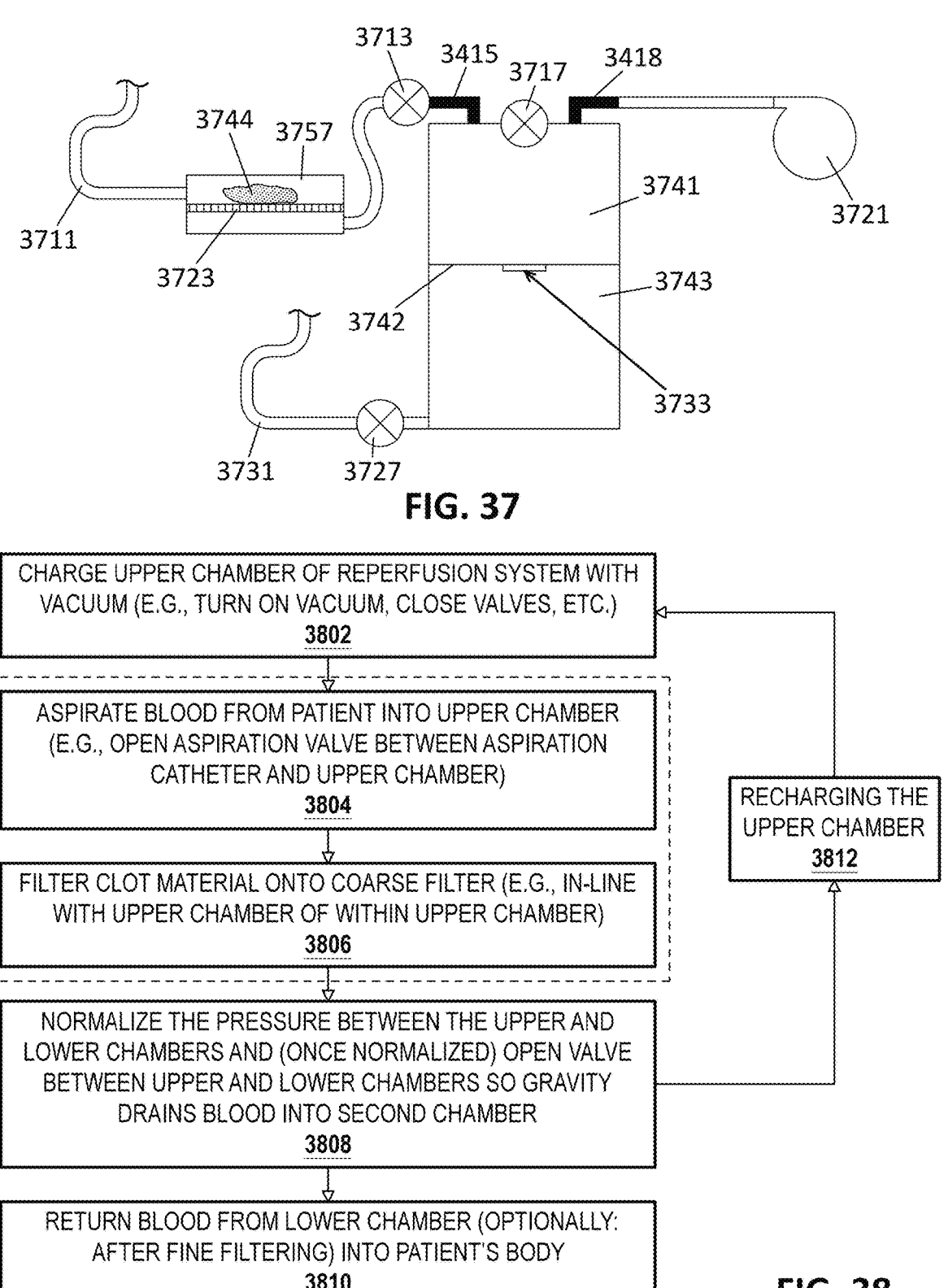

FIG. 37

CHARGE UPPER CHAMBER OF REPERFUSION SYSTEM WITH
VACUUM (E.G., TURN ON VACUUM, CLOSE VALVES, ETC.)
3802

ASPIRATE BLOOD FROM PATIENT INTO UPPER CHAMBER
(E.G., OPEN ASPIRATION VALVE BETWEEN ASPIRATION
CATHETER AND UPPER CHAMBER)
3804

FILTER CLOT MATERIAL ONTO COARSE FILTER (E.G., IN-LINE
WITH UPPER CHAMBER OF WITHIN UPPER CHAMBER)
3806

RECHARGING THE
UPPER CHAMBER
3812

NORMALIZE THE PRESSURE BETWEEN THE UPPER AND
LOWER CHAMBERS AND (ONCE NORMALIZED) OPEN VALVE
BETWEEN UPPER AND LOWER CHAMBERS SO GRAVITY
DRAINS BLOOD INTO SECOND CHAMBER
3808

RETURN BLOOD FROM LOWER CHAMBER (OPTIONALLY:
AFTER FINE FILTERING) INTO PATIENT'S BODY
3810

FIG. 38

METHODS FOR CLOT REMOVAL

CLAIM OF PRIORITY

This patent application is a continuation of U.S. patent application Ser. No. 18/859,162, titled "ASPIRATION APPARATUSES FOR CLOT REMOVAL," filed on Oct. 22, 2024, now U.S. Pat. No. 12,502,186, which is a national phase application under 35 USC 371 of International Patent Application No. PCT/US2023/066140, titled "ASPIRATION APPARATUSES FOR CLOT REMOVAL," filed on Apr. 24, 2023, now International Publication No. WO 2023/205815, which claims priority to U.S. provisional patent application No. 63/334,075, titled "ASPIRATION APPARATUSES FOR CLOT REMOVAL," filed on Apr. 22, 2022, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Devices and methods for removal of unwanted tissue such as thrombus, atheroma, fluid, polyps, cysts or other obstructive matter from body lumens, such as blood vessels, ureters, bile ducts or fallopian tube may use aspiration to draw the unwanted material into a collection device for removal from the body. In particular, a variety of catheter devices have been developed for use in intraluminal and intravascular procedures for fragmentation and removal of obstructive matter, such as blood clots, thrombus, atheroma, and the like, from blood vessels.

In many instances, the procedure may include breaking up the material (e.g., clot material), often by infusing the vessel or treatment site with fluid (saline or a thrombolytic agent) to assist in breaking up the clot or tissue into a particle size that can then be aspirated through a lumen of the treatment device or using a secondary catheter hooked up to a source of vacuum/suction. Depending on the method of fragmentation and the consistency of the clot or tissue, the particle size can vary. If the material is not thoroughly fragmented, the larger particles can build up in the catheter and block the aspiration lumen.

However, these procedures may result in the release of smaller fragments back into the body, which is undesirable. Further, larger fragments may still clog the devices and require much more involved procedures, increasing the risk of complications due to blood loss and extended procedure times. Thus, there is a need for more efficiently evacuating material, e.g., blood clots, from the vessel or body lumen. Furthermore, it would be desirable to have devices that allowed aspiration of larger particles without requiring disruption of the clot material, thereby reducing procedure time. Preferably, such improved devices will have a low profile to enable percutaneous use and will be flexible and torqueable to enable their use in tortuous lumens. Furthermore, such devices may preferably be designed to be placed over a guidewire.

SUMMARY OF THE DISCLOSURE

Described herein are aspiration catheters for removing clot material from a patient, systems including these catheter as well as methods of making and using these aspiration catheters in particular, these catheters may be configured to remove clot in longer continuous strips that prevent release of smaller clot fragments back into the vessel which would be problematic. The apparatuses (e.g., devices and systems, including in particular the aspiration catheters) and methods described herein may be configured to include inlets (e.g., openings) that are configured and positioned to generate a cushioning flow of fluid laterally past (and in some cases counter to) suction into the catheter through a side-facing aspiration opening in a manner that imparts rotational momentum or force (e.g., a rotational moment) on the clot as it is driven against the distal edge of the aspiration opening results in a continuous cutting of the clot into long strips that may be concurrently pulled into the aspiration lumen of the catheter. Thus, these generally distal openings may be referred to herein as cushioning flow openings. The cushioning flow openings may be opening into the vessel and/or they may be openings for fluid applied through a sub-lumen (e.g., separate from the aspiration lumen and/or running through and/or adjacent to the aspiration lumen). The methods and apparatuses described herein may be particularly well suited for removal of clots from larger vessels, including (but not limited to) pulmonary embolism and thrombectomy, including peripheral thrombectomy.

The aspiration catheters described herein provide numerous advantages as compared with other aspiration catheters for removing clot. In particular the methods and apparatuses described herein may be configured to apply an entraining flow of fluid (e.g., blood or other fluid) that rotate (and/or flip) the clot within the vessel and drive the clot against a proximal edge of the aspiration opening without violently disrupting the clot. Unlike other apparatuses that provide "jets" of fluid (including blood) intended to disrupt and break apart the clot, the apparatuses described herein, and in particular the cushioning flow openings are configured to prevent such disruption and breaking of the clot material. In particular, the features of the cushioning flow openings described herein define specific parameter ranges that result in the gentler rotational movement on the clot that may result in cutting strips of clot material from the clot. These ranges may include the longitudinal position of at least some of the cushioning flow openings relative to the aspiration lumen, the size of the cushioning flow openings relative to the aspiration lumen, the radial position of the cushioning flow openings relative to the aspiration opening, and/or the number of cushioning flow openings. As will be described herein, outside of these ranges the aspiration catheter may not operate as effectively, may not provide a rotational force, may not cut strips of clot material as described herein and/or may jam or "lollypop" the clot material in the aspiration opening. The cushioning flow openings described herein may also be optimized to both minimize the amount of blood lost during the aspiration procedure and/or to increase the speed of removing clot material.

For example, described herein are aspiration catheters (e.g., suction catheters) having one or more cushioning flow openings in which one or more of the cushioning flow openings are positioned distal of a central (along the longitudinal axis of the distal tip region). In general, the cushioning flow openings may be radially opposite from the aspiration opening (e.g., radially offset by more than 90 degrees, e.g., more than 100 degrees, more than 110 degrees, more than 120 degrees, etc.) from the longitudinal midline of the aspiration opening. In general, the cushioning flow openings may include at least one cushioning flow openings that is positioned opposite from the aspiration opening and distal to the longitudinal midpoint of the aspiration opening. In some examples, the cushioning flow openings may have a geometric center of the sum of all of the cushioning flow openings that is within +/−20% of the center of the longitudinal midpoint of the aspiration opening (and in particular, the geometric center may be distally offset from the longitudinal midpoint of the aspiration opening).

For example, a suction catheter device may include: an elongate body having a suction lumen; a distal end region extending from the elongate body, the distal end region having an aspiration opening extending along a length of a lateral side of the distal end region; and one or more cushioning flow openings through a side of the distal end region opposite of the aspiration opening, wherein the one or more cushioning flow openings collectively have a geometric center along the length of the lateral side of the distal end region that is within +/−20% of a longitudinal center of the aspiration opening, wherein the one or more cushioning flow openings are configured to apply rotation (e.g., to transfer rotation momentum) to a clot material to drive the clot material against a proximal edge of the aspiration opening to cut an elongate strip from the clot material and to entrain the elongate strip so that it is pulled down proximally within the suction lumen.

A suction catheter device may include: an elongate body having a suction lumen; a distal end region extending from the elongate body, the distal end region having an aspiration opening extending along a length of a lateral side of the distal end region; and one or more cushioning flow openings through a side of the distal end region opposite of the aspiration opening and/or a distal end of the distal end region, wherein the one or more cushioning flow openings collectively have a geometric center along the length of the lateral side of the distal end region that is distal of a longitudinal center of the aspiration opening, wherein the one or more cushioning flow openings are configured to apply rotation (e.g., apply angular momentum) on a clot material to drive the clot material against a proximal edge of the aspiration opening to cut an elongate strip from the clot material and to entrain the elongate strip so that it is pulled down proximally within the suction lumen.

A suction catheter device may include: an elongate body having a suction lumen; a distal end region extending from the elongate body, the distal end region having an aspiration opening extending along a length of a lateral side of the distal end region; and a plurality of between 2-20 (e.g., between 2-16, between 2-10, between 2-8, etc.) cushioning flow openings through a side of the distal end region opposite of the aspiration opening, wherein the plurality of cushioning flow openings collectively have a geometric center along the length of the lateral side of the distal end region that is at or distal to a longitudinal center of the aspiration opening, wherein the plurality of cushioning flow openings are configured to apply rotation (e.g., apply angular momentum) on a clot material to drive clot material against a proximal edge of the aspiration opening to cut an elongate strip from the clot material and to entrain the elongate strip so that it is pulled down proximally within the suction lumen.

In some examples a suction catheter device includes: an elongate body having a suction lumen; a distal end region extending from the elongate body, the distal end region having an aspiration opening extending along a length of a lateral side of the distal end region; and a plurality of between 2-20 (e.g., between 2-16, between 2-10, between 2-8, etc.) cushioning flow openings through a side of the distal end region opposite of the aspiration opening, wherein the plurality of cushioning flow openings collectively have a geometric center along the length of the lateral side of the distal end region that is at or distal to a longitudinal center of the aspiration opening, wherein a ratio between an area of the aspiration opening and a combined area of the plurality of cushioning flow openings is between 12:1 and 14:1, further wherein the plurality of cushioning flow openings are configured to apply rotational (e.g., angular momentum) on a clot material to drive clot material against a proximal edge of the aspiration opening to cut an elongate strip from the clot material and to entrain the elongate strip so that it is pulled down proximally within the suction lumen.

In any of these apparatuses, the distal end region may be configured as a distal tip coupled to the elongate body. The distal end region may include the aspiration opening and the one or more cushioning flow openings.

In general, the collective geometric center of the one or more cushioning flow openings may be within +/−10% of the longitudinal center of the aspiration opening, and in particular may be distal to the longitudinal center of the aspiration opening. For example, the collective geometric center of the one or more cushioning flow openings may be at or distal to the longitudinal center of the aspiration opening. In some examples the cushioning flow openings may include at least one opening that is distal to the longitudinal center. For example, the at least one of the one or more cushioning flow openings may be distal to the longitudinal center of the aspiration opening.

Any number of cushioning flow openings may be used, including one, two, three, four, five, six, seven, eight, etc. For example, the one or more cushioning flow openings may comprise between 2-8 cushioning flow openings.

Any of the apparatuses described herein may include a surface that extends from the catheter and/or from the distal end region that may prevent clogging of the cushioning flow openings. The surface may be configured as a projection and/or as a should. For example, any of these apparatuses may include a shroud extending from an outer surface of the elongate body opposite from the aspiration opening distal to the cushioning flow openings, wherein the shroud is configured to prevent clot material from entering the cushioning flow openings. In some cases the shroud may be expandable, inflatable, etc. In some cases the shroud or projection may be part of a lumen (e.g., a guide lumen or diagnosis catheter lumen, etc.). In some cases the shroud or projection may be configured to prevent clot (distal to the tip) from extending back and into the cushioning flow openings. In some examples the same or a different shroud may be configured to prevent the cushioning flow openings from sucking onto the wall of the lumen (e.g., the wall of the vessel).

As mentioned, in general, the cushioning flow openings may be positioned opposite from the aspiration opening, in the radial direction. In some cases the cushioning flow openings may be rotational positioned between 90 degrees and 180 degrees (e.g., between 90 and 145, between 90 and 180, etc.) from a longitudinal midline through the aspiration opening.

Any of these apparatuses may include a guide lumen or navigational lumen extending adjacent to the suction lumen along the distal end region opposite from the aspiration opening. This guide or navigation lumen (collectively referred to herein as a navigation lumen) may be configured to receive a guide catheter or guide wire. In some cases, the guide or navigation lumen may be configured to receive a diagnostic catheter that may be extended distally out of the aspiration catheter.

In any of these examples, the cushioning flow openings may pass through and/or be occluded or shielded by a navigation lumen; in some examples the cushioning flow openings may be opened/closed by extending or withdrawing an elongate member, such as a diagnostic catheter, within the lumen. When the diagnostic catheter is extended distally to the cushioning flow openings, the openings may be closed or blocked, partially or completely, by the diagnostic catheter allowing them to be switched "off" or "on" by longitudinally repositioning the diagnostic catheter. For example, the one or more cushioning flow openings may extend through the navigational lumen so that the cushioning flow openings may be opened or closed by passing an elongate member through the navigational lumen. Alternatively, in some examples the cushioning flow openings may be configured to be opened regardless of the position of the diagnostic catheter. In any of the apparatuses described herein the profile of the navigation lumen may be configured to protect the cushioning flow openings and prevent them from clogging or being blocked by clot material and/or luminal wall. In some examples the profile of the navigation lumen may be configured to help direct the flow of fluid through the cushioning flow openings, e.g., so that it may more effectively impart a rotation on clot material within or adjacent to the aspiration opening. For example, in some cases the one or more cushioning flow openings may include two or more cushioning flow openings arranged on one either side of the navigation lumen.

Any of the apparatuses described herein may be optimized so that the flow through the cushioning flow openings is configured to entrain fluid within the suction lumen down the length of the suction lumen and to impart rotation (e.g., angular momentum) on the clot material against the proximal end/edge of the aspiration device. For example, any of these apparatuses (e.g., devices, systems, etc.) may be configured so that the opening surface area of the aspiration opening as compared to the sum of the opening surface areas of the cushioning flow openings is between about 10:1 to 18:1 (e.g., 10:1 to 17:1, 10:1 to 16:1, etc.). For example, in some examples the ratio between an area of the aspiration opening and a combined area of the one or more cushioning flow openings is between 10:1 and 16:1. In some examples, the ratio between an area of the aspiration opening and a combined area of the one or more cushioning flow openings is between 12:1 and 14:1. Outside of these ratios the apparatus may not operate as efficiently and may take substantially longer to aspiration the clot.

In general, the cushioning flow openings may be configured to impart rotation on the clot positioned in or adjacent to the lateral and/or tapered aspiration opening. This angular momentum results in driving the clot material against the proximal edge of the aspiration orifice and may therefore cut the clot material; in particular it may cut it into relatively long and thin strips while controlling the movement of the clot. In large vessel this may result in the clot being rotated against the proximal edge of the aspiration opening. However, even in smaller vessels, the rotational moment, while not rotating the clot because of the size constraints of the vessel, may instead drive the clot against the aspiration opening in a manner similar to a carriage of a typewriter, e.g., by driving the clot material axially along the aspiration orifice edge in a distal to proximal direction, then moving the clot material proximal to distal and repeating the distal-to-proximal cutting. This movement, which may be the result of the combination of the force of aspiration through the aspiration opening as well as the rotational force (e.g., rotational moment) imparted by the flow from the cushioning flow openings, repeats until the clot is small enough to completely pass through the aspiration lumen.

As mentioned above, any of these apparatuses may include a displacement projection (e.g., shroud) extending from an outer surface of the distal end region configured to displace an outer opening of the one or more cushioning flow openings from a wall of a vessel into which the distal end region is inserted.

In general, the distal end region of the apparatus may be tapered on at least the length of a lateral side of the distal end region including the aspiration opening. Thus, the proximal outer edge region of the aspiration opening, against which the clot material is being driven and rotated (or flipped) may be larger than the distal edge region, e.g., the aspiration opening may be wider at a proximal end than at a distal end.

In general, the aspiration opening may be reinforced either or both around the perimeter of the opening and/or radially around the distal tip. For example the aspiration opening may include a lip region that is reinforced. The aspiration opening may be enlarged and/or may include a structural reinforcement (wire, etc.). Thus, the aspiration opening may include a reinforced lip region circumscribing at least the proximal edge of the aspiration opening. The reinforcement structure may strengthen the lip region of the aspiration opening, but the aspiration opening may still have an atraumatic outer surface that enables advancement of the apparatus within the vessel with the aspiration orifice effectively open without cutting or damaging the vessel wall. Alternatively or additionally, in some embodiments, the aspiration orifice may be covered, e.g., with an elastic membrane that deflects inward and/or radially as aspiration is applied and clot enters the orifice. In embodiments with the aspiration orifice covered, the aspiration force required to expose the aspiration orifice is less than the force to entrain fluid through the cushioning flow openings.

Although the aspiration opening is generally atraumatic (e.g., configured so as not to cut or snag the wall of the vessel, in some examples the aspiration opening includes a cutting edge or surface on at least the proximal edge of the aspiration opening, preferable in a lip region that is separate from the lateral face of the aspiration opening. For example, the aspiration opening, or at least the proximal end region, may include a cutting surface that is recessed relative to the outer surface and edge, which may be rounded or atraumatic. Alternatively or additionally, the proximal edge region may be thinner than the more lateral and/or distal edge regions of the aspiration opening, which may assist in cutting the clot material driven against the proximal edge region.

Any of the apparatuses described herein may include a sensor or sensors for detecting the presence of clot material, including detecting that clot is still present at the aspiration opening and/or within the lumen of the aspiration catheter. Any of these apparatuses may include a clot sensor configured to detect a clot material in communication with the aspiration opening and/or within the distal end region.

In any of the apparatuses described herein the cushioning flow openings may include a distal opening at a distal end of the apparatus. The distal end opening may be separate from the cushioning flow openings on the sidewall of the apparatus.

For example, described herein are suction catheter devices comprising: an elongate body having a suction lumen; a distal end region extending from the elongate body, the distal end region having an aspiration opening extending along a tapered length of a lateral side of the distal end region; and a plurality of cushioning flow openings through a lateral side of the distal end region opposite of the aspiration opening, wherein at least one of the plurality of cushioning flow openings is distal to a longitudinal center of the aspiration opening; wherein the aspiration opening is configured so that a diameter of the suction lumen at a distal edge of the aspiration opening is 40% or more of a diameter of the suction lumen at a proximal edge of the aspiration opening, and wherein the plurality of cushioning flow openings are configured to form a region of cushioning flow within the suction lumen opposite of the aspiration opening to apply a rotational force on a clot material.

In any of the devices described herein the plurality of cushioning flow openings may comprise between 2-20 cushioning flow openings. The device described herein may include a navigation channel having a lumen extending within the suction lumen and configured to at least partially obstruct the plurality of cushioning flow openings. The plurality of cushioning flow openings may be positioned between 60 degrees and 120 degrees from a longitudinal midline through the aspiration opening. Any of these devices may include a navigational channel comprising a lumen extending adjacent to the suction lumen along the distal end region opposite from the aspiration opening. In any of these apparatuses, one or more additional cushioning flow openings extend through the navigational lumen. The plurality of cushioning flow openings may include two or more cushioning flow openings arranged on either side of the navigation lumen.

The navigation lumen may be configured to have a distal end opening within the suction lumen proximal to the distal tip region of the lumen. A ratio between an area of the aspiration opening and a combined area of the plurality of cushioning flow openings may be between 10:1 and 16:1. In some examples a ratio between an area of the aspiration opening and a combined area of the plurality of cushioning flow openings is between 12:1 and 14:1.

The aspiration opening may comprise a reinforced lip region circumscribing at least the proximal edge of the aspiration opening. The aspiration opening may be wider at a proximal end than at a distal end.

Any of the catheters described herein may include a holdup region at a distal end of the suction lumen, distal to the aspiration opening.

For example, a suction catheter device may include: an elongate body having a suction lumen; a distal end region extending from the elongate body, the distal end region having an aspiration opening extending along a tapered length of a lateral side of the distal end region; and a plurality of cushioning flow openings through a lateral side of the distal end region opposite of the aspiration opening, wherein at least one of the plurality of cushioning flow openings is distal to a longitudinal center of the aspiration opening; wherein the aspiration opening is configured so that a diameter of the suction lumen at a distal edge of the aspiration opening is 40% or more of a diameter of the suction lumen at a proximal edge of the aspiration opening, and wherein the plurality of cushioning flow openings are configured to form a region of cushioning flow within the suction lumen opposite of the aspiration opening to apply a rotational force (e.g., angular force) on a clot material to drive the clot material against the proximal edge of the aspiration opening to cut a strip from the clot material without fragmenting the clot material.

The cushioning flow openings may be holes formed through a side wall of the distal end region (distal tip) perpendicular through the distal end region between the outer surface and the inner surface, or in some cases the cushioning flow openings may be oriented to direct the flow slightly (e.g., proximally). Although in general, the apparatuses and methods described herein may be configured with cushioning flow openings through the side wall of the distal end region of the aspiration catheter, any of the methods and apparatuses described herein may include an outlet for the cushioning flow openings that is opposite from the aspiration opening as described herein, but the inlet into the cushioning flow openings may be more proximally located, e.g., proximal to the distal tip region. In general, these apparatuses may be configured to draw blood from the lumen in which the apparatus is positioned. In some examples the apparatus may be configured to apply fluid from an external source (e.g., blood, saline, etc.). For example, any of the method and apparatuses described herein may be configured to apply fluid from a fluid line to the cushioning flow openings, in the cushioning flow opening described herein refer to the outlet of the cushioning flow opening (e.g., the inlet may be proximal, including outside of the patient and the outlet may be coupled to a fluid line extending proximally).

In general, described herein are methods of using an apparatus such as those described above. For example, described herein are methods including rolling the clot material relative to the aspiration opening when removing the clot material. In some examples the method includes a method of removing clot material comprising: positioning an elongate aspiration opening of a suction catheter adjacent to a clot within a lumen of a vessel, wherein the aspiration opening extends on a lateral side of a distal end region of the suction catheter, further wherein the suction catheter comprises one or more cushioning flow openings through a side of the distal end region that is opposite of the aspiration opening; applying suction through a suction lumen of the suction catheter to draw the clot and a fluid into the suction catheter from the aspiration opening and to draw fluid through the one or more cushioning flow openings, wherein the one or more cushioning flow openings are configured relative to the aspiration opening so that flow of fluid into the suction catheter imparts a rotational force (e.g. angular force) on the clot, driving the clot against a proximal edge of the aspiration opening, cutting the clot against the proximal edge, and flipping the clot relative to the aspiration opening.

Applying suction may comprise applying greater than 10 mmHg of suction (e.g., an approximately 10 mmHg or more difference between atmospheric pressure and the pressure within the catheter). Applying suction may comprise drawing fluid through the one or more cushioning flow openings that collectively have a geometric center that at or distal to a longitudinal center that is within 10% of a longitudinal midpoint of the aspiration opening (e.g., wherein at least one of the cushioning flow openings are positioned distal to the longitudinal center of the aspiration opening, etc.). In some examples, applying suction comprises drawing fluid through the one or more cushioning flow openings that collectively have a geometric center that at or distal to a longitudinal center that is at or distal to a longitudinal midpoint of the aspiration opening.

Any of these methods may include cutting an elongate strip of clot material from the clot as it is driven against the proximal edge of the aspiration opening and translated (e.g. flipped or moved/reciprocated axially moved back and forth) relative to the aspiration opening. The one or more cushioning flow openings may be configured to draw fluid into the suction catheter so that the fluid entrains a strip of clot material that is cut when the clot material is driven against the proximal edge of the aspiration opening.

Applying suction through the suction catheter to draw fluid through the one or more cushioning flow openings may include entraining flow of fluid down a length of a suction lumen without substantially disrupting the cut clot within the suction lumen.

In any of these methods, the clot outside of the aspiration catheter may be rolled and/or flipped by the flow driven by the cushioning flow openings and the aspiration opening. Flipping the clot relative to the aspiration opening may comprise rotating the clot within the vessel against the aspiration opening of the suction catheter.

As mentioned, any of these apparatuses and methods may include the use of one or more clot-sensing sensors. Thus, any of these methods may also include automatically shutting off or reducing suction when clot is no longer detected adjacent to the aspiration opening or within the distal end region.

Also described herein are methods of removing clot in relatively long strands. Unlike previously described systems that may break apart the clot, including by the use of one or more "jets" of fluid applied before, during or after aspiration, the methods and apparatuses described herein may be configured to instead remove strips of clot in relatively long lengths. For example, described herein are methods of removing clot material that include: positioning an elongate aspiration opening of a suction catheter adjacent to a clot within a lumen of a vessel, wherein the aspiration opening extends on a lateral side of a distal end region of the suction catheter, further wherein the suction catheter comprises one or more cushioning flow openings through a side of the distal end region that is opposite of the aspiration opening; applying suction through a suction lumen of the suction catheter to draw the clot against a proximal edge of the aspiration opening of the suction catheter while drawing fluid through the one or more cushioning flow openings so that a strip of clot material is cut by the proximal edge of the suction catheter, wherein the cushioning flow openings are configured so that fluid drawn into the suction catheter through the one or more cushioning flow openings entrain the strip of clot material to draw it proximally down the suction catheter without substantially disrupting the strip of clot material.

In any of these methods, positioning the elongate aspiration opening may comprise spacing the one or more cushioning flow openings away from a wall of the vessel.

Any of these methods may include applying suction by applying greater than 10 mmHg of pressure (e.g., a difference of more than 10 mmHg relative to atmosphere and/or pressure within eh vessel). In general, the cushioning flow openings may be positioned or configured so that at least one cushioning flow opening (e.g., or at least 2 cushioning flow openings, at least 3 cushioning flow openings, at least half of the cushioning flow openings, etc.) are distal to the longitudinal midpoint of the aspiration opening. In some examples applying suction may include drawing fluid through the one or more cushioning flow openings that collectively have a geometric center that at or distal to a longitudinal center that is within +/−20% (e.g., +/−10%, etc.) of a longitudinal midpoint of the aspiration opening. Applying suction may comprise drawing fluid through the one or more cushioning flow openings that collectively have a geometric center that at or distal to a longitudinal center that is at or distal to a longitudinal midpoint of the aspiration opening. In any of these apparatuses and methods, at least one cushioning flow opening may be distal to the longitudinal midpoint of the aspiration opening in order to provide the rotational force as described herein.

Any of these methods may include cutting an elongate strip of clot material from the clot as it is driven against the proximal edge of the aspiration opening and flipped relative to the aspiration opening.

The one or more cushioning flow openings may be configured relative to the aspiration opening so that flow of fluid into the suction catheter imparts a rotational force on the clot, driving the clot against a proximal edge of the aspiration opening. The methods described herein may include automatically shutting off or reducing suction when clot material is no longer detected adjacent to the aspiration opening or within the distal end region.

Also described herein are aspiration collection and reperfusion apparatuses and methods of using them to aspirate clot material from the vasculature in a manner that simplifies the return of aspirated blood to the patient safely and minimizes the exposure of the blood to low negative pressure. These apparatuses typically include an assembly including at least an upper chamber and a lower chamber. The upper chamber may receive and maintain a vacuum to allow aspiration when connected to an aspiration catheter. Additionally, the upper chamber may contain a filter element that may filter clot material removed from the patient. In some embodiments, the upper chamber may be separated into two chambers that are fluidly connected via a tube. In other embodiments, the filter element may be located within the lower chamber between the reperfusion valve and the reperfusion line. Blood may be transferred to the lower chamber in a manner that does not damage the blood or induce foaming. The apparatuses and methods of using them may allow immediate or near-immediate return of blood for reperfusion without requiring multiple transfers, and without delaying the aspiration procedure.

For example, described herein are devices for perfusion of collected blood and clot that include an upper chamber, a lower chamber, a filter element within either the upper chamber and/or the lower chamber, wherein the filter element is configured to capture clot; a vacuum inlet into the upper chamber and configured to couple to a vacuum source; an aspiration inlet into the upper chamber configured to couple to an aspiration line through an aspiration valve; a reperfusion outlet from the lower chamber configured to couple to a reperfusion line (and flow from the reperfusion outlet to the reperfusion line may be controlled through a reperfusion valve); and a vacuum release valve in fluid communication with the upper chamber, wherein the reperfusion valve is configured to be opened when the vacuum release valve is opened. In some examples, the reperfusion valve is configured to be opened only when the vacuum release valve is opened.

Any of these apparatuses may include a fine filter in fluid communication with the reperfusion outlet. The coarse filter may be configured to be manually removed from the upper chamber by opening the top of the upper chamber.

Any of the devices for perfusion of collected blood described herein may include an impermeable partition between the upper chamber and the lower chamber and one or more partition valves configured to form an opening through the impermeable partition. The partition valve may be configured to automatically open (e.g., when the pressure between the upper and lower chambers are normalized to approximately the same pressure and when the weight of the blood in the upper chamber exceeds the cracking pressure of the one or more valve(s). For example, the one or more partition valves may comprise one or more umbrella valves configured to open when a fluid pressure against the valve exceeds a crack pressure. Alternatively, in some examples the apparatus may be configured so that the partition valve(s) are actively controlled to open, e.g., when the system detects a sufficient amount of blood in the upper chamber and when the pressure difference between the upper and lower chambers are approximately normalized (either by detecting the pressure directly within the upper and/or lower chambers or by detecting that a vacuum release valve in the upper chamber is opened. In some examples the apparatus may include a processor that is configured to coordinate the opening of the partition valve and the vacuum release valve.

In any of these examples, the lower chamber may include a pressure regulator opening. In some examples the pressure regulator opening is configured to vent to atmosphere. Alternatively or additionally the lower chamber may be configured to maintain a pressure that is lower than atmosphere pressure e.g., so that the upper chamber and the lower chamber pressure may be normalized quickly, and the upper chamber may maintain some negative pressure (e.g., vacuum) even when transferring blood from the upper to the lower chamber.

In general, the pressure within the lower chamber may be controlled to prevent or minimize foaming and may be configured so that the reperfusion valve will not be opened until the pressure in the lower chamber is approximately at atmospheric pressure.

In any of these apparatuses, the apparatus may be configured so that the blood, and in particularly captured blood clot material, may be directly visualized. For example, the upper and lower chambers may be configured to allow direct visualization of blood through a wall of the upper and lower chamber. In some examples the apparatus may include a separate filtering (coarse filtering) chamber upstream of the upper chamber that is configured (e.g., in a planar configuration) to allow direct visualization of the clot material as it is strained. The filtering chamber may be opened to allow removal of clot material from the coarse filter without disrupting the apparatus.

Any of these apparatuses may include a reperfusion fluid line in fluid communication with the reperfusion outlet through a reperfusion valve. Similarly, any of these apparatuses may include a vacuum source coupled to the vacuum inlet.

In some examples the device for perfusion of collected blood includes separate (partitioned) upper and lower chambers that may each be pressure controlled to allow transfer from the upper chamber to the lower chamber by gravity. The lower chamber may also be configured to allow easy reperfusion of the collected blood back into the patient, either directly or indirectly, including by collecting in a syringe or other container for later reperfusion.

For example, a device for perfusion of collected blood may include: an upper chamber; a lower chamber; an impermeable partition between the upper chamber and the lower chamber; a partition valves configured to form an opening through the impermeable partition; a vacuum inlet into the upper chamber and configured to couple to a vacuum source; an aspiration inlet into the upper chamber; a reperfusion outlet out of the lower chamber; and a pressure regulation opening into the lower chamber configured to maintain the pressure in the lower chamber greater than the pressure in the upper chamber and above the foaming pressure of blood, wherein the partition valve is configured to opened to allow blood to flow from the upper chamber into the lower chamber.

Any of these devices may include a coarse filter in fluid communication with the upper chamber. The coarse filter is configured to have pores sized to restrict the ability of clot to pass through, but may allow blood (including cells, e.g., red blood cells, etc.) to pass through unimpeded. In some examples, the coarse filter may be a mesh, and/or may have pores that are large enough to pass liquid blood readily but small enough to prevent clot material from passing through. In some examples the coarse filter is removable to allow manual clearance of a blood clot.

As mentioned above, in some examples the apparatus includes a clot collection and visualization chamber comprising the coarse filter and that is in fluid communication with the upper chamber through the aspiration inlet.

The pressure regulation opening in the lower chamber may, in some examples, be one or more openings to atmosphere. The opening may be direct or may be covered with a filter to prevent contamination. Alternatively, in some examples the lower chamber may include a connection to the vacuum source (or a second vacuum source) and may maintain the lower chamber at a pressure that is closer to atmosphere pressure than the upper chamber, while still remaining above a pressure that would result in increased foaming. In some examples the pressure regulation opening comprises a valve controllably connecting the lower chamber to a source of negative pressure.

Any of these devices may include one or more pressure sensors, e.g., in the upper and/or lower chambers. Alternatively, in some examples an additional sensor is not included.

The apparatus may include a vacuum release valve in fluid communication with the upper chamber and/or the lower chamber. As mentioned, the one or more partition valves may comprise one or more umbrella valves configured to open when a fluid pressure against the valve exceeds a crack pressure.

In general, the upper and lower chambers may be configured to allow direct visualization of blood through a wall of the upper and lower chamber. The device may include a reperfusion fluid line in fluid communication with the reperfusion outlet through a reperfusion valve. The device may also include a fine filter in fluid communication with the reperfusion line. Any of these devices may include a vacuum source coupled to the vacuum inlet.

For example a device for perfusion of collected blood may include: an upper chamber; a lower chamber; an impermeable partition between the upper chamber and the lower chamber; one or more partition valves configured to form an opening through the impermeable partition; a coarse filter in fluid communication with the upper chamber; a vacuum inlet into the upper chamber and configured to couple to a vacuum source; a vacuum release valve in the upper chamber; an aspiration inlet into the upper chamber; an aspiration valve between the aspiration inlet an aspiration line extending from the aspiration inlet; a reperfusion outlet in the lower chamber and configured to be placed in fluid communication with a reperfusion fluid line by a reperfusion valve; a pressure regulation opening into the lower chamber configured to maintain the pressure in the lower chamber above the pressure of the upper chamber and above the foaming pressure of blood; and a fine filter in fluid communication with the reperfusion line, wherein the one or more partition valves are configured to opened when the vacuum release valve is opened to allow blood to flow from the upper chamber into the lower chamber.

Also described herein are methods of reperfusing blood during a clot removal procedure, the method comprising:

charging an upper chamber of a reperfusion system with a vacuum; opening an aspiration valve and aspirating blood from the patient into the upper chamber through an aspiration inlet into the upper chamber and filtering clot material from the blood using a coarse filter in fluid communication with the upper chamber; collecting the blood from the upper chamber in a lower chamber after filtering the clot material, wherein collecting the blood from the upper chamber in the lower chamber comprises opening a partition valve separating the upper chamber from the lower chamber when the vacuum in the upper chamber is released to approximately the pressure of the lower chamber so that the blood drains from the upper chamber into the lower chamber by gravity; opening a reperfusion valve in fluid communication with the lower chamber after pressure in the lower chamber is at approximately atmosphere pressure; and returning the blood from the lower chamber into the patient's body.

In any of these methods, opening the partition valve may comprise controlling the partition valve to open when the pressure in the upper chamber is approximately the same as the pressure in the lower chamber. In some examples, opening the partition valve may comprise automatically opening the partition valve when the pressure in the upper chamber is approximately the same as the pressure in the lower chamber and the weight of fluid on the partition valve is greater than a crack pressure for the partition valve. Collecting the blood from the upper chamber in the lower chamber may comprise releasing the pressure in the upper chamber by opening a vacuum release valve.

Any of these methods may include filtering the blood with a fine filter before returning the blood from the lower chamber into the patient's body. Any of these methods may include removing the clot material from the coarse filter. Any of these methods may include recharging the upper chamber with vacuum to allow further aspiration after collecting the blood in the lower chamber.

Charging the upper chamber of the reperfusion system with the vacuum may comprise operating a vacuum source coupled to the upper chamber through a vacuum inlet. In some examples, the method may include leaving the vacuum source on continuously while opening the aspiration valve, collecting the blood and opening the reperfusion valve.

For example, a method of re-perfusing blood during a clot removal procedure may include: charging an upper chamber of a reperfusion system with a vacuum; opening an aspiration valve and aspirating blood from the patient into the upper chamber through an aspiration inlet into the upper chamber and filtering clot material from the blood using a coarse filter in fluid communication with the upper chamber; normalizing the pressure between the upper chamber and a lower chamber; opening a partition valve separating the upper and lower chambers so that blood from the upper chamber flows into the lower chamber; re-charging the upper chamber with the vacuum to allow further aspiration; opening a reperfusion valve in fluid communication with the lower chamber; and returning the blood from the lower chamber into the patient's body.

The lower chamber may be maintained at atmosphere pressure. The lower chamber may be maintained at a pressure between atmosphere and a foaming pressure of blood (e.g., about 600 mm Hg). Any of these methods may include removing the clot material from the coarse filter.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 1 shows one example of a suction catheter as described herein.

FIG. 2A shows a transparent view of one example of a distal end region of a suction catheter such as the catheter shown in FIG. 2A.

FIG. 2B shows the distal end region of the suction catheter of FIG. 2A in a non-transparent view.

FIGS. 6A-6E illustrate examples of distal end regions of suction catheter devices. FIG. 6A shows an example of a distal end region including a single cushioning flow opening. FIG. 6B shows an example with two cushioning flow openings positioned distally of the lateral midline of the aspiration opening. FIG. 6C shows an example with two cushioning flow openings positioned approximately at the lateral midline of the aspiration opening. FIG. 6D shows an example with the open distal end acting as the only cushioning flow opening. FIG. 6E shows an example of a distal end region including four cushioning flow openings on either side of an internal guide channel (into which a diagnostic guide catheter may be positioned).

FIGS. 7A-7E illustrate examples of distal end regions of suction catheters as described herein, including cushioning flow openings of different dimensions, number and positions.

FIG. 8A-8C show examples of distal end regions of suction catheters including flow openings that are not configured appropriately to operate as cushioning flow openings. In both FIG. 8A (single opening, located proximally from the longitudinal center of the aspiration opening) and FIG. 8B (openings on the same lateral side as the aspiration opening, located proximal to the aspiration opening) the resulting flow failed to impart a rotational force on the clot material. In FIG. 8C, two openings positioned at approximately the longitudinal center of the aspiration opening, radially offset by about 90 degrees from the lateral midline of the aspiration opening failed approximately 50% of the time.

FIGS. 9A-9E show examples of distal end regions including openings tested to determine the appropriate longitudinal position of the openings, showing the time required to aspirate the tissue.

FIGS. 10A-10C illustrate examples of different distal end regions including cushioning flow openings having different size openings (surface areas).

FIG. 16 shows a distal end region of an example of a suction catheter including cushioning flow openings and a shroud region to offset the cushioning flow openings from the wall of the lumen and/or clot material within the lumen in use.

FIG. 17 schematically illustrates an example of a suction catheter including a displacement projection extending from an outer surface of the distal end region that is configured to displace the outer openings of the cushioning flow openings from a wall of a vessel. FIG. 17A is a graph showing the change in pressure over time using a catheter such as the one shown in FIG. 17.

FIG. 18 schematically illustrates an example of a suction catheter including a mechanical repositioner.

FIGS. 21A and 21B schematically illustrate a tip including cushioning valve openings that are configured to have an outlet opposite (and at least one outlet distal to) a longitudinal midline of the aspiration opening and to apply a cushioning flow from a proximal fluid source (e.g., an external fluid source).

FIG. 21C schematically illustrates an example of an apparatus using the cushioning flow openings configured as shown in FIGS. 21A and 21B.

FIG. 22 schematically illustrates a method of removing clot material using a suction catheter apparatus as described herein including cushioning flow openings.

FIG. 23A illustrates a section through the distal end region of an example of a suction catheter transverse to the long axis, showing a region of cushioning flow below the aspiration opening.

FIGS. 24B1 and 24B2 show side and end facing views of a suction catheter as described herein.

FIGS. 24C1 and 24C2 show side and end facing views of a suction catheter as described herein.

FIGS. 24D1 and 24D2 show side and end facing views of a suction catheter as described herein.

FIG. 28A is schematic illustration of the catheter shown in FIG. 28B, with a portion of the distal end cut away to show the internal detail.

FIGS. 33A-33E illustrate one example of a method of operating a device for collection and/or reperfusion of blood into a patient such as the device shown in FIG. 32.

FIG. 34 schematically illustrates one example of a device for collecting and/or perfusion of blood, e.g., during a clot capture procedure, including a partition valve.

FIGS. 35A-35B illustrate the operation of one example of a partition valve (shown as an umbrella valve in this example).

FIGS. 36A-36E illustrate one example of a method of operating a device for collection and/or reperfusion of blood into a patient such as the device shown in FIG. 34.

FIG. 37 schematically illustrates an example of a device for collecting and/or perfusion of blood, e.g., during a clot capture procedure.

FIG. 38 schematically illustrates an example of a method of reperfusing blood during a clot removal procedure.

DETAILED DESCRIPTION

Figure 3A:
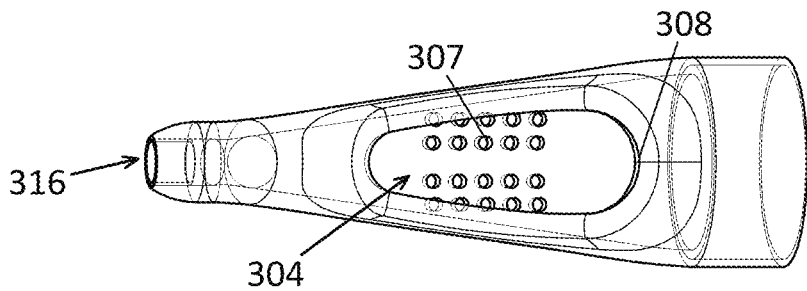
FIG. 3A is a top view of another example of a distal end region of a suction catheter.

The aspiration methods and apparatuses described herein may include aspiration catheters as well as reperfusion devices. These devices may be used together (e.g., as part of the same system) or separately.

In general, the aspiration catheters (also referred to equivalently as suction catheters) described herein are configured for removing clot material from a patient. These aspiration catheters may be configured to remove clot in longer strips, which may prevent or reduce the risk of releasing smaller clot fragments back into the vessel. Longer strips may also allow post procedure analysis, including more accurate determination of the amount of clot removed and the character of the clot. The aspiration catheters described herein may also be configured to prevent blocking of the catheter by the clot, which may occur when the size of the clot material is larger than the aspiration opening into the aspiration catheter, as is often the case. This sort of clotting is often referred to as "lollypoping." The aspiration catheters described herein may use one or more cushioning flow openings to impart a rotational force on the clot at the aspiration opening; in some cases this may rotate or flip the clot material relative to the aspiration opening, driving the clot material against the proximal edge of the aspiration opening. The cushioning flow openings may also generate an entraining flow of fluid (e.g., blood) within the aspiration lumen of the catheter, drawing the cut strips of clot material into the aspiration lumen. In addition, these aspiration catheters may be configured to remove clot more quickly and may remove less blood from the patient.

In general, the apparatuses (e.g., devices and systems, including aspiration catheters) described herein may include a laterally positioned aspiration opening that may be on a tapered side of the distal end region of the catheter. The tapered shape may aid the device in navigating the lumen of a vessel. The distal end region (sometimes referred herein as the distal tip region or simply distal tip) may be formed of a generally soft material. In some examples the catheter may include one or more lumen. At least one lumen may be configured as a suction (or aspiration lumen) that is in communication with the aspiration opening. In some examples the aspiration catheter may also include a second lumen, which may be referred to as a guide lumen or a diagnostic catheter lumen, which may extend distally past the aspiration opening. The guide lumen may be configured to allow passage of a guidewire, guide catheter, diagnostic catheter, etc. The guide lumen may be open into the aspiration lumen. In some examples the guide lumen is at least partially open into the aspiration lumen so that when an additional elongate member (e.g., guidewire, guide catheter, diagnostic catheter, etc.) is not present in the guide lumen, fluid may pass from outside of the catheter through the distal end opening and into the aspiration lumen.

Any of the apparatuses described herein may include one or more cushioning flow openings that are configured to prevent clogging and to drive the clot material against the proximal edge of the aspiration opening. In some examples, the cushioning flow openings may be configured to generate a rotational force on the clot material at the aspiration opening, which may assist in preventing clogging and/or cutting strips of clot material so that it may become entrained down the lumen. As describe in detail herein. The cushioning flow openings may be configured in this manner based on one or more of: longitudinal position relative to the aspiration opening, radial position relative to the aspiration opening, number of openings, and/or aggregate size of openings relative to the size of the aspiration opening.

A common issue with many venous thrombectomy catheters that use aspiration to remove blood clots from the pulmonary arteries is the clot blocks the distal end of the catheters causing a lollipop effect. The catheter then needs to be removed from the patient and declogged during the procedure before the device can remove the rest of the clot in the patient. This tends to happen when the blood clots are larger than the aspiration lumen of the catheter through which they are to be removed. If the catheter is not sufficiently sharp enough to core the blood clot the clot gets wedged in the distal end of the catheter. Once the distal aspiration opening of the catheter gets clogged the flowrate tends to zero and the dynamic interaction (coring) between the clot and the tip of the clot is stalled. Although in some cases the catheter (e.g., the aspiration opening) may be made sharp enough to allow for coring of the clot; however, this sharpness can cause other issues, and may result in vessel trauma or perforation. The aspirations catheters described herein including one or more cushioning flow openings may provide efficient clot aspiration and/or shearing while ensuring the tip and clot orifice are atraumatic. The aspiration catheters described herein may include a distal end regio of the catheter that, in conjunction with the configuration of the one or more cushioning flow openings, may bias the clot material to a proximal edge region of the aspiration opening where the shearing may occur while not blocking the flowrate of the catheter.

The distal tip region may also be configured for use as an integrated dilator and atraumatic tip allowing the user to advance the aspiration catheter from the right femoral vein across the heart and into the pulmonary arteries. It may also allow the user to move the catheter and aspirate at the same time if desired.

FIG. 1 illustrates one example of an aspiration ("suction") catheter as descried herein. In any of the apparatuses described herein the distal tip region 118 of the aspiration catheter 100 is configured to be atraumatic, and may taper from a distal to proximal direction, which may ease insertion and advancement through vessels and across the heart. The distal end region 118 extends from the distal end of the elongate catheter body 110. The distal end region 118 of the aspiration (suction) catheter may have an aspiration opening 104 on a lateral side. The aspiration catheter may also include a distal opening 105 into a guide lumen. In some examples the lumen and distal opening may be sufficient to allow a 4 Fr catheter to advance and rotate through the lumen and the 4 Fr catheter can ride over a guidewire during a procedure. In the example shown in FIG. 1 a diagnostic catheter 106 is shown extending distally from the guide lumen and out of the distal opening 105; a guidewire 111 extend from out of the lumen of the diagnostic catheter 106.

The distal end region (e.g., "tip") 118 may be made from an elastomer (e.g., 55D TPU) that is soft enough to track through the heart without causing vessel damage while have sufficient stiffness to resist collapse under full vacuum. In some examples the distal end region may be made with more flexible materials and a stiffening member may be used to add hoop strength in the area of the aspiration opening 104. This is illustrated in FIG. 2A, which shows an example of a distal end region 218 that includes a hoop strength support 212. This hoop strength support 212 could be a stainless steel stiffening member such as a partial ring or a stiffer plastic overmolded section.

In FIGS. 2A and 2B, the tip 218 has an aspiration opening 204 on its slanted (tapered) face through which clot can be aspirated. This opening is elongated along the long axis of the catheter (the longitudinal axis) and is wider at the more proximal end than at the more distal end. Either the entire edge of the aspiration opening 204 or just the proximal edge 208 of the opening may be configured to have additional raised material around it to help with withstanding collapse under vacuum. This raised region may be configured as a lip 220 (which may be referred to as a reinforced lip, that is reinforced by including additional material, and/or may be reinforced by including a stronger and/or stiffer material). These design elements may allow the aspiration opening to create a shearing quadrant (proximal edge 208) through which the clot can be sheared against when vacuum is turned on. This proximal edge region is highlighted in FIG. 2B, and may be where the majority of clot shearing occurs. As will be described in more detail the one or more cushioning flow openings as well as the tip shape may result in flow dynamics for the tip that drive the clot material against this proximal edge region during aspiration.

In FIGS. 2A and 2B, the distal end region 218 may also include a distal opening 205 as described above. The distal end region 218 may also include one or more cushioning flow openings 214.

The aspiration opening may generally be shaped to create relatively high-velocity flow across the proximal edge of the tip. During aspiration, the tip opening which is wider at the more proximal edge ("proximal quadrant") and substantially wider than the distal quadrant, may allow a higher velocity of flow to occur across this proximal edge region of the opening. For example, FIG. 3A shows a top view, looking down at the aspiration opening 304, of an example of a tip as described herein. In this example, the tip region includes a distal opening 316 that opens into both the aspiration lumen and a guide lumen. An array of cushioning flow openings 307 are located radially opposite from the aspiration opening 304. The proximal edge 308 (or proximal quadrant) is indicated.

Figure 3B:
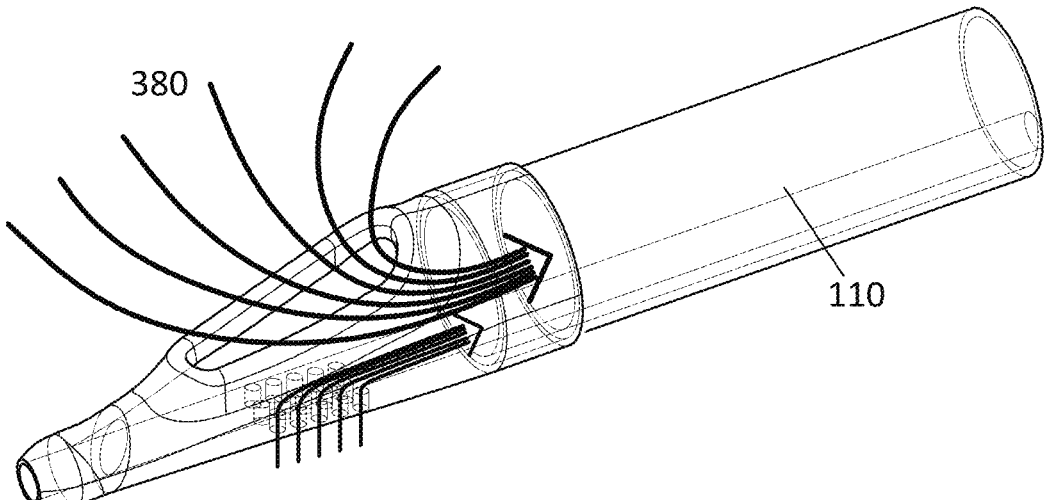
FIG. 3B is a perspective view of a distal end region of a suction catheter, showing flow lines into the suction catheter when aspiration is applied.
Figure 3C:
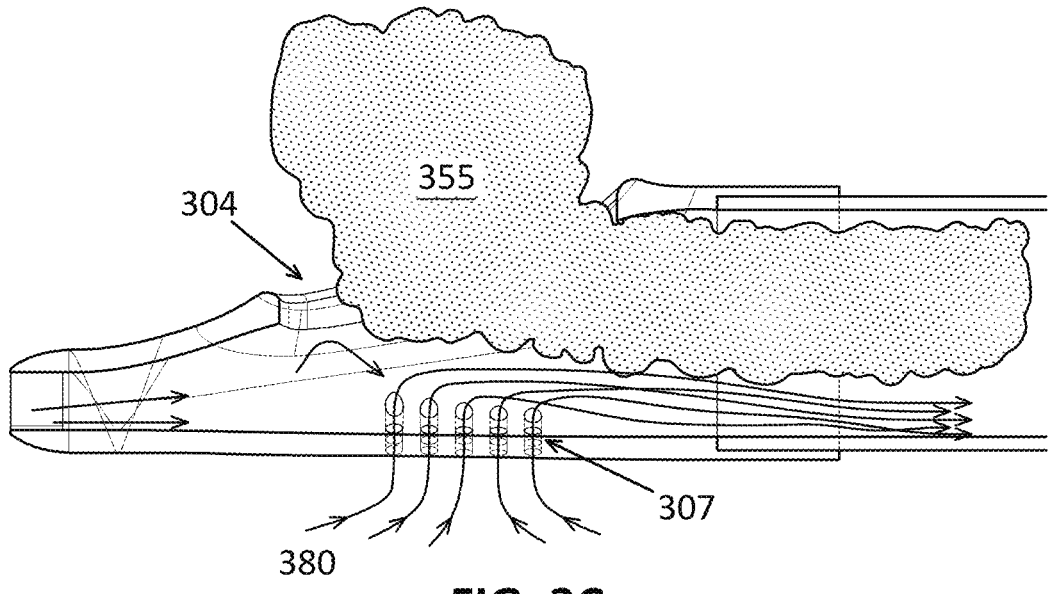
FIG. 3C is a side sectional view of the suction catheter shown in FIG. 3B.

These shape of the aspiration opening, in combination with the location, shape and size of the cushioning flow openings may increases the force on the clot at the proximal edge of the aspiration opening, as illustrated by the flow lines shown in FIG. 3B. The cushioning flow openings may be positioned to help maintain a high flow rate in the device as the clot approaches the aspiration opening, and may keep the clot biased towards the shearing proximal edge of the aspiration opening. In this example, the small cushioning flow openings are positioned on an opposite side of the tip relative to the orifice (e.g., radially offset from the longitudinal midline of the aspiration opening) so that when the flow rate begins to drop through the aspiration opening as clot begins to occlude it, the cushioning flow openings ay increase in flowrate to impart a rotational force on the clot, rotating and/or flipping the clot relative to the aspiration opening and helping to ensure the clot material stays moving and is cut against the proximal edge. This may prevent the flowrate through the catheter from stalling, and may prevent clogging of the catheter, even as long strips of clot are removed. The cushioning flow openings create a "flow cushion" to ensure that the catheter does not clog and there is a continuous flow through and into the catheter. This is also illustrated in FIG. 3C, showing that clot material 355 is driven against the proximal edge 308 of the aspiration opening 307. Flow 380 from the cushioning flow openings 307 may combine with flow from the aspiration opening 304 to impart a rotational force on the clot material 355.

For example, during aspiration when no clot is in proximity to the aspiration opening, the majority of the flow may occur through the orifice and the cushioning flow openings may provide relatively little flow into the aspiration catheter. As the clot material approaches the distal end region of the catheter and is drawn to the aspiration opening, the flow through the cushioning flow openings may begin to increase, creating a fluid cushion which will drive the clot against the proximal edge of the aspiration opening of the tip and maintain a flowrate in the aspiration catheter so that a continuous flowrate moves in the lumen of the catheter to transport the clot proximally towards a collection chamber.

The cushioning flow openings can be configured to be positioned somewhat distal to the proximal edge of the aspiration opening (and in some examples at least one opening may be distal to a longitudinal midline of the aspiration opening) and can be in multiple locations, have different shapes or positions. Example of cushioning flow opening positions and sizes that work are below. The cushioning flow openings may generally create a "flow pillow" distributing the flow across a larger area. Thus, the cushioning flow openings may have an optimal size, number and location to maintain the flowrate through the aspiration opening, without negatively impacting clot engagement.

Figure 4A:
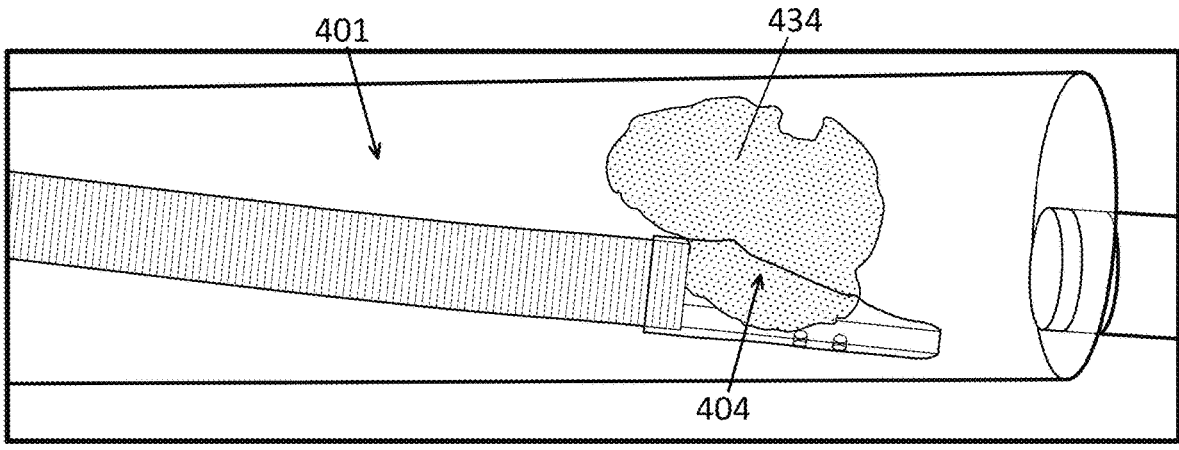
FIG. 4A illustrates a suction catheter without cushioning flow openings, showing clogging ("lollypoping") of clot material at the aspiration opening on the lateral side of the suction catheter.

For example, FIG. 4A shows an example of a catheter 401 having an aspiration opening on a lateral side of the distal end region that does not include any cushioning flow openings. In FIG. 4A a clot material 434 that has become jammed ("lollypopped") onto the aspiration opening 404.

Figure 4B:
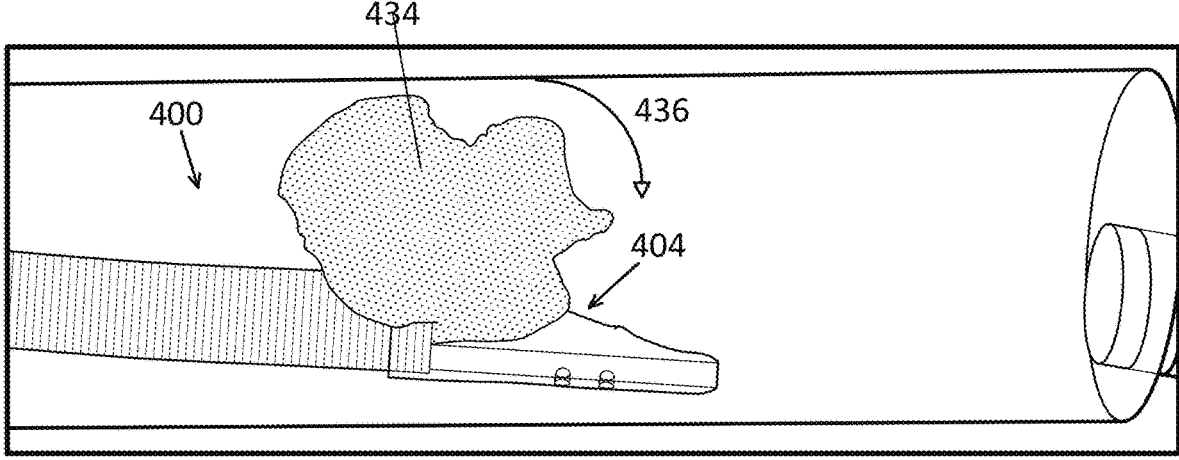
FIGS. 4B-4C illustrate the effect of cushioning flow openings on the clot aspiration, showing the application of a rotational force on the clot material so that it is driven against the proximal opening edge of the aspiration opening, forming long strips of clot that are moved into the suction lumen for removal from the body.
Figure 4C:
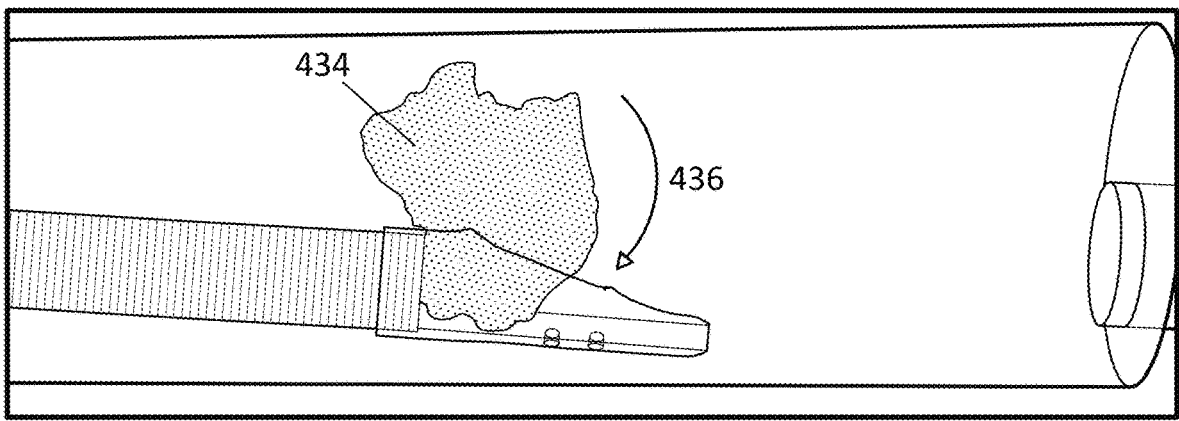

FIGS. 4B and 4C illustrate an example of an aspiration catheter 400 including a plurality of cushioning flow openings as described herein. These cushioning flow openings allow for continuous flow as a clot approaches the tip, imparts a rotational force 436 on the clot 434, and create a cushion of flow to ensure the clot does not lollipop on the end of the aspiration catheter 400. As shown, the clot material is driven by the aspiration flow from both the aspiration opening and the cushioning flow openings so that the clot material 434 is rotated against the proximal edge of the aspiration opening to shear and cut a strip of clot material that is then entrained by the flow into the aspiration lumen without clogging.

Figures 5A, 5B, 5C, 5D, 5E, 5F, 5G:
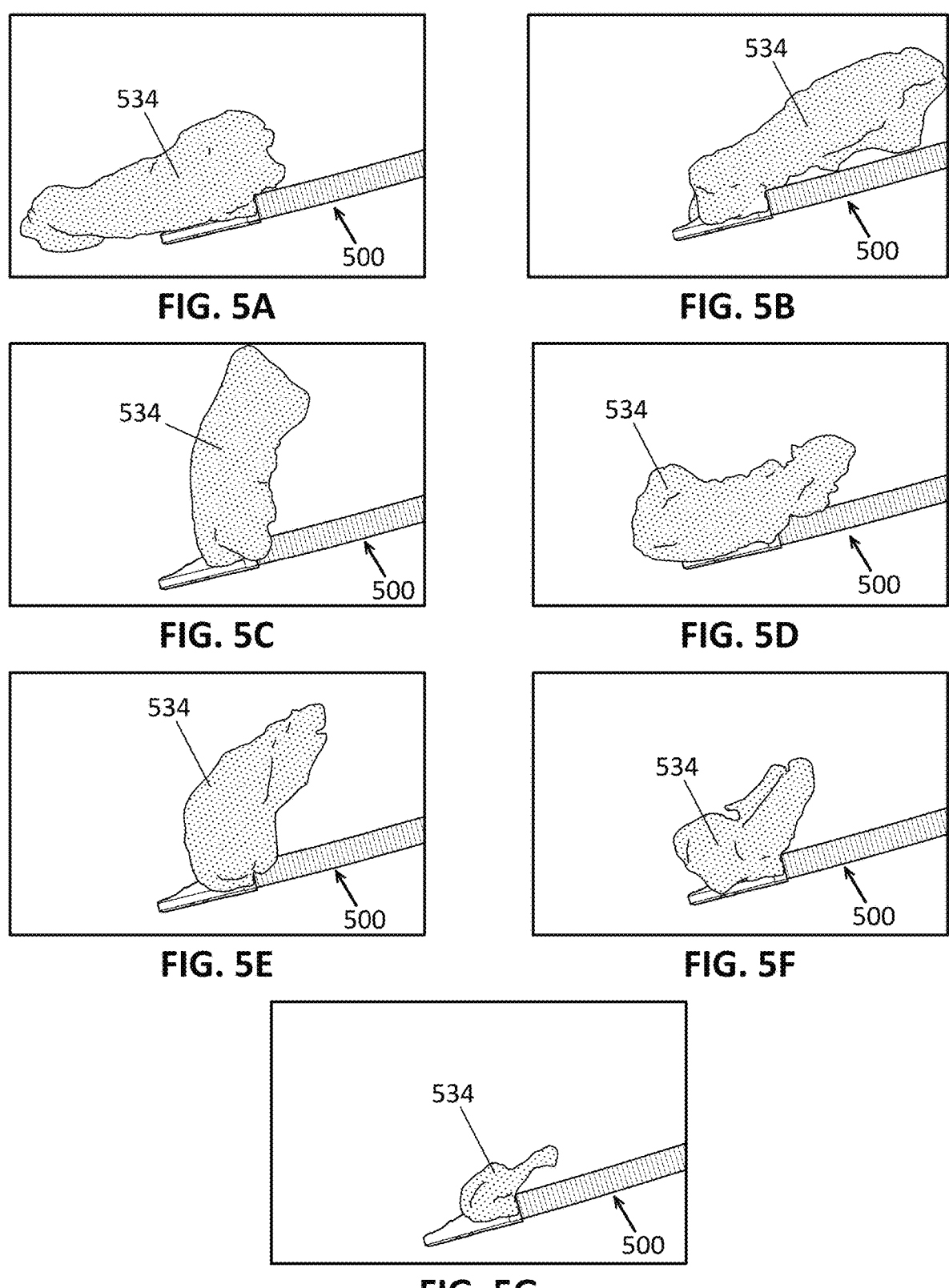
FIGS. 5A-5G illustrates the removal of a clot model using an example of a suction catheter including cushioning flow openings as described herein. A rotational force is applied to the clot through the aspiration lumen based on the configuration of the cushioning flow openings, resulting in the clot being driven against the proximal edge region of the aspiration opening including rotating (and flipping) the clot to allow cutting of strips of the clot model material.

FIGS. 5A-5G illustrates another example of a model clot material 534 that is rotated and flipped as it is driven against the proximal edge of the aspiration opening when aspiration is applied through the aspiration lumen of the suction catheter 500 having a plurality of cushioning flow openings. FIGS. 5A-5G show the movement of the clot material as it is rotated against the proximal edge of the aspiration opening. In FIG. 5A when the aspiration opening is sufficiently close to the clot material so that the clot material is drawn to aspiration opening. The flow of fluid (e.g., blood) into the catheter 500 from the cushioning flow openings causes the clot material to be pulled proximally against the proximal edge of the aspiration opening so that the clot material is moved proximally relative to the distal tip region, as shown in FIG. 5B. The flow from the aspiration lumen and the cushioning flow openings causes the clot material 534 to flip relative to the aspiration opening, as shown in FIGS. 5C and 5D. As the clot material is rotated (e.g., flipped) relative to the aspiration opening, it continues to be drive against the proximal edge of the aspiration opening so that a strip (or strips) of material is cut off and pulled into the aspiration lumen of the catheter 500, as shown in FIGS. 5E-5G, until all of the clot material is removed.

As mentioned above, the configuration of one or more parameters of the openings may allow these openings to function as described in FIGS. 4B-4C and 5A-5G so that they act as cushioning flow openings. These parameters may be optimized so that the cushioning flow openings apply the appropriate rotational force to the clot material adjacent to the aspiration opening and so that the removal of clot material is sufficiently rapid (e.g., so that the time to aspirate the clot is below a target level, which may minimize blood loss and procedure time). These parameters of the cushioning flow openings may include the longitudinal (e.g., axial) position of the one or more cushioning flow openings relative to the aspiration opening, the radial position of the cushioning flow openings relative to the aspiration opening, the aggregate size of all of the openings of the cushioning flow openings relative to the size of the aspiration opening, and the number of openings. For example, the one or more cushioning flow openings may generally be positioned so that they are distal to the distal edge region of the aspiration opening, and more specifically at least one of the cushioning flow openings should be distal to a longitudinal midline of the aspiration opening and/or so that the average longitudinal position of the cushioning flow openings is at or distal to the midline of the aspiration opening. In addition, the cushioning flow openings may be poisoned radially (relative to the aspiration opening) so that the cushioning flow openings are radially offset from the longitudinal midline of the aspiration opening by more than 90 degrees (e.g., more than 100 degrees, more than 110 degrees, more than 120 degrees, between 90-180 degrees, between 100-180 degrees, etc.). The angle of the cushioning flow openings relative to the midline of the aspiration opening may be measured from the middle of the cushioning flow opening.

In general, the relative size of the aspiration opening to the sum of the size of the cushioning flow openings may be between about 10:1 and 18:1 (e.g., between about 11:10 and 17:1, between about 10:1 and 16:1, between about 12:1 and 16:1, between about 12:1 and 14:1, etc.). In general, cushioning flow openings that are too large do not work. In general, the vacuum applied may be more than about 510 mmHg (e.g., the difference between the pressure in the vessel and the pressure in the aspiration lumen may be greater than 250 mmHg).

FIGS. 6A-6E illustrate examples of distal end regions (tips) that include cushioning flow openings. FIG. 6A shows a first example of a tip having a single cushioning flow opening 614 that is positioned distally to the midline 644 of the aspiration opening 604. In FIG. 6A the cushioning flow opening is blocked by a diagnostic catheter 606 that is extending through a guide lumen. Thus, the cushioning flow opening may be opened or closed by inserting or removing the diagnostic catheter. The cushioning flow opening may pass through the guide lumen to allow fluid from outside of the tip to pass into the aspiration lumen when the diagnostic catheter is not covering the cushioning flow opening. In some examples, as shown in FIGS. 6B and 6C, the cushioning flow openings are radially offset from the guide channel (and any diagnostic catheter that may be present). In FIG. 6B two cushioning flow openings 614, 614' are positioned distal to the midline 644 of the aspiration opening 604. In FIG. 6C the cushioning flow openings 614, 614' are positioned distal at the midline 644 of the aspiration opening 604.

In any of these suction catheters described herein the cushioning flow opening may be a distal opening 616, as shown in FIG. 6D. In this example the only cushioning flow opening is the distal end opening; in some examples lateral cushioning flow openings may also be included opposite from the aspiration opening.

FIG. 6E illustrates an example a perspective view of a tip having four cushioning flow openings, all positioned at or distal to the midline of the aspiration opening and all radially offset from a longitudinal midline of the aspiration opening by about 160 degrees, so that they are not occluded by the presence of a diagnostic catheter 606, as shown.

The cushioning flow openings in FIGS. 6A-6E are all circular openings. In some examples the cushioning flow openings maybe other shapes, including oval, rectangular, triangular, etc. In additional the cushioning flow openings described herein are primarily directly formed though the wall of the tip (and/or any guide lumen). In some examples the cushioning flow openings may have an output that opens into the aspiration lumen at the position indicated above (e.g., typically distal to the proximal opening and in particular, at or distal to the longitudinal midline of the aspiration opening), while the input into the cushioning flow openings may be more proximally located, including extending (e.g., through a cushioning flow channel) to the proximal end of the apparatus, or to a more proximal region of the catheter. A cushioning flow channel may be preferred where, for example, the flow from the cushioning flow openings is positively applied, rather than just being applied by the applied aspiration from the aspiration lumen.

FIGS. 7A-7E illustrate examples of cushioning flow openings having different locations, positions, numbers and shapes. In general, the parameters of the cushioning flow openings may be chosen in order to minimize blood loss and to minimize the time required to remove the clot from the vessel. FIG. 7A shows an example of a tip having two cushioning flow openings 714 located at approximately the midline of the aspiration opening (similar to FIG. 6C), in which the openings are each about 1 mm in diameter. FIG. 7B shows an example in which the cushioning flow openings 714 are elongated slots of dimension 0.7 mm×8 mm. FIG. 7C shows an example of an array of 9 cushioning flow openings (3×3) 714 positioned distal to the midline of the aspiration opening. Each cushioning flow opening has a diameter of 0.7 mm. FIG. 7D shows an example of a tip having an array of 20 cushioning flow openings (4×5) 714, each about 0.5 mm in diameter. Finally FIG. 7E shows an example of a tip similar to FIG. 6B having two cushioning flow openings 714 each about 1 mm diameter, positioned distal to the midline of the aspiration opening. The tips shown in FIGS. 7A-7E were examined, as described below, to determine characteristics of the cushioning flow openings that optimally remove clot material with minimum blood loss.

FIGS. 8A-8C show examples of tips having openings 817 that did not operate as cushioning flow openings generating a rotational force and cushioning flow as described herein. In FIG. 8A, the tip includes a very large opening 817 and was unable to induce a rotational force or cushioning flow. Similarly FIG. 8B shows a tip with two smaller openings 817 positioned proximal to the aspiration opening (in FIG. 8B the openings are also positioned on the same radial location as the aspiration opening, similar results were seen with opening located radially offset from the aspiration opening) that was also unable to generate a rotational force and cushioning flow. Both the tips of FIGS. 8A-8B were unable to remove clot quickly and prevent lollipopping. The tip shown in FIG. 8C resulting in an intermediate success rate, clogging (e.g., lollypopping) approximately 50% of the time. In this example, the openings 817 are positioned at the midline (e.g., the longitudinal midline) of the aspiration opening and are radially offset from the long axis (longitudinal axis) of the aspiration opening by 90 degrees.

In general, the cushioning flow openings should be positioned distal to the aspiration opening. As shown in FIGS. 9A-9E there was a dramatic increase in the effectiveness of the cushioning flow openings to prevent clogging and to remove strips of clot material when the cushioning flow openings were positioned at/or distal to the midline (e.g., center 944) of the aspiration opening. The tips shown in FIGS. 9A-9E were examined using a model clot material under identical conditions to estimate the time required to remove clot material (time to aspirate), as shown. In this example, for the tips shown, the results indicated that generally, the more central the cushioning flow openings were to the center of the opening 944, the faster the clot material was removed. In addition, the more distal examples were able to generate a more rotational force on the clot material, preventing clogging and allowing removal of longer strips of clot material.

FIGS. 10A-10C illustrate tips having different relative opening sizes for the cushioning flow openings (relative to the aspiration opening). In FIG. 10A, the opening is a single hole of diameter 4 mm (similar to that shown in FIG. 8A), and the area of hole is approximately 12.57 mm$^2$. In each of FIGS. 10A-10C the aspiration opening has an area of about 35.63 mm$^2$. The ratio of the aspiration opening to the additional (e.g., cushioning flow opening) in FIG. 10A is approximately 2.83:1 (so the additional opening is approximately 35.3% of the aspiration opening area). In FIG. 10B, an array of 9 openings were tested, each opening of a diameter of 0.5 mm, having a total open area for the additional openings (e.g., cushioning flow openings) of approximately 1.76 mm$^2$. Thus, the ratio of the aspiration opening to the additional (e.g., cushioning flow opening) in FIG. 10B is approximately 20:1, and the additional opening(s) area is approximately 4.9% of the aspiration opening area. In FIG. 10C, two openings were tested, each opening of diameter 1 mm, having an open area for the additional openings (e.g., cushioning flow openings) of approximately 1.57 mm$^2$. Thus, the ratio of the aspiration opening to the additional (e.g., cushioning flow opening) in FIG. 10C is approximately 23:1, and the additional opening(s) area is approximately 4.4% of the aspiration opening area. The tip shown in FIG. 10A did not work, while the openings of the tips shown in FIGS. 10B and 10C did operate as cushioning flow openings.

Figures 11, 12, 13:
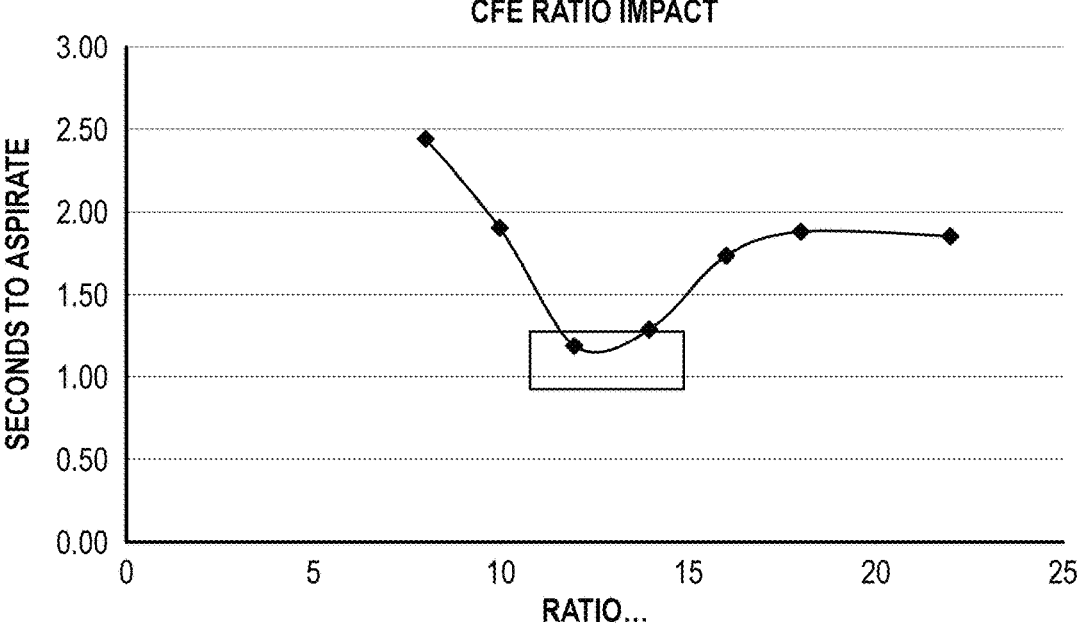
FIG. 11 is a table illustrating different relative size openings of cushioning flow openings as compared to the size of the aspiration opening (e.g., the ratio of cushioning flow openings aggregate area to aspiration).
FIG. 12 is a table illustrating the results of tests of different relative size openings of cushioning flow openings as compared to the size of the aspiration opening from Table 11 on aspiration flow rate to capture the clot material.
FIG. 13 is a graph of the data shown in FIG. 12.
Figures 14A, 14B, 14C, 14D:
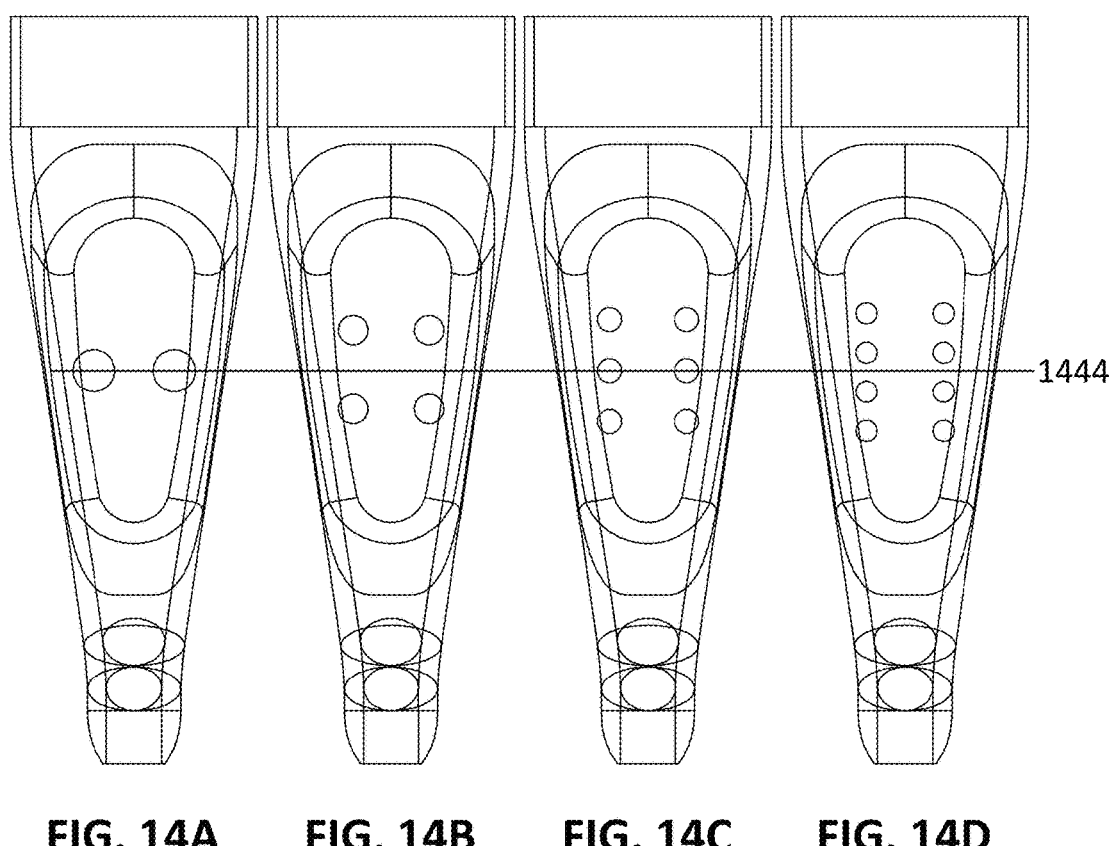
FIGS. 14A-14D illustrate examples of different distal end regions of suction catheters having different numbers of cushioning flow openings (all normalized to the same total open area).

The effect of the size of the cushioning flow opening(s) on the ability of the tips to provide a rotational force, prevent clogging, and rapidly remove strips of clot material was examined for a variety of different cushioning flow opening sizes. The table of FIG. 11 illustrates examples of tips having cushioning flow opening area ratios relative to the opening area of the aspiration opening. In FIG. 11, ratios of aspiration opening size to cushioning flow opening size of between 8 and 22 are listed, showing the corresponding hole diameters and areas. These tips were examined in multiple trials and the time to remove clot (with no clogging) was measured, as shown in FIGS. 12 and 13. FIG. 13 graphically illustrates the results shown in the table of FIG. 12. In these tests, a model clot material (e.g., 10 cc of Flarp) was used in a vessel diameter of 22 mm. A vacuum of 740 mmHg was applied and clot capture was recorded through video and analyzed frame by frame.

When considering just the time to aspirate the full clot, the ratio of the aspiration opening area to the cushioning flow opening area (total) shows an optimal range of between about 10:1 and 18:1 (e.g., between about 11:1 and 17:1, between about 10:1 and 16:1, between about 12:1 and 15:1, between about 12:1 and 14:1, etc.).

Figure 15:
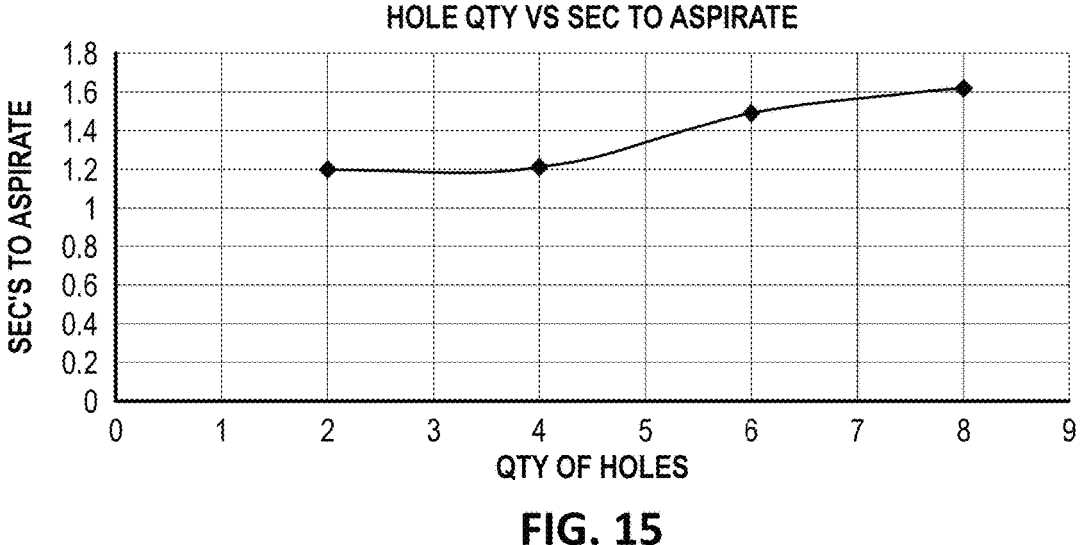
FIG. 15 is a graph showing the effect of the different number of cushioning flow openings on the time to aspiration a clot model, using the distal end regions shown in FIGS. 14A-14B.

Similar experiments were performed to determine an optimal number of holes to be used. In this set of experiments, the ratio of aspiration opening area to cushioning flow opening area was maintained at 12:1 with the number of holes varied between 2 and 8, and the holes were symmetrically distributed around the midline 1444 of the aspiration opening, as shown in FIGS. 14A-14D. The results are shown graphically in FIG. 15, showing that the time to aspiration equivalent clots was approximately the same for between 2-4 cushioning flow openings. After four, the increased slightly as each additional pair of holes was added. The number of holes may be greater than 8. In some examples, between 1 and 26 holes may be used (e.g., between 1-20, between 2-20, etc.).

Any of the apparatuses described herein may be configured to prevent clot material and/or vessel wall material from occluding the cushioning flow openings. For example, any of these apparatuses may include an extension (e.g., shroud) extending from the outer surface of the elongated body to prevent the cushioning flow openings from becoming blocked. In some cases, the extension is a projection extending opposite from the aspiration opening that is somewhat distal to the cushioning flow openings to prevent clot material from entering the cushioning flow openings and/or prevent luminal wall from covering (and blocking) the cushioning flow openings.

For example, FIG. 16 shows an example of a projection or shroud 1662, forming a distal-facing wall around the cushioning flow openings 1614. In this example the projection is a T-shaped projection, extending proud of the outer surface of the tip, which may allow space from the vessel (luminal) wall, and may block clot material from extending and covering the openings.

In some examples, the cushioning flow openings may include a distal opening (e.g., the distal tip opening from which a diagnostic catheter may exit. Other examples may include the use of a membrane/mesh/filter material over the cushioning flow openings.

Thus, in any of these examples one or more raised protrusion within the tip could also create an area under the clot through which the flow could pass to keep the clot moving. In some examples the raised protrusion could be outer surface of the guide lumen (e.g., the tube that a navigation catheter/diagnostic catheter) passed thru. Alternatively, as shown in FIG. 16, the protrusion may be formed by one or more features built into the tip itself.

Thus, the holes (the cushioning flow openings) may be kept from clogging by including a raised barrier on an outside of the tip, which may create a mechanical stop to
keep the clot away from clogging the holes. These clot
barriers could be passive (e.g., rigid) or active (e.g., expand-
able, such as balloon or spring-based members that may be
controllably expended and/or retracted from the proximal
end of the apparatus).

Any of these suction catheters may include a mechanical
method for creating a continues flow instead of or in addition
to the cushioning flow openings described herein. For
example, FIG. 17 shows an example of a catheter 1700
including an additional pressure source (e.g., a bellows
1717) at the proximal end of the catheter which could
rapidly increase and decrease the vacuum level in the shaft
to create a turbulent flow to ensure the catheter does not get
clogged by a clot 1734 jammed to the end of the catheter,
e.g., by applying a force (F) to pump the bellows and alter
the pressure within the aspiration lumen (as shown by the
inset graph 17A).

Alternatively or additionally, FIG. 18 shows another
example of a catheter 1800 with a mechanical linkage
system with distal member (e.g., a mechanical repositioner
1881) that could reposition the clot 1834 mechanically
(rather than just by flow) to prevent blocking of the aspira-
tion opening and ensure continuous flow.

Figure 19A:
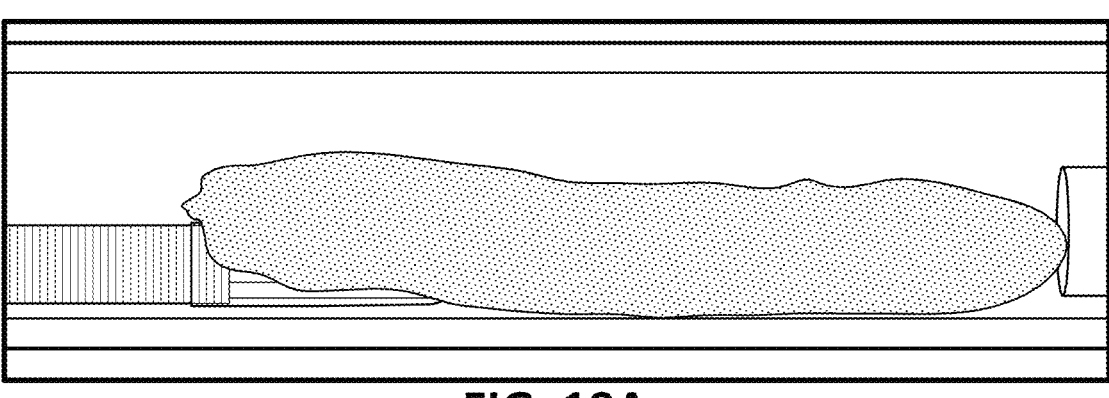
FIGS. 19A-19D illustrate an example of a suction catheter as described herein including cushioning flow openings operating on clot material.
Figure 19B:
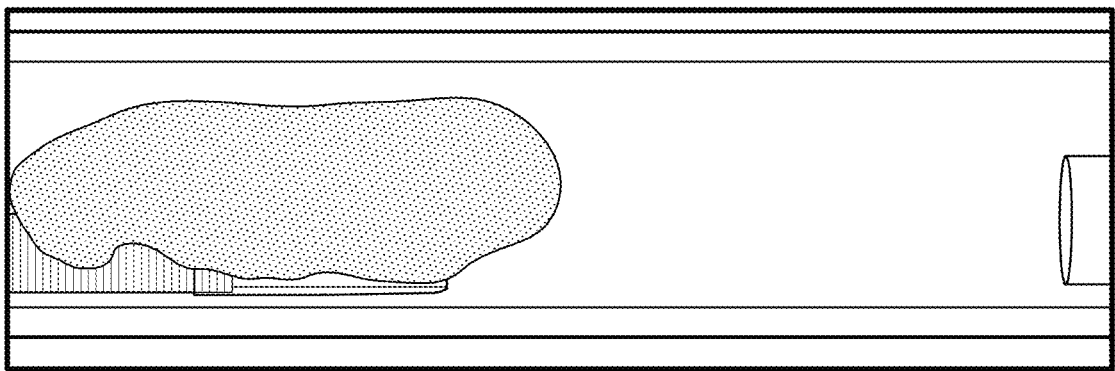
Figure 19C:
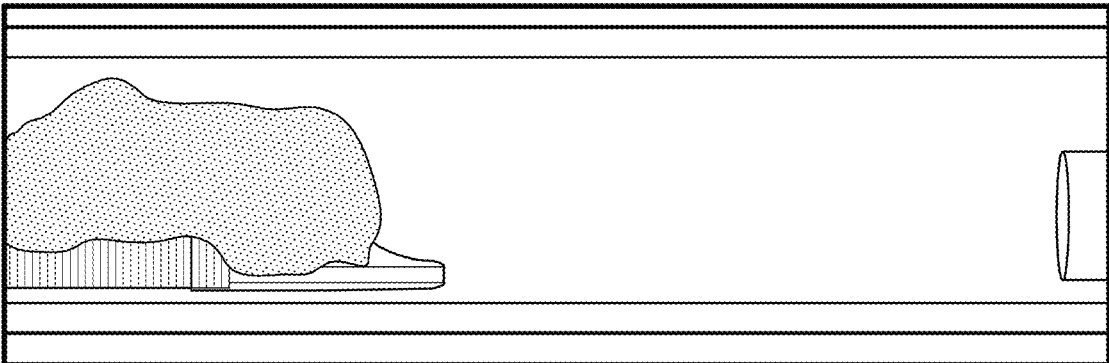
Figure 19D:
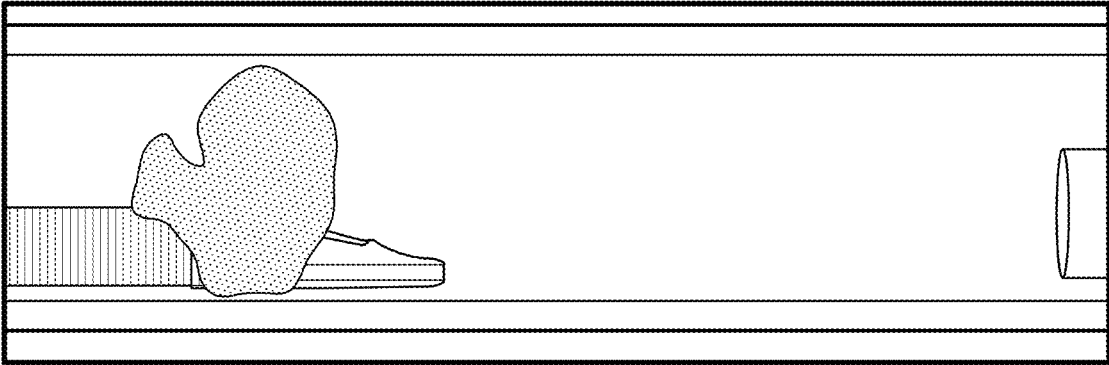

In practice, the apparatuses described herein including the
cushioning flow openings configured as described above
may be used to remove blood clots within a body. For
example, FIGS. 19A-19D illustrate an example of a suction
catheter including a distal tip with a plurality of (e.g., 4)
cushioning flow openings positioned at or distal to the
midline of an aspiration opening, as shown above. The clot
material is positioned within a vessel occluding the vessel.
The distal end of the suction catheter is shown initially
positioned near the clot material, as shown in FIG. 19A.
Activating suction causes the clot material to be drawn into
the aspiration opening of the suction catheter, pulling the
clot proximally against the proximal edge of the aspiration
opening, and cutting a long strip of material, as shown in
FIG. 19B. The cushioning flow openings deliver a flow that
imparts a rotational force on the clot material, causing the
clot material to flip (in FIG. 19C) and continue to be driven
against the proximal edge of the aspiration opening (FIG.
19D), until the clot material is removed. In smaller-diameter
vessels, in which there is not room for the clot to flip or roll
along the distal-to-proximal axis, the combination of the
rotational force from the flow through the cushioning flow
openings and aspiration from the aspiration opening moved
the clot in a manner similar to a carriage of a typewriter;
initially pulled proximally and drive against the proximal
edge of the aspiration opening (to cut), and then returned in
the distal direction and again pulled proximally to allow
further cutting. In this example the clot was approximately
10 g (75 cc) and the collateral flow was about 25 cc/second.

Figure 20A:
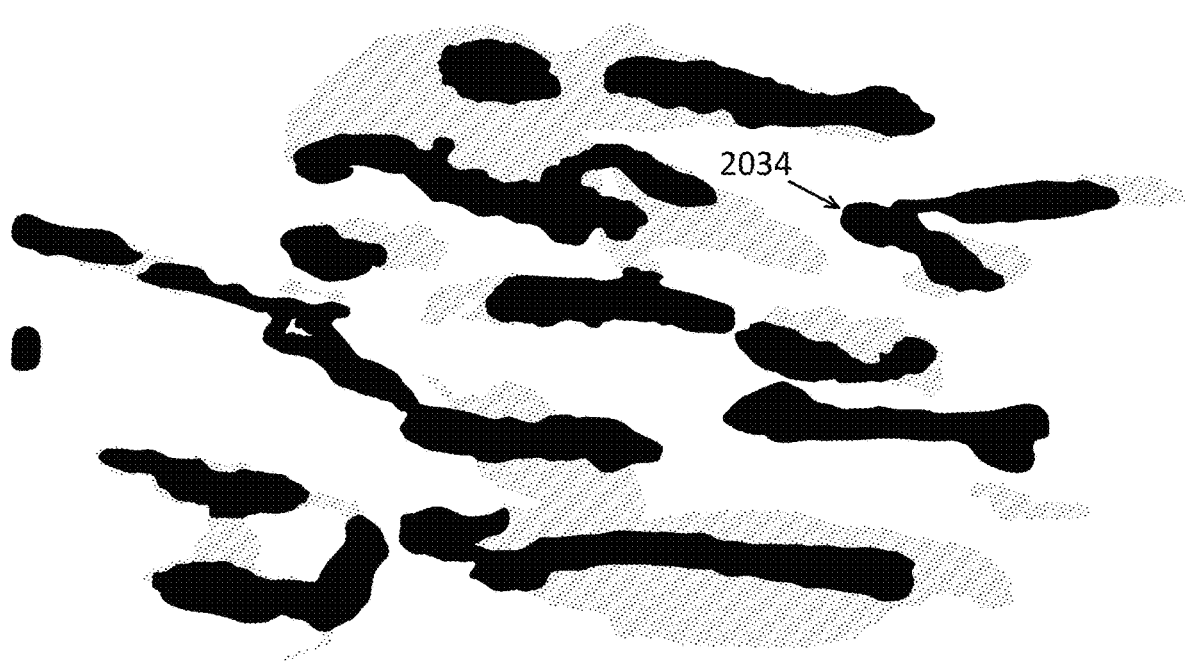
FIG. 20A illustrates examples of strips of clot collected as described herein using a suction catheter having cushioning flow openings.
Figure 20B:
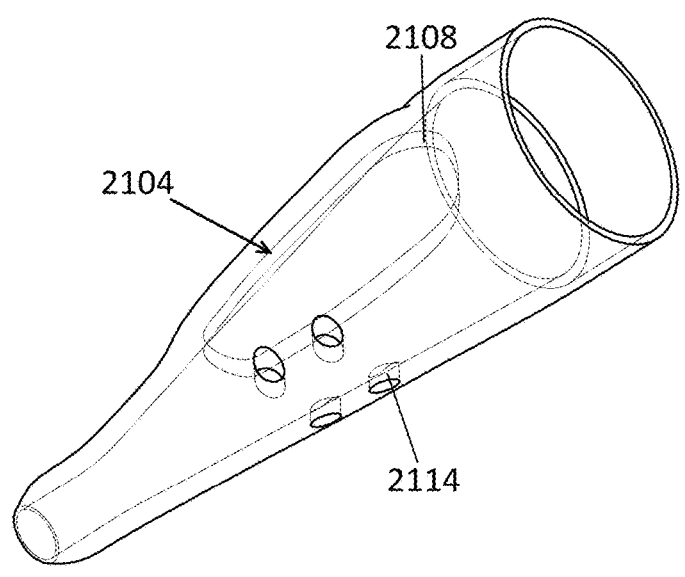
FIG. 20B schematically illustrates a distal end region of a suction catheter similar to that used to collect the strips of clot shown in FIG. 20A.

In general, the suction catheters described herein having
tips (distal end regions) similar to those described above,
such as the tip shown in FIG. 20B, including a tapered side
having an aspiration opening 2104 into an aspiration lumen
and between 2-4 cushioning flow openings 2114, clot mate-
rial was removed in long strips by driving the clot material
being removed against the proximal edge 2108. FIG. 20A
illustrates examples of strips of clot materials removed using
a tip similar to that shown in FIG. 20B. The clot material
2034 was not significantly fragmented but was removed in
long strips.

Any of the apparatuses and methods described herein may
include cushioning flow opening in which the outlet of the
cushioning flow opening is separated from the inlet of the cushioning flow opening by a longitudinal distance rather
than, as shown above, openings in which the inlet to the
opening and the outlet to the opening are both within the tip
region of the apparatus (and in some examples the inlet may
be directly opposite from the outlet of the cushioning flow
opening).

For example, FIGS. 21A-21B illustrate tips for appara-
tuses as described herein in which the cushioning flow
opening have outlets positioned as described herein, in
which the cushioning flow opening (outlet) is opposite the
aspiration opening so that at least one of the cushioning flow
opening outlets 2184 extends distally beyond the midline of
the aspiration opening. The inlet may be open to a lumen
2188 that may connect to a fluid source, as shown in FIG.
21C, to provide a cushioning flow. In FIG. 21C an external
cushioning flow fluid 2189 is provided through an inlet to
the cushioning flow opening outlets. The apparatus may
otherwise be the same as those described herein. Flow
through the cushioning flow outlets may be coordinated with
the application of aspiration (e.g., they may be on at the
same time, or the cushioning flow may be applied after the
start of aspiration).

Figure 21D:
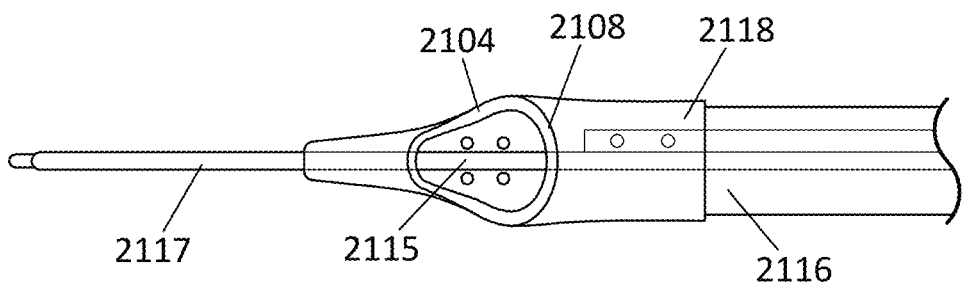
FIGS. 21D and 21E show top and bottom views, respectively, of one example of a cushioning flow apparatus as described herein.
Figure 21E:
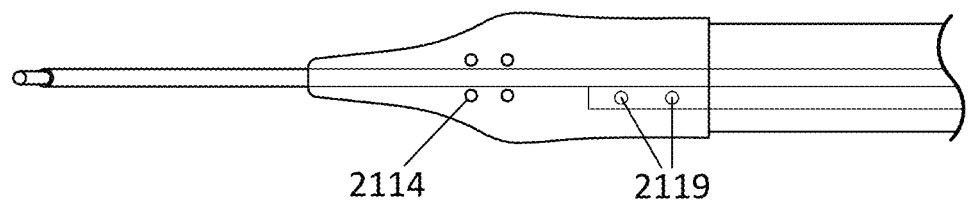
Figure 21F:
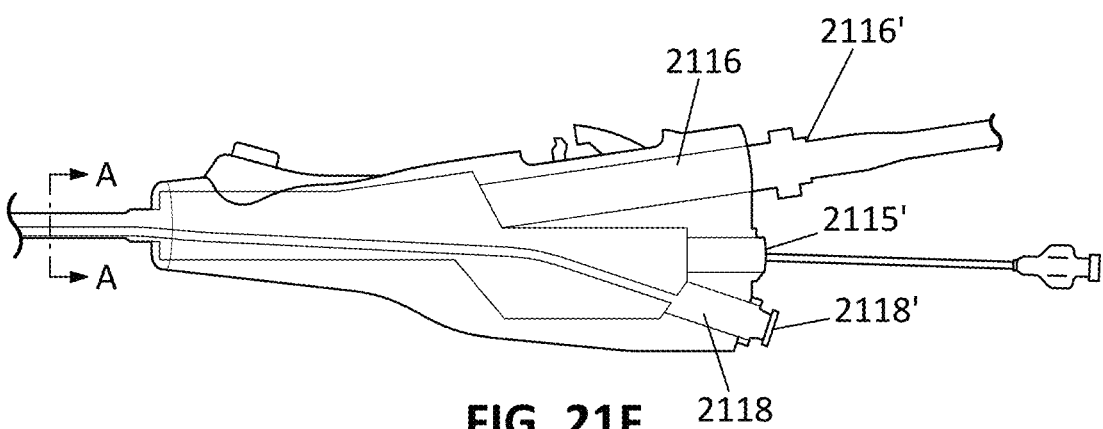
FIG. 21F shows an example of a proximal end (e.g., handle) region of an apparatus such as the cushioning flow suction catheter apparatus of FIGS. 21D-21E.
Figure 21G:
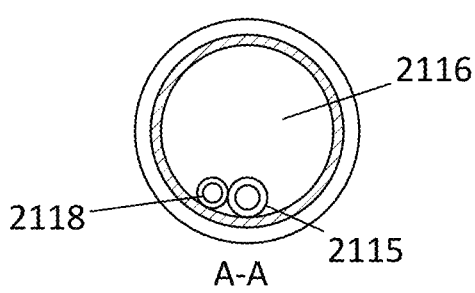
FIG. 21G shows a section through a proximal portion of the suction catheter of FIG. 21F (taken through line A-A in FIG. 21F).
Figure 21H:
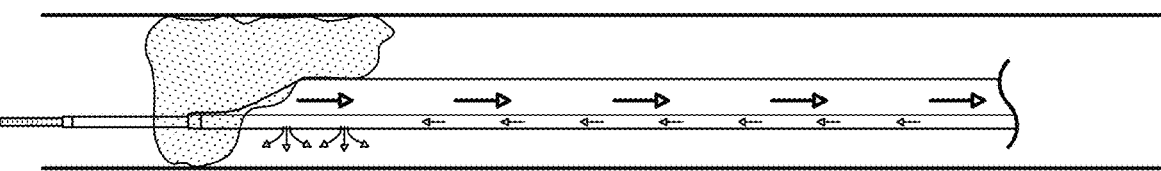
FIG. 21H is a side view of an illustration of a distal region of a suction catheter similar to that shown in FIGS. 21D-21G in contact with a clot material.
Figure 21I:
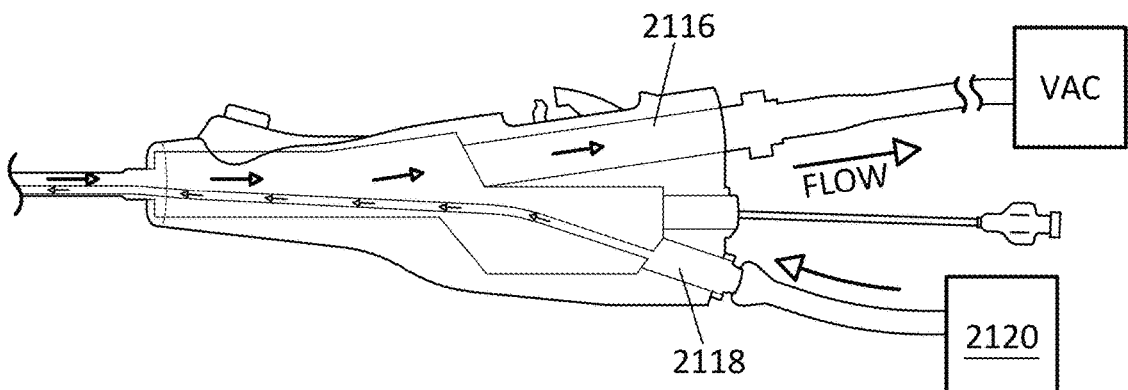
FIG. 21I schematically illustrates the operation of a handle region of the suction catheter of FIG. 21H.

FIG. 21D-I illustrates another suction catheter as
described herein that provides external fluid to the area near
the cushioning flow openings on the aspiration tip so that the
fluid can be pulled into the cushioning flow openings, and
aspirated back through the aspiration lumen of the aspiration
catheter, causing lifting of the clot upwards toward the
proximal edge of the aspiration opening as the clot passes
through the opening. The infusion of external fluid could be
useful in areas within the body that have limited fluid within
the vessel such as a peripheral vein where the in-flow has
been reduced due to proximal clot. FIGS. 21D and 21E show
top and bottom views of the distal end of the catheter having
an aspiration opening 2104 positioned on the tapered side of
the distal end of the suction catheter. Four cushioning flow
openings 2114 are positioned around the longitudinal mid-
line of the aspiration opening 2104 on the opposing side of
the catheter from the aspiration opening. A navigation lumen
2115 is positioned between the cushioning flow openings
2114 and runs parallel to the longitudinal axis of the aspi-
ration lumen. The navigation lumen 2115 in this embodi-
ment is a reinforced flexible lumen affixed to the inner wall
of the aspiration lumen 2116 of the suction catheter. The
navigation lumen 2115 is configured to accommodate a
navigation catheter 2117 that is compatible with a 0.035"
guidewire. The positioning of the navigation lumen 2115
aids in tracking of the suction catheter and serves a shield to
reduce the chances of the clot coming into the aspiration
opening 2104 and blocking the cushioning flow openings
2114. An infusion lumen 2115 is positioned next to the
navigation lumen 2115 in FIGS. 21D-21E. The infusion
lumen 2118 may also be affixed to the inner wall of the
aspiration lumen 2116. It should be understood that this
lumen could also be attached to the exterior wall of the
catheter body. The infusion lumen 2118 could also be
constructed of a flexible lay-flat tubing so that when not in
use the lumen would lay relatively flat against the wall
having minimal impact to the profile or area within the
aspiration lumen 2116. In FIGS. 21D-21E the infusion
lumen 2118 is constructed of a flexible reinforced polymeric
tube. The distal end of the infusion lumen 2118 is positioned
just proximal to the proximal edge 2108 of the aspiration
opening 2104. The distal end of the infusion lumen is
plugged and at least one infusion distal opening 2119 opens
through the side wall of the infusion lumen 2118 and
aspiration lumen 2116 so that the infusion lumen is in fluid communication with the vessel. FIG. 21F illustrates the proximal handle of the suction catheter. Within the handle, the aspiration lumen 2116 is routed to the aspiration port 2116' and the infusion lumen 2118 is routed to the infusion port 2118'. The infusion lumen port 2118' may be configured to accommodate standard syringe luer locks. Positioned between the aspiration port 2116' and the infusion port 2118' is the navigation port 2115'. FIG. 21G shows a cross-sectional view of the aspiration lumen of the suction catheter illustrating how the infusion lumen 2118 and the navigation lumen 2115 are positioned within the aspiration lumen 2116. FIGS. 21H and 21I illustrate how this embodiment of the invention is connected and how external fluid is injected into the vessel proximal to the cushioning flow openings 2114. The external fluid chamber 2120 is connected to the infusion port 2118'. In some embodiments, this chamber is positively pressurized. In other embodiments, the chamber is passive and when opened fluid is pulled from the chamber by the negative pressure generated by vacuum pressure being applied to the aspiration lumen 2116. The arrows shown in FIGS. 21H and 21I illustrate the flow of the external fluid.

FIG. 22 illustrates one example of a method of removing clot material as described herein using a tip including one or more cushioning flow openings. In FIG. 22, the method shown may include initially positioning the tip of the suction catheter near the clot material 2201. A navigation catheter (e.g., diagnostic catheter and/or guidewire) may be used to position the distal end region of the catheter proximate to the clot material within the lumen of the vessel, so that the aspiration opening is facing or near the clot material (and may be facing away from the nearest wall of the vessel). The catheter may be rotated eccentrically around the diagnostic catheter and/or guidewire to assist in orienting and positioning relative to the clot material and vessel wall.

Suction may be applied through the aspiration opening to draw the clot material towards the aspiration opening; concurrently flow through the one or more cushioning flow openings may apply a rotation (e.g. rotational force) to the clot material at the aspiration opening, driving it against the proximal edge of the aspiration opening 2203. The suction (aspiration) may continue while the clot material is cut into one or more strips against the proximal edge of the aspiration opening, so that the clot material is rotated and driven by the combination of flow from the aspiration opening and the cushioning flow openings 2205. This process may be continued to remove long strands of material 2207 until the clot material is removed. The catheter may be repositioned during this process or after the process. The aspiration may be continuously applied or may be stopped periodically to remove clot material from a collection chamber, as described in detail below.

Cushioning Flow Region

Figure 23B:
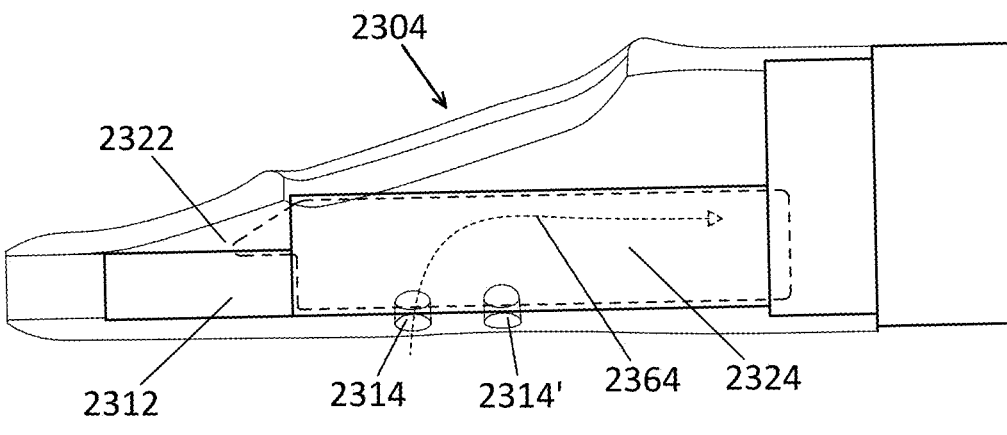
FIG. 23B shows a side view of the distal end region of an example of a suction catheter including cushioning flow openings that maintain a region of cushioning flow below the aspiration opening.

In any of the examples described herein the operation of the aspiration catheter to remove clot material, and particularly large clots, by rolling and peeling the clot (as opposed to fragmenting the clot) may benefit by maintaining a region of cushioning flow in the portion of the aspiration tip opposite from the aspiration opening. This cushioning flow region may be established by the cushioning fluid flow as described above and/or as illustrated in the following examples. FIGS. 23A and 23B illustrate a cushioning flow region 2324 that may assist in aspiration of large clots, e.g., by rolling the clot material against the proximal edge of the aspiration opening to compress and/or 'unpeel' the clot material so that it may be fed into the aspiration lumen without clogging or lollypoping. In FIG. 23A the cushioning flow region 2324 (shown as the region within the dashed outline) is along the bottom of the suction lumen (aspiration lumen) 2316 opposite from the aspiration opening 2304, and may be formed by the cushioning flow openings 2314, 2314', 2314". Fluid from the vessel (e.g., blood) may flow in 2304, 2306, 2308 through these cushioning flow openings when suction is applied through the suction lumen from the proximal end. The flow in may be somewhat deflected by the navigation lumen 2312 that passes through the suction lumen 2316. In FIG. 23A the catheter may also include a contrast lumen 2312 that may end proximal to the aspiration opening 2304.

FIG. 23B shows a side view of the distal tip region of the aspiration catheter of FIG. 23A. The region of cushioning flow 2324 is shown within the dashed region opposite from the aspiration opening 2304 (e.g., on the 'bottom' half of the suction lumen opposite from the aspiration opening. As mentioned, this region of cushioning flow may be formed by the fluid flow in thorough the distally-positioned cushioning flow openings 2314, 2314'. In the example shown in FIG. 23B the distal tip region includes four cushioning flow openings (two on either side of the longitudinal midline), on either side of the enclosed aspiration lumen 2312 that extends through the length of the device, on the 'bottom' of the suction lumen. One example of a cushioning flow 2364 is illustrated in FIG. 23B. In this example the distal end of the suction lumen at the distal tip is enclosed, forming an eddy chamber 2322. The eddy chamber may be equivalently referred to herein as a holdup region.

In any of the apparatuses and methods described herein, the location and size of the cushioning flow openings may help establish the region of cushioning flow that is configured to roll the clot material against the proximal end of the aspiration opening, preventing fragmenting of the clot material and enhancing capture. In general, these methods and apparatuses may compress the clot material and/or roll it against the proximal edge of the aspiration opening, without significantly eroding or breaking the clot material and without clogging. Thus, this technique for extracting and elongating the clot may minimize the potential for emboli. Instead these methods and apparatuses cut long strips of clot material and/or change the shape of the clot material to assume long strips without significantly fragmenting the clot material, as discussed above.

In FIGS. 23A-23B the region of cushioning flow may result from the relative arrangement of the cushioning flow openings and the aspiration opening. In any of these methods and apparatuses, it may be beneficial that the ratio of cushioning flow opening (total cushioning flow opening) to aspiration opening is between about 5% and about 10% (e.g., between about 6% and 9%, between about 7% and 8%, etc.). The ratio of the cushioning flow openings to the aspiration lumen cross-section may be, e.g., between about 5% and about 15% (e.g., between about 8% and 13%, between about 10% and 12%, etc.). Each individual cushioning flow opening may be about 1-3% of the size of the cross-section of the aspiration lumen (e.g., about 2%). As discussed and illustrated above, the offset position of the cushioning flow openings relative to the aspiration opening may also be particularly beneficial.

Figure 24A:
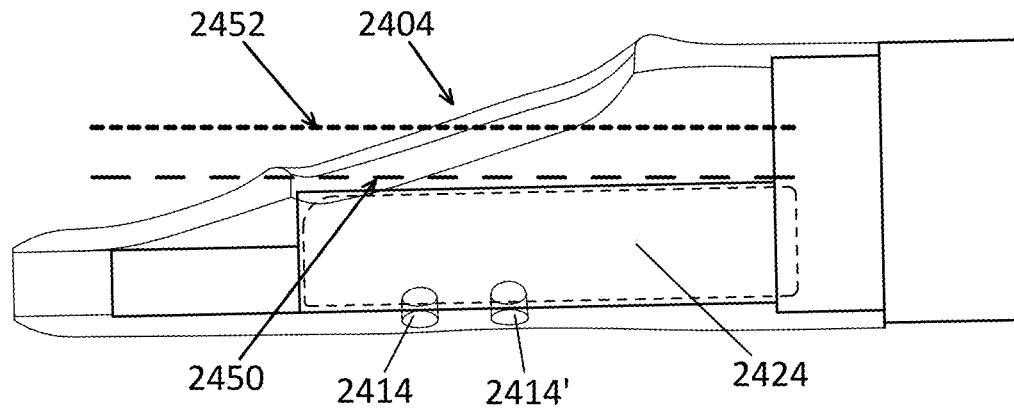
FIG. 24A shows a side view of the distal end region of an example of a suction catheter including cushioning flow openings, illustrating the offset of the aspiration opening relative to a midline of the internal lumen of the catheter shaft.

In any of the apparatuses described herein the position of the aspiration lumen relative to the long axis of the catheter (and in particular, relative to the aspiration lumen) may significantly enhance the cushioning flow effect described herein. For example, any of these apparatuses may include an aspiration orifice 2404 that may generally be positioned on a tapered lateral side of the catheter, as shown in FIG. 24A so that the distal-most edge of the aspiration opening does not cross the longitudinal midline 2450 of the aspiration lumen. FIG. 24A illustrates the positioning of the orifice center line 2452, which is the line passing through the longitudinal center of the aspiration orifice 2404 and running parallel to the long axis of the midline of the aspiration lumen 2450. In some examples, the distal-most and edge of the aspiration opening is on the tapered side of the suction lumen, but the aspiration opening does not extend further than about halfway (e.g., between 40% and 60% of the transverse diameter of the suction lumen. Offsetting the aspiration orifice may bias the clot entrainment toward to the side of the shaft (aspiration catheter) that is opposite of the cushioning flow openings. The region of cushioning flow 2424 may extend from the more distal region towards the more proximal direction, with the direction of flow being at an angle (e.g., between about 90 and 160 degrees, between about 100 and about 150 degrees, etc., relative to the direction of the clot into the aspiration opening). This may allow the cushioning flow openings 2414, 2414' to increase their flowrate as the aspiration orifice begins to get occluded by the clot, helping to prevent clogging and imparting a rotational force on clot to rotate it against the proximal edge of the aspiration opening. The distal edge of the aspiration opening may be at or just above the midline of the aspiration lumen 2450. This configuration also may prevent blocking or lollypoping of clot material.

FIGS. 24B1-24B2, 24C1-24C2 and 24D1-24D2 illustrate examples of apparatuses in which the aspiration orifice extends on a tapered side of the suction catheter so that the diameter of the suction lumen measured at the distal edge of the aspiration opening 2404 extends at least 40% (e.g., 45%, 50%, 55%, 60%, etc.) of the diameter of the suction lumen measured at the proximal edge of the aspiration opening. FIG. 24B1 shows a side view of a device having an aspiration opening 2404 that extends about 40% of the diameter of the suction lumen; the diameter of the suction lumen measured at the distal edge of the aspiration opening 2404 extends 60% of the diameter of the suction lumen measured at the proximal edge of the aspiration opening. In FIG. 24B1 the longitudinal midline 2450 is shown as a dashed line, while a line 2455 extending from the distal edge of the aspiration opening is shown as a solid line. FIG. 24B1 also shows the distance between the midline and the distal edge 2444, and the radial distance 2446 from the proximal edge of the aspiration to the distal edge of the aspiration opening, which is approximately 40% of the diameter of the suction lumen. FIG. 24B2 shows a distal end view of the apparatus of FIG. 24B1, showing the aspiration opening 2404 and illustrating how far radially into the suction lumen the aspiration opening extends. The aspiration opening extends about 40% of the diameter of the suction lumen (e.g., from the top edge of the suction lumen. FIG. 24C1 is a side view of another example of a device having an aspiration opening 2404' that extends about 50% of the diameter of the suction lumen (transverse to the long axis of the suction lumen); the diameter of the suction lumen measured at the distal edge of the aspiration opening 2404' extends 50% of the diameter of the suction lumen measured at the proximal edge of the aspiration opening. In FIG. 24C1 the longitudinal midline 2450 of the suction lumen is shown as a dashed line which is concurrent with a line 2444' extending from the distalmost edge of the aspiration opening (shown as a solid line). FIG. 24C1 also shows the distance between the midline and the distal edge 2455', and the radial distance 2446' from the proximal edge of the aspiration to the distal edge of the aspiration opening, which is approximately 50% of the diameter of the suction lumen. FIG. 24C2 shows a distal end view of the apparatus of FIG. 24C1, showing the aspiration opening 2404' and illustrating how far radially into the suction lumen the aspiration opening extends. In this example the aspiration opening extends about 50% of the diameter of the suction lumen (e.g., from the top edge of the suction lumen. FIG. 24D1 is a side view of another example of a device having an aspiration opening 2404" that extends about 60% of the diameter of the suction lumen (transverse to the long axis of the suction lumen); the diameter of the suction lumen measured at the distal edge of the aspiration opening 2404" extends 40% of the diameter of the suction lumen measured at the proximal edge of the aspiration opening. In FIG. 24D1 the longitudinal midline 2450 of the suction lumen is shown as a dashed line which is spaced apart from a line 2444" extending from the distalmost edge of the aspiration opening (shown as a solid line). FIG. 24D1 also shows the distance between the midline and the distal edge 2455", and the radial distance 2446" from the proximal edge of the aspiration to the distal edge of the aspiration opening, which is approximately 60% of the diameter of the suction lumen. FIG. 24D2 shows a distal end view of the apparatus of FIG. 24D1, showing the aspiration opening 2404" and illustrating how far radially into the suction lumen the aspiration opening extends. In this example the aspiration opening extends about 60% of the diameter of the suction lumen (e.g., from the top edge of the suction lumen.

In practice the suction catheters described herein may work surprisingly better, e.g., to form a region of cushioning flow opposite from the aspiration opening, as described and demonstrated above, when the diameter of the suction lumen measured at the distal edge of the aspiration opening extends 40% or more (e.g., 45% or more, 50% or more, 55% or more, 60% or more, etc.) of the diameter of the suction lumen measured at the proximal edge of the aspiration opening. This configuration of the aspiration opening, and suction lumen may leave a region of the diameter of the suction lumen (opposite from the aspiration opening) that is spaced apart from flow into the suction lumen through the large aspiration opening; this spaced apart region may form the region of cushioning flow described in FIGS. 23A-23B above. Flow in this region, which may be a result of the flow into the suction lumen through the cushioning flow openings, may result in a rotational force on clot material within the aspiration opening, driving rotation and cutting of strips of clot material that may be aspirated as described herein.

Figure 25:
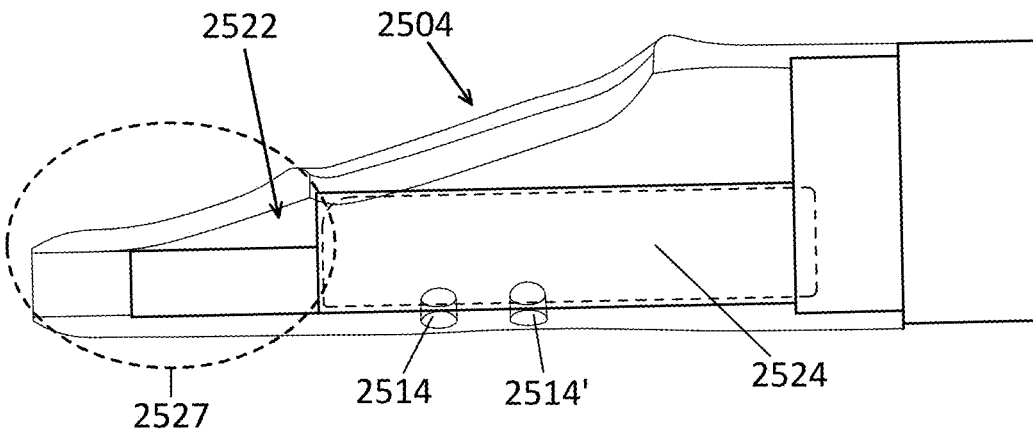
FIG. 25 shows a distal end region of an example of a suction catheter including cushioning flow openings in which the distal tip region includes an eddy current region (tip holdup region) within the region of the aspiration lumen distal to the aspiration opening.

In any of these examples the apparatus may be configured so that the distal tip region 2527 of the catheter connected to the suction lumen (aspiration lumen) is closed off, to prevent fluid (or more likely, clot material) from entering into the suction lumen and/or occluding the tip region. This may create a tip holdup region 2522, as shown in FIG. 25, which may be beneficial. In FIG. 25 the tip holdup region 2522 is a dead-end having a holdup volume. This volume may be filled with fluid (e.g., blood) and may redirect flow from the distal towards the proximal end, as part of the region of cushioning flow. For example, in FIG. 25 the distal tip region of the suction catheter is similar to that shown in FIGS. 23B and 24, including the aspiration opening 2504, and four offset cushioning flow openings 2514, 2514' (two on either side of the guide channel within the suction lumen). In this example the distal tip region 2527 creates a tip eddy current by preventing flow out of the distal end (acting as a 'dead end') that is distal to the aspiration opening 2504 and provides a flow barrier to bias the clot to the side of the shaft where the proximal edge of the aspiration opening is. This eddy current region (tip holdup region) also acts to block flow so that the flow from the cushioning flow openings 2514, 2514'. This closed distal end region may also be referred to as a shield region at the distal end of the apparatus.

Figure 26:
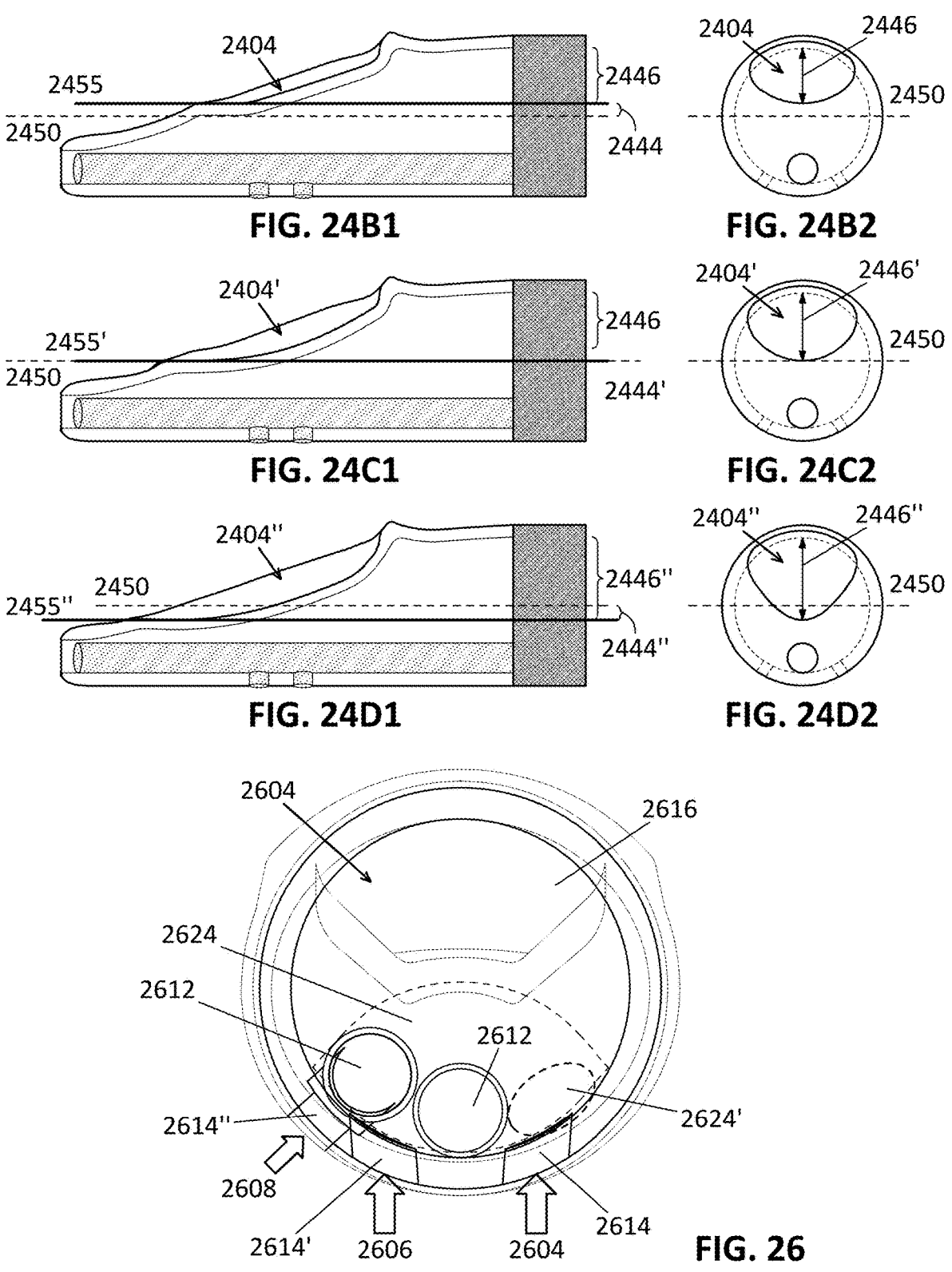
FIG. 26 shows a section through a distal end region of an example of a suction catheter transverse to the long axis, including a region within the cushioning flow region that is sheltered by the internal (e.g., navigation) lumen within the suction lumen, preventing blockage by clot material.

In any of these examples the cushioning flow openings may be protected or shielded by one or more structures within the suction lumen. The cushioning flow openings may therefore be configured so that the flow into the suction lumen forms the region of cushioning flow. For example as shown in FIGS. 23A-23B, 24 and 25, the cushioning flow openings are adjacent to and partially shielded by the navigation lumen and in some cases an additional contrast lumen. For example, FIG. 26 illustrates an example of a section through the distal end region (tip region) of an aspiration catheter such as those described herein, taken through a region transverse to the aspiration opening 2604. In FIG. 26, the section shows a pair of cushioning flow openings 2614, 2614' adjacent to (e.g., flanking on either side of) the navigation lumen 2612 that extends proximally to distally on one side of the suction lumen of the catheter. This may protect or shield 2624' the cushioning flow opening 2614 adjacent to the navigation catheter lumen. In FIG. 26 a contrast lumen 2612 also passes into this region and may shield the cushioning flow openings. Thus the cushioning flow openings are protected from being clogged or occluded by clot material drawn into the suction lumen. The flow into the cushioning flow openings may also be redirected by the navigation lumen and/or contrast lumen or other structures within the suction lumen 2616, helping form and sustain the region of cushioning flow 2624 from the flow of fluid 2604, 2606, 2608 into the cushioning flow openings.

In general, the cushioning flow openings may provide low pressure, relatively high flow opening into the suction lumen. These low pressure, high flow cushioning flow openings may cushion and redirect the clot material relative to the aspiration opening and aspiration lumen as described herein, without disruption or fragmentation of the clot material. In general the pressure applied by the cushioning flow openings is derived from (and may be proportional to) the suction applied through the suction lumen. The cushioning flow openings may be any appropriate size (as described above) and may be operated to maintain a relatively low pressure.

The suction lumen may be any appropriate diameter (e.g., about 10 F or more, 12 F or more, 14 F or more, 16 F or more, between about 6 F and 30 F, between 8 F and 28 F, between, 12 F and 28 F, etc.). In some cases the suction device may be relatively narrow and may include a suction lumen but not a separate navigation lumen (e.g., for a navigation catheter, navigation shaft, guidewire, etc.) and/or contrast lumen.

As mentioned, any of these apparatuses may be configured to apply an external fluid through one or more cushioning fluid openings. For example, saline may be provided from a proximal source of saline and applied through one or more distal cushioning fluid openings. In some cases fluid forming the region of cushioning fluid may be emitted from the internal navigation lumen and/or contrast lumen. In some examples the external fluid may be a saline solution that may be infused into the aspiration (suction) lumen. Fluid may be pumped in or may be drawn in (by the application of suction through the suction lumen, which may pull the external fluid into the suction lumen from the proximal source. As with any of these apparatus, the lumen of the apparatus (e.g., suction lumen, navigation lumen, contrast lumen, etc.) may be primed prior to start of a procedure, e.g., with saline.

Figure 27A:
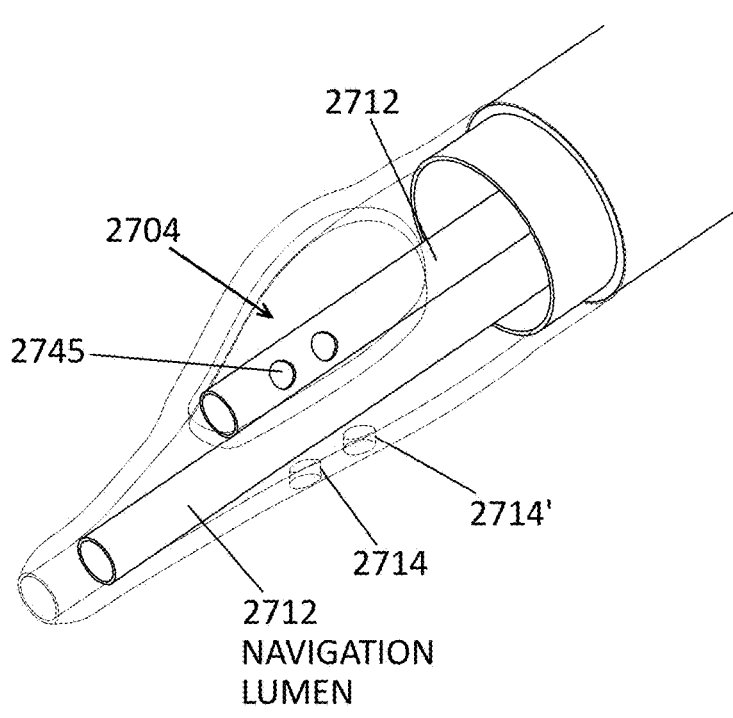
FIGS. 27A-27B illustrate examples of suction catheters as described herein configured to apply external saline in addition to (or in some examples, instead of) cushioning flow through one or more cushioning flow openings, e.g. from a proximal end of the device.
Figure 27B:
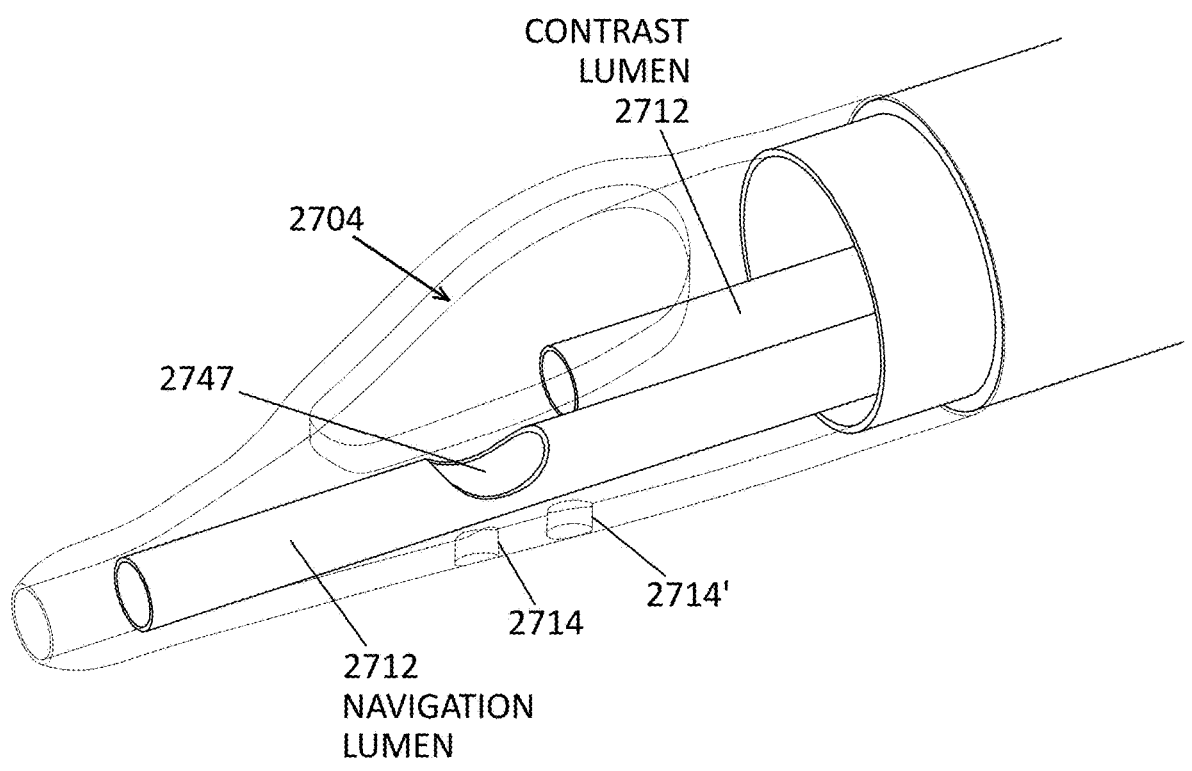

FIGS. 27A and 27B illustrate examples of the use of external fluid. In. FIG. 27A the contrast lumen 2712 includes one or more cushioning fluid openings 2745 that may apply external fluid to form the region of cushioning flow on the side of the suction lumen opposite from the aspiration opening 2704. The contrast lumen may include a tube that is affixed within the suction lumen (or a side of the suction lumen), or it may be a movable tube or member that may be laterally inserted/removed. In FIG. 27A the distal end region also includes cushioning fluid openings 2714, 2714'. Thus, as shown in FIG. 27A, the contrast lumen may be used to deliver the fluid (e.g., saline) into the continuous flow region forming the region of cushioning flow. In FIG. 27 the distal end of the suction lumen is closed off, although the navigation lumen 2712 also extend distally out of the device.

In some examples the lumen, such as the contrast lumen may be configured as a dual use lumen that may both inject contrast media external to the distal end of the apparatus (e.g., out of the aspiration opening 2704 and may also provide external fluid for providing a cushioning flow. In some examples the shaft may be rotating or rotatable so that the direction of the opening (e.g., cushioning flow opening (s) 2745) may be adjusted based on whether the contrast lumen is delivering contrast media or cushioning flow.

FIG. 27 B illustrates an example of an apparatus in which the navigation lumen 2712 may be configured for use to deliver additional cushioning flow. In FIG. 27B the aspiration catheter may include one or more lateral openings 2747. The suction catheter shown in FIG. 27B also includes four offset cushioning flow openings 2714, 2714' and a contrast lumen 2712. In use, the apparatus may apply suction from the suction lumen and out of the aspiration opening 2704, and may also apply fluid (e.g., saline) as part of a continuous flow (when applying suction) or on demand, to help prevent a clot material from blocking the aspiration opening, and/or preventing the clot material from blocking the aspiration opening.

Figure 28A:
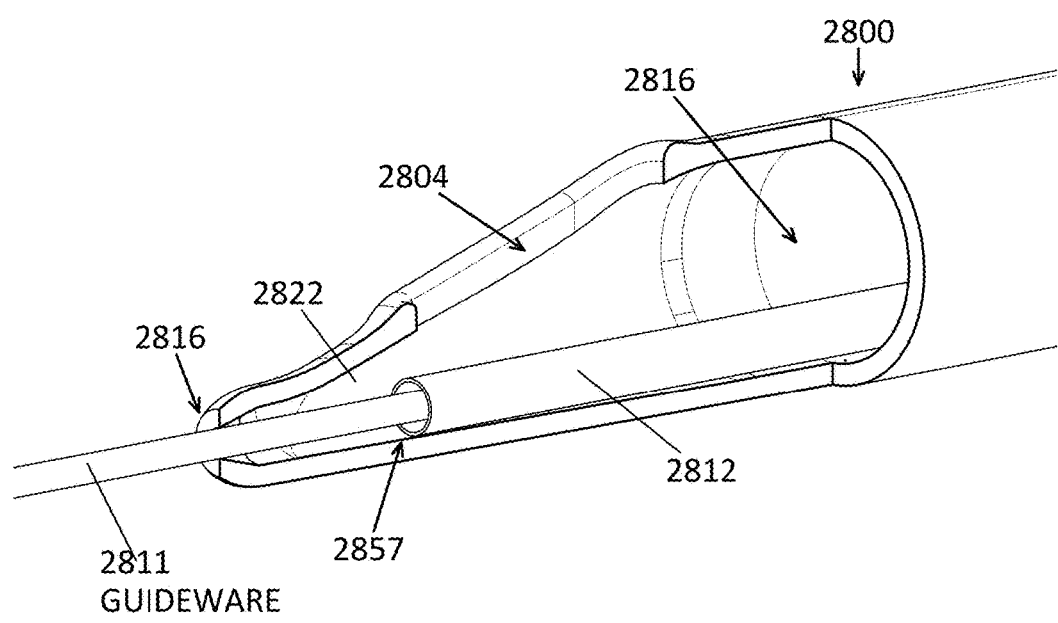
FIGS. 28A and 28B illustrate examples of suction catheters as described herein configured to apply external saline in addition to (or in some examples, instead of) cushioning flow through one or more cushioning flow openings from a distal end of a secondary lumen (e.g., navigation lumen).
Figure 28B:
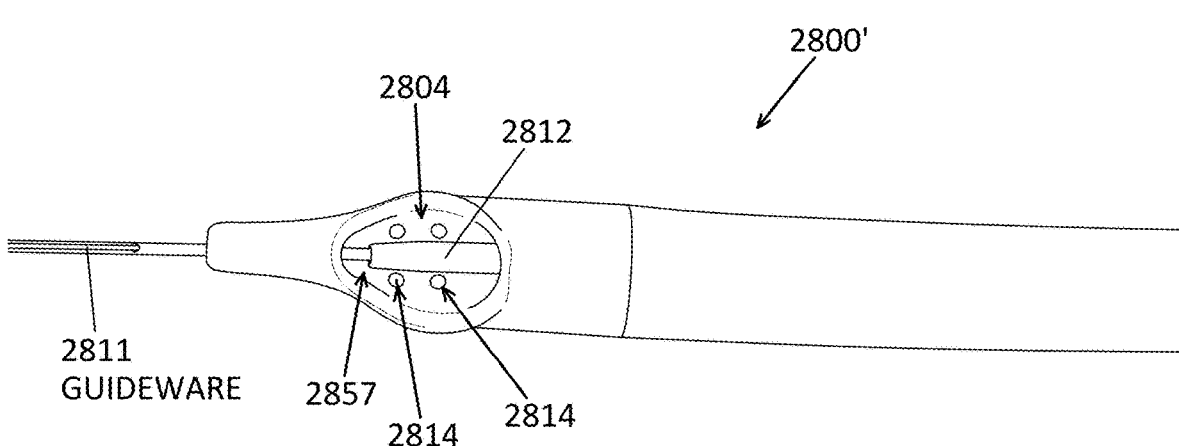

FIGS. 28A-28B illustrate another example of an apparatus configured to apply saline as part of the cushioning flow fluid. The suction lumen may apply a continuous flow of fluid from the distal end region, across at least the proximal half of the aspiration opening 2804 (and in some examples from the distal half or distal to the distal half of the aspiration opening) in order to roll and "peel" the clot material without fragmenting it, so that it may be drawn into the suction lumen even as the clot material is blocking the aspiration opening.

In FIG. 28A, the apparatus 2800 is a suction catheter that includes a suction lumen 2816 extending distally to proximally. The catheter also includes a navigation lumen, which may be referred to as a continuous flow lumen, that may be built into the shaft of the catheter, or in some examples could be insertable. This navigation lumen 2812 may also be configured to pass a guidewire 2811, as shown, or in some examples a navigation catheter (not shown). In FIG. 28A the guidewire is inserted through the navigation catheter and extends distally out of the distal opening 2816. In this example, the navigation lumen (continuous flow lumen) may terminal in the distal end region of the distal tip, prior to the distal end, so that the distal end 2857 of the navigation lumen is adjacent to the distal end region of the aspiration opening 8204, adjacent to the distal end or just distal to the distal end of the aspiration opening. For example, the opening 2857 may be positioned such that it is opposite the aspiration orifice 2804 and may end somewhere between the proximal edge of the orifice and a region just distal to the distal edge of the aspiration orifice 2804.

The distal tip (distal end opening 2816) of the device may be configured so that the guidewire may exit out of the tip, but is closed and/or sealed over the end of the guidewire, as shown. For example, the inner diameter (ID) of the tip of the apparatus 2816 may be configured to pass the guidewire (e.g., a 0.035 GW) through the device, but it may restrict fluid flow (e.g., injected saline) leaving the tip distally. Instead, fluid may leave the distal end (with or without the guidewire present) and may be redirected by the inside of the distal-tip region so that it is directed proximally and is extracted via the vacuum applied during clot removal.

In some examples the distal tip 2816 may be closed by a membrane or by a pre-set "pinch" that may allow passage of a guidewire (e.g., a 4 F catheter or guidewire) to be inserted through it but that may also restrict fluid from exiting the tip. Any of these apparatuses may also include additional cushioning flow openings (not shown in the example of FIG. 28A, but present in 28B). FIG. 28B shows another example of an aspiration catheter 2800' in which the navigation lumen 2812 is configured to pass saline as part of the cushioning flow. When suction is applied, cushioning flow may be provided through the cushioning flow openings 2814, 2814' positioned as described above. In some cases, the additional fluid may be applied through the navigation lumen on demand, e.g., in order to assist in preventing clogging of the aspiration orifice 2804 or attachment of clot material. For example, the additional saline may provide a continuous flow that may help roll and/or compress the clot material to prevent blockage of the aspiration orifice.

Figure 29:
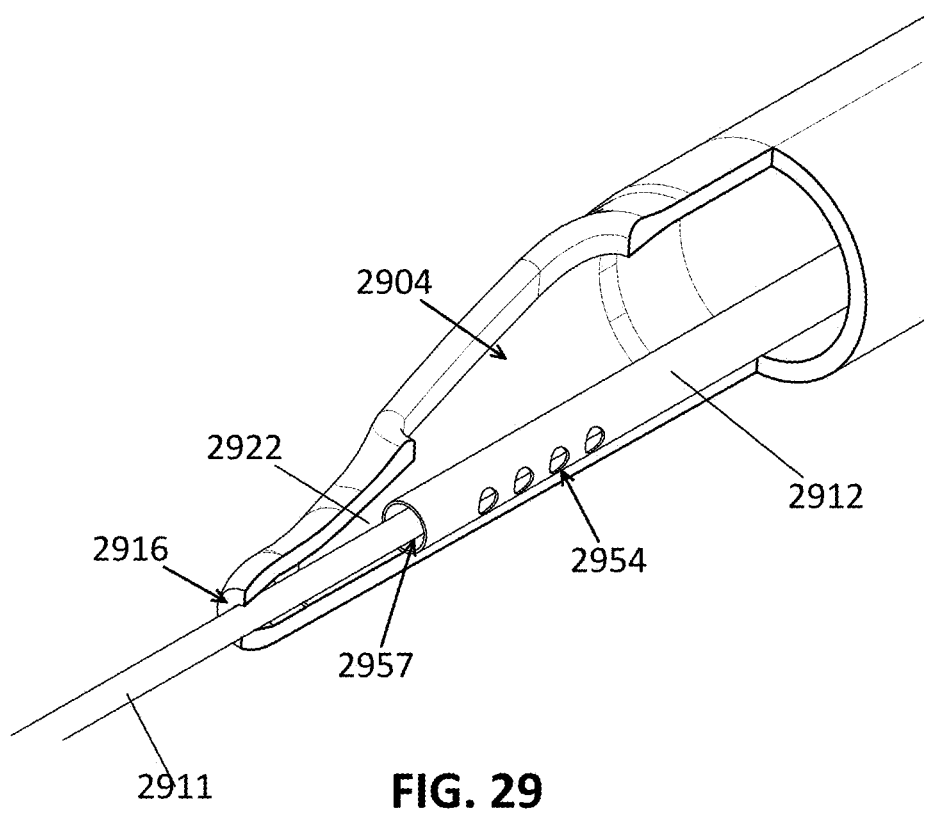
FIG. 29 shows a schematic illustration of an example of a distal end of a suction catheter configured to apply external saline in addition to (or in some examples, instead of) cushioning flow through one or more cushioning flow openings. A portion of the distal end region of the catheter in FIG. 29 is shown cut away to reveal internal detail.
Figure 30:
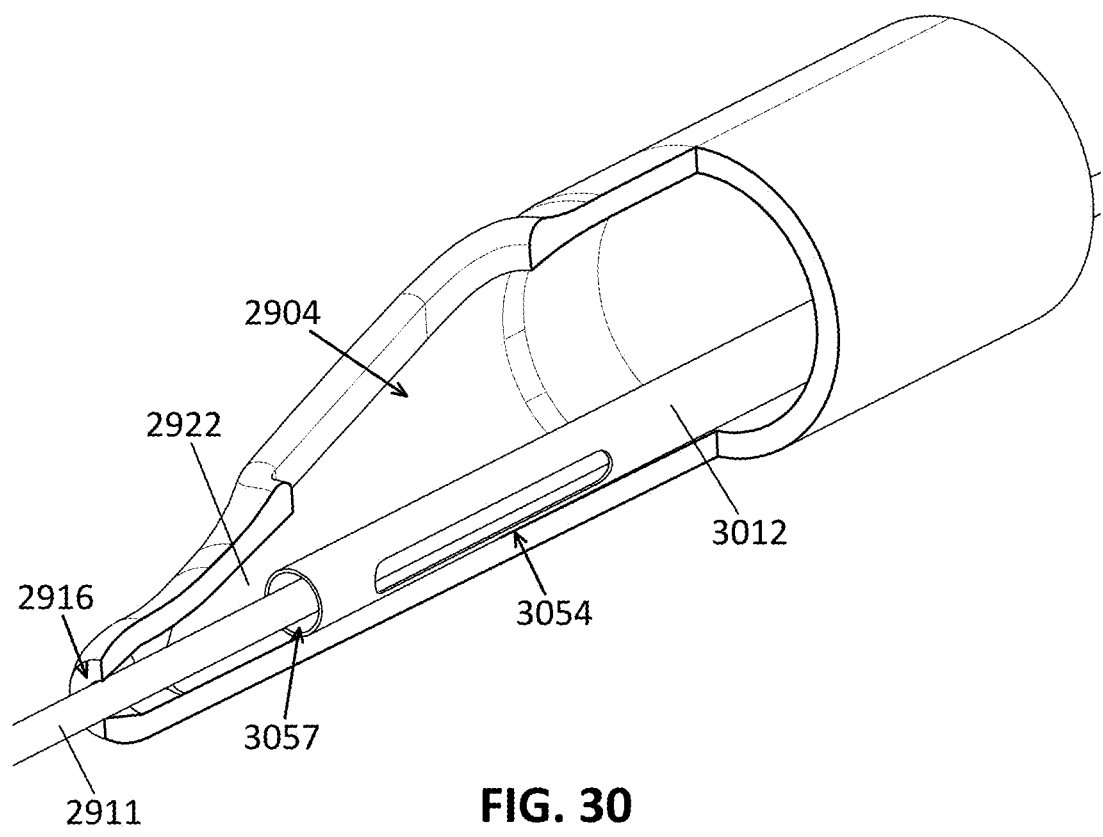
FIG. 30 schematically illustrates another example of a distal end of a suction catheter configured to apply external saline in addition to (or in some examples, instead of) cushioning flow through one or more cushioning flow openings. A portion of the distal end region of the catheter in FIG. 30 is shown cut away to reveal internal detail.

FIGS. 29 and 30 illustrate alternative examples of suction catheters that include a navigation lumen that is configured to pass saline as part of a cushioning flow into the distal end region of the catheter, similar to the example shown in FIGS. 28A and 28B. In FIG. 29 the navigation lumen 2912 extends into the distal end region of the aspiration catheter within the suction lumen so that the distal end 2957 of the navigation lumen is positioned opposite from the distal end of the aspiration aperture (aspiration opening 2904). A guidewire 2911 is shown extending from through the navigation lumen 2912 and out of the distal end tip 2916 of the aspiration catheter. As mentioned in reference to FIGS. 28A-28B, the distal end tip 2916 may be configured to close or seal to prevent fluid from passing through, yet allow passage of a guidewire and/or guide catheter (e.g., navigation catheter). In FIG. 29 the distal region of the navigation lumen 2912 may also include one or more lateral openings (e.g., configured as cushioning flow openings 2954 for passing fluid, such as saline, form out of the navigation lumen and into the suction lumen. These one or more lateral openings (in this example a plurality of small lateral openings are shown) may be oriented away from the aspiration opening 2904, to better help establish the region of cushioning flow opposite from the aspiration opening 2904. In addition, as in FIGS. 28A-28B the distal end 2957 of the navigation lumen may also be open and may pass fluid when suction is applied in the suction lumen and/or when fluid is driven (by applying positive pressure) from the proximal end of the navigation lumen into the enclosed distal region 2922 and redirect the flow proximally. In general the one or more cushioning flow openings 2954 (e.g., ports) on the navigation lumen may be configured positioned across from the distal end region of the aspiration opening, as may be generally true for the cushioning flow openings so that they may from a region of cushioning flow that extends along the long axis of suction lumen to drive the clot to rotate against the proximal edge region of the aspiration opening.

FIG. 30 is similar to the example shown in FIG. 29, including a navigation lumen 3012 with a distal end opening 3507 positioned distal to or opposite from the distal end region of the aspiration opening 2904. However in FIG. 30 the lateral opening through the navigation catheter form one or more elongate cushioning flow openings 3054. As in FIG. 29, the suction catheter shown in FIG. 30 may be used with or without a guidewire present in the navigation lumen. In general the cushioning flow opening(s) through the navigation lumen into the suction lumen may have a variety of different shapes and dimensions to allow fluid (e.g., saline) emitted from the navigation lumen to be dispersed at the distal tip region of the catheter opposite where the clot enters the aspiration opening.

Figure 31:
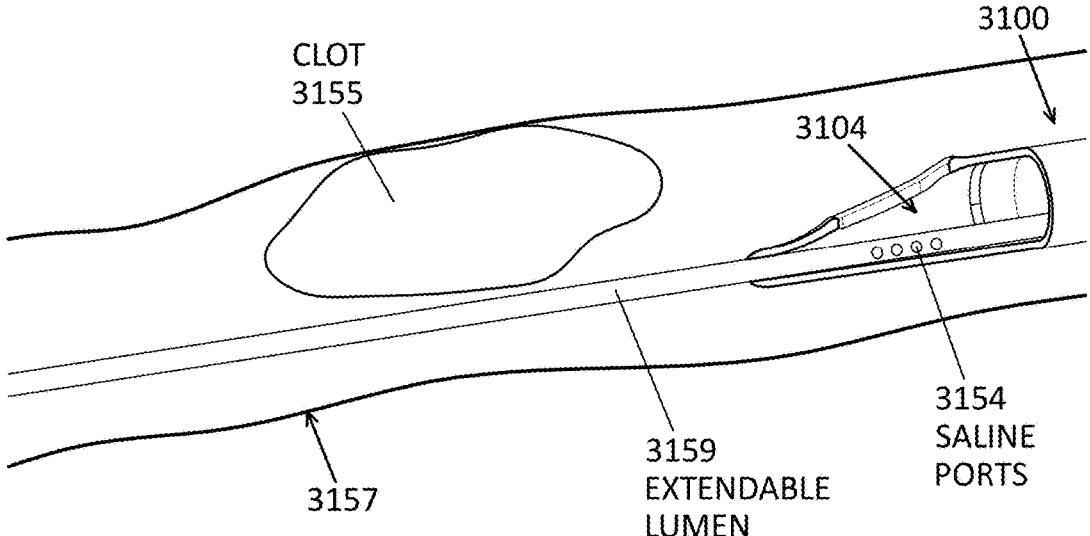
FIG. 31 illustrates another example of a suction catheter configured to apply external fluid (in this example). The fluid may be blood from a region of the vessel distal to the clot into the aspiration tip of the aspiration catheter using an extendable lumen.

FIG. 31 illustrates another example of a suction catheter in which the apparatus is configured so that fluid may be drawn into the suction lumen through an internal lumen (e.g., similar to the navigation lumen) from a region that is distal to the catheter, such as distal to the clot. In this example the suction catheter 3100 includes an extendable lumen 3159 that may be extended distally out of the distal tip of the suction catheter. The extendable lumen may draw fluid from outside of the catheter, e.g., distal to the clot, into the suction lumen and out of the ports 3154 (e.g., one or more cushioning flow openings) on the lateral side of the extendable lumen 3159. In some examples the region of the extendable lumen proximal to these ports may be closed so that suction through the suction lumen may draw fluid from within the extendable lumen (and from the region within the vessel 3157 distal to the clot) into the suction lumen to form the region of cushioning flow adjacent to the aspiration opening 3104. The extendable lumen may be advanced distally out of the aspiration catheter when the aspiration catheter is near the clot 3155 so that the lateral cushioning flow openings are positioned adjacent to (or just distal to) the distal end of the aspiration opening. Thus, in this example the lumen can be dynamically advanced distal to a blood clot 3155 and can pull blood from the distal part of the vessel 3157 into the aspiration tip in order to provide the fluid needed to keep the clot moving and the catheter flowing during aspiration. As mentioned, the extendable lumen is closed the proximal end to ensure fluid is pulled from its distal opening.

Suction Chamber

In addition to the catheter devices described herein, also described are blood collection (aspiration) apparatuses that are configured for reperfusion of the collected blood. Catheters and instruments for the removal of thrombus from the vascular system may include elongated aspiration catheters such as those described above. Suction can be applied through the catheters to aspirate thrombus from a target site in the vasculature, through a lumen of the device, and out of the body, where it may be collected. In some cases the aspiration/suction is provided by pulling an attached syringe into vacuum. In other configurations aspiration/suction is applied from a suction pump that is attached to the catheter.

Described herein are blood collection chamber apparatuses (devices, system, etc., including blood collection devices) in which aspirated thrombus material and fluid blood can be collected for examination and measurement. In particular, these apparatuses may be configured to enable efficient and safe reperfusion of collected (and filtered) blood. In some configurations a suction pump is connected to the blood collection chamber which is then connected to the catheter. The collection chamber may include a valve or may be coupled in-line with the apparatus to selectively open a fluid path from the catheter to the chamber to allow for the application of the aspiration/suction directly from the catheter (e.g., the aspiration catheter). The blood collection chambers described herein may alternatively be referred to as a vacuum chamber, a vacuum accumulator, a vacuum box, or a vacuum reservoir.

The blood collection chamber may be configured to allow direct visualization of the collected clot and/or blood. For example, all or a portion of the blood collection chamber may be formed of a clear (transparent or at least translucent) material, so that collected blood and/or thrombus can be visualized. Any of these apparatuses may be calibrated for indicating volume of the blood and/or thrombus collected. For example, the apparatus may include graduations (e.g., markings) to allow the measurement of volume of aspirated materials. Any of these apparatuses may include one or more filters (e.g., a coarse filter and/or a fine filter) to separate fluid blood from the solid-semi-solid thrombus collected. The filter(s) may be removable, particularly the coarse filter, so the filtered thrombus can be removed, washed (e.g., flushed with saline), measured, photographed, and/or physically inspected by the physician or used for further testing.

In general, these apparatuses may be configured to be sized for collecting and holding a volume that is manageable in the surgical field, on the bed rail, or IV pole. Additionally these apparatuses may have a volume that is small enough to allow rapid (e.g., under one minute) reaching of internal vacuum by the suction pump. These apparatuses may have a volume that is sufficiently large so as to provide enough vacuum accumulation that applications of aspiration/suction in bursts of 5 seconds does not reduce the chamber vacuum by more than 50% or less. These apparatuses may be sized appropriately so as to not allow too much aspiration (at the risk of exsanguinating the patient). For example, these apparatuses may be configured to limit the blood removal to 500 cc of blood or less. In some examples the blood collection chamber may be approximately 500 cc.

Further, the blood collection apparatuses described herein may be configured to allow for the reperfusion of the collected fluid blood. Although this may simply be an openable lid that allows collected fluid to be removed with a syringe and fine filter, more particularly, the apparatuses described herein may be adapted to filter and treat the blood so that it may be immediately and easily used within the operating theater near the patient (or directly coupled to the patient) quickly and in a manner that prevents foaming and/or disturbing of the blood. In some examples the filtered blood may be configured to be withdrawn from a bottom sidewall via a needless syringe valve. This may allow the fluid blood to be withdrawn from the blood collection apparatus by a syringe for reperfusion to the patient through a blood return circuit place in the vasculature. In some cases the blood return circuit may be directly coupled to the apparatus.

Any of these apparatuses may be lighted for enhanced visualization of the blood and/or removed clot. Any of these apparatuses may include a separate clot collection chamber that is in-line with the apparatus. The apparatus, and in particular the clot collection portion (which may include the coarse filter) may be configured to measure the weight and/or volume of the collected clot material.

Any of these apparatuses may be heated and/or cooled. In particular, the region of the apparatus configured for collecting blood may be temperature-regulated. As will be described in detail below, the apparatus may generally include an upper chamber configured to be charged with the vacuum and connected in-line with the aspiration catheter, that is fluidly connected to a lower blood collection region that is configured to be in communication with the reperfusion portion. Blood may generally be configured to be transferred between the upper chamber (upper canister or vacuum chamber) and the lower chamber (lower canister or blood collection chamber) by gravity. In some examples the upper and lower chambers may be formed of the same (or a different) canister and may be separated by one or more a passive or active valves that maintain the negative pressure (e.g., vacuum) in the upper chamber and only pass the blood to the lower chamber once the pressure between the two chambers is normalized in a manner that prevents or limits foaming of the blood.

Any of these blood collection apparatuses may be configured to allow the introduction of a medication, such as, for example, heparin. Any of these apparatuses may be configured to allow for saline flushing. In some examples the apparatus may include one or more sealable but openable lids or doors or to allow the contents to be manually emptied and/or cleaned.

In general, these apparatuses may be configured to operate safely and provide a failsafe mode in which one or more automatic or spontaneous shut off valve(s) is included so that when the blood collection chamber reaches a critical collection volume of blood collected, the aspiration through the catheter into the apparatus is stopped. This may include the use of a sensor, including a mechanical and/or electrical sensor. In some examples, the apparatus may include a float valve that blocks the aspiration outlet when contents position it in proximity of the aspiration outlet.

In general, there is an unmet need for blood collection apparatuses having vacuum chambers that permit collection and reperfusion of the blood to the patient. Currently available blood collection chambers typically collect blood in the same chamber as the vacuum. This may cause the collected blood to de-gas and foam. This also may cause some level of hemolysis. In addition, this may require a larger volume of the vacuum chamber, requiring longer to charge the chamber before and in between uses. The blood collection apparatuses described herein may be particularly useful for collecting blood into a vacuum chamber while minimizing the level of vacuum applied to the blood and/or the time the blood is held under vacuum. The blood collection apparatuses described herein may further be configured to allow storage of blood in a vacuum canister so that it may be re-perfused efficiently and with minimal damage to the blood or risk of harm to the patient.

Figure 32:
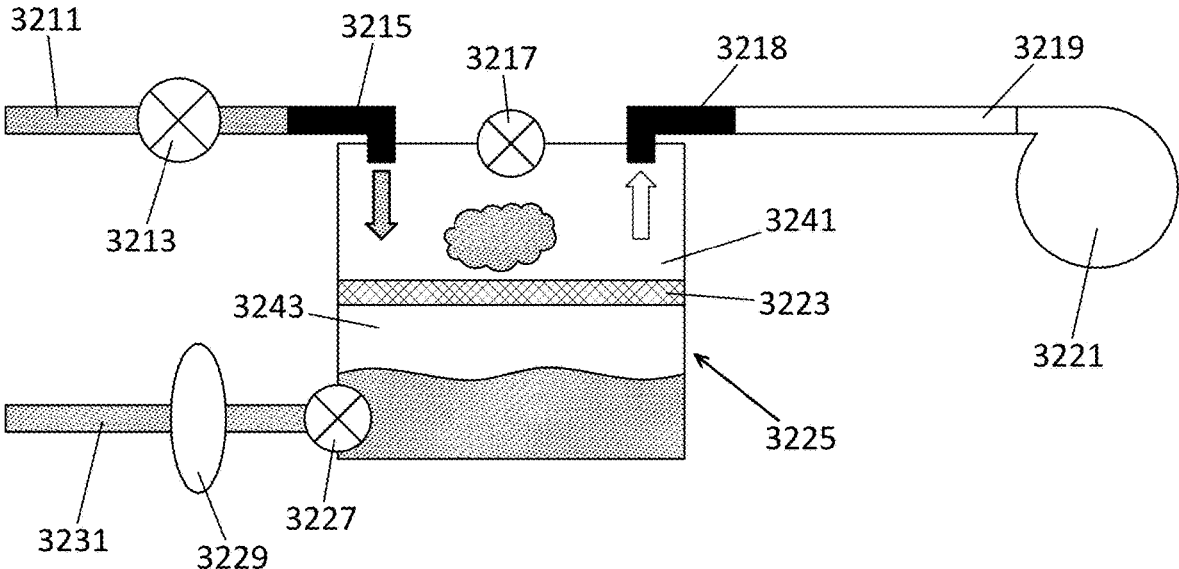
FIG. 32 schematically illustrates one example of a device for collecting and/or perfusion of blood, e.g., during a clot capture procedure.

FIG. 32 shows one example of a blood collection apparatus configured for reperfusion. In this example, the blood collection apparatus is configured for the use with thrombus aspiration catheter such as (but not limited to) the aspiration (e.g., suction) catheter described in FIGS. 1-21. In FIG. 32, the apparatus may optionally include a vacuum source (e.g., vacuum pump 3221) that may be connected to a vacuum line 3219. The vacuum line 3219 in this example connects to an outlet on the vacuum canister 3225 through a vacuum outlet 3218. The vacuum canister 3225 has a vacuum release valve 3217 (selectively opening/closing the valve to atmosphere). The canister 3225 in this example is divided into an upper chamber portion 3241 and a chamber portion 3243, that are separated by a permeable solid/liquid filter 3223 dividing it into the upper portion and a lower portion. Solids may be collected on the top portion of the filter. Fluids may pass through the filter and be collected in the bottom portion of the canister. The canister has an aspiration inlet 3215. An aspiration line 3211 connects to the aspiration inlet. There is an on/off valve 3213 on the aspiration line (or at the aspiration inlet). The aspiration line may connect to the aspiration catheter that is inserted into the vasculature and positioned at a target/therapeutic site. The apparatus also includes a reperfusion valve 3227 (which may be coupled to or form part of a reperfusion outlet) at the bottom and/or bottom sidewall on a lower half of the second (lower) chamber 3243 of the canister. The reperfusion line in communication with the fluid collection bottom portion of the canister may be coupled to a reperfusion circuit or collection/delivery container (e.g., bag, syringe, etc.). In FIG. 32, a reperfusion line 3231 is connected to the reperfusion valve 3227 (and may connect to a blood return circuit) and is also connected in-line with a fine filter 3229 that may be used to further remove blood impurities.

In some examples, as illustrated in FIGS. 33A-33E, a blood collection apparatus such as that shown in FIG. 32 may be use with a suction catheter by initially turning on the pump (vacuum source 3321) and "charging" the canister 3225 to a vacuum at the desired vacuum level (e.g., less than 1 atm) by applying negative pressure to the first chamber 3241 by pumping vacuum through the vacuum outlet 3218 in the first chamber while the on/off aspiration valve 3213 and the vacuum release valve 3217 are closed (FIG. 33B). Alternatively, the vacuum may be left on, though at a reduced level, and/or may be configured to maintain the vacuum to a predetermined level within the canister; any of these apparatuses may include a sensor to detect pressure within the upper region of the canister. The canister may initially be empty of all solids and fluids at the start of a procedure (FIG. 33A). Once charged, the pump may be turned off, holding the charged vacuum in the canister. Once the aspiration catheter is positioned at a target site in the vasculature, the aspiration valve 3313 may be opened, and fluid blood 3343 and thrombus material (clot material) 3344 may be drawn out of the vasculature through the aspiration catheter and aspiration line and into the canister (FIG. 33C). Clot material 3344 from the aspiration catheter may collect on the top of the aspiration filter (e.g., coarse filter) 3323, while fluids (e.g., blood 3343) may pass through the filter and collect in the bottom portion of the canister, as shown in FIG. 33D. At various times during the procedure, the aspiration may be reduced or turned off by closing the aspiration valve 3313. Aspiration can be repeated until the physician removes all desired thrombus or until the canister reaches its maximum fill point, or the maximum amount of fluid blood has been aspirated, or until the canister reaches its maximum holding condition, or until the "vacuum charge" in the canister depletes to a minimum level. Once the procedure is complete, and/or once it is determined to stop or pause aspiration, the aspiration valve 3313 may be closed and the blood intended for reperfusion that is now stored in the bottom of the canister under vacuum conditions may be prepared for reperfusion. For example, the vacuum release valve 3317 may be opened to reduce canister vacuum to a minimal amount or return it to a completely atmospheric condition (FIG. 33E). Thereafter, the reperfusion valve 3327 may be opened, and the collected fluid blood may be returned to the patient. The reperfusion valve 3327 may then be shut, and the solid clot material 3344 may be removed (e.g., in this example, an optional lid or door can be opened to allow for the removal of solid thrombus and or the solid/fluid filter with the thrombus). For example, the thrombus (clot material) can be flushed with saline, inspected, measured, and cleaned from the coarse filter 3323. The filter may be replaced, and the lid or door shut. The vacuum release valve 3317 may then be shut and the suction pump may again charge the vacuum in the canister, and the physician can conduct additional aspiration thrombectomy.

As mentioned, in some cases the suction pump 3321 can be left running continuously until the atmospheric valve is opened. In some cases, the atmospheric valve can be opened selectively to minimize the amount or time the fluid blood is held under vacuum conditions.

In general, it would be particularly useful to divide the vacuum canister into separate vacuum and blood collection portions. For example, the apparatus of FIGS. 32 and 33A-33E may include an additional partition after the coarse filter. This partition may divide the canister into an upper chamber or vacuum chamber and a lower chamber or blood storage chamber. The partition may include one or more one-way valves that allows fluid blood to pass through when opened so that it may pass from the vacuum chamber to the blood storage chamber. The one-way valve may be configured to be automatically (e.g., spontaneously) operated and/or may be controlled to open.

In some examples the bottom chamber (e.g., the blood storage chamber) may include a pressure regulation opening. In some examples the pressure regulation opening is a small hole or opening that is open to atmosphere. In some examples the pressure regulation opening may be a valved opening that permits control of the pressure within the lower chamber. Thus the apparatus may include one or more sensors for detecting pressure in the lower chamber. The one-way valve (which may be referred to herein as a partition valve) is typically positioned on the partition between the upper and lower chambers. In some examples the partition valve may operate automatically by allowing fluid blood to pass from the upper (vacuum) chamber above into the lower chamber via the fluid's own weight, which may cause the one-way valve to flex open. When the upper chamber (the vacuum chamber) is charged with vacuum, and the lower chamber is open to atmosphere, the one-way valve may be held closed due to the pressure difference between the bottom chamber, at atmospheric pressure, and the upper chamber, in vacuum.

For example, FIG. 34 illustrates an example of a blood collection apparatus including canister partitioning into an upper chamber 3441 for holding a vacuum and a lower chamber 3443 for holding filtered blood. As in FIG. 32, the apparatus may include or be configured to couple to a vacuum source 3421 applying vacuum to charge the upper (vacuum) chamber 3441. The vacuum source may be coupled to the upper chamber by a vacuum line 3419 through a vacuum outlet 3418 coupled to the upper chamber. The upper (e.g., vacuum) chamber may also include a vacuum release valve 3417, and may be charged with a vacuum by the vacuum source. The upper chamber may also be coupled to the aspiration line that connects to an aspiration catheter. In FIG. 34, the aspiration line may be coupled to the upper chamber by an aspiration inlet 3415 and the vacuum applied to the suction catheter may be regulated by an aspiration inlet valve 3413.

A coarse filter 3423 may be in-line with the upper chamber 3441. In the example shown in FIG. 34 the coarse filter 3423 is within the upper chamber. In some examples the coarse filter is coupled in line with the aspiration line, prior to the upper chamber. The apparatus also includes a partition 3442 separating the upper chamber from the lower chamber. In the example shown in FIG. 34, the partition includes a partition valve 3433 that is a one-way valve that may be configured to automatically open when the pressure between the upper and lower chamber is normalized and when there is blood in the upper chamber. In some examples the partition valve may be controlled open (or manually opened), e.g., by a controller that determines when there is blood in the upper chamber and may cause the normalization of the pressure in the upper and lower chambers. For example, the controller (a blood collection controller) may control opening of the vacuum release valve 3417, vacuum pump (or a vacuum pump valve, not shown in FIG. 34, between the vacuum source 3421 and the vacuum outlet 3418), and a pressure regulation opening 3445 on the lower chamber. The lower chamber may be slightly larger than the upper chamber (e.g., the upper chamber may have a volume of about 400 ml, while the lower chamber has a volume of about 500 ml, etc.)

The lower, blood collection chamber 3443 may include a pressure regulation opening 3445, as described above; in some examples the pressure regulation opening is an opening to atmosphere. The lower chamber may also fluidly connect to a reperfusion valve 3477 that connects the lower chamber to a reperfusion line 3431. A fine filter 3429 may be within the lower chamber or in-line with the lower chamber (e.g., with the reperfusion line).

For example, aspiration thrombectomy can be conducted as described above using a blood collection apparatus for reperfusion similar to the embodiment shown in FIG. 34 schematically. In this example, the upper chamber may be charged with a vacuum. Because the upper chamber may be relatively small (e.g., less than 400 cc volume, less than 350 cc volume, less than 300 cc volume, less than 250 cc volume, less than 200 cc volume, less than 150 cc, etc.) compared to the overall volume of the apparatus (including the lower chamber volume, e.g., 400 cc volume or greater, 450 cc volume or greater, 500 cc volume or greater, etc.), the vacuum chamber (upper chamber) may be charged relatively quickly. The aspiration inlet valve may be controlled to apply vacuum to the catheter coupled to the aspiration line 3411 to remove fluid and clot material. Blood may be collected and passed through the coarse filter 3423 to collect clot material 3444. In some examples, the system may periodically normalize the pressure between the upper chamber 3441 and the lower chamber 3443 to allow blood in the upper chamber to pass into the lower chamber where it may be stored. For example, the apparatus may turn off the vacuum (or prevent vacuum from being applied into the upper chamber and open the vacuum release valve 3317. The lower chamber may be maintained at atmospheric pressure. Once the pressure in the upper and lower chambers are normalized relative to teach other to be approximately the same, the partition valve 3442 may be opened and blood may pass from the upper to the lower chamber. Blood may drain out of the upper vacuum compartments of the canister and then is held in the atmospheric bottom chamber.

This configuration may be particularly advantageous as the vacuum portion of the canister can be minimized since it is not required to store a volume of fluid blood between reperfusions. The smaller vacuum chamber can be charged to vacuum faster due to its optimized volume. Blood can be stored in the lower canister at atmospheric pressure thus minimizing the time it spends under vacuum and allowing the physician to re-perfuse blood at a time they choose (e.g., blood can be removed via the reperfusion line). The blood at atmospheric pressure in the storage chamber can re-gas and defoam before reperfusion.

The one way-valve partition valve 3442 may be configured to remain shut when dividing the bottom (e.g., atmospheric) chamber from the upper (e.g., vacuum) chamber portion. With the release of some or all of the vacuum chamber negative pressure, the partition valve may spontaneously open under the fluid weight of the collected blood. For example, in one example, the one-way partition valve opens under a minimal hydrostatic pressure (e.g., the pressure that is exerted by a fluid at equilibrium at a given point within the fluid, due to the force of gravity).

The hydrostatic pressure may be minimal and under, e.g., 5 mm Hg of fluid height. In some embodiments the hydrostatic pressure to open the one-way valve, e.g., the "crack pressure", may be higher than the hydrostatic pressure needed to maintain the one-way partition valve open. This would allow more complete emptying of fluid blood. In some embodiments, the one-way partition valve is configured to open under the fluid weight of blood even with some partial vacuum is present in the vacuum canister.

Examples of various one-way valves and how they may function as partition valves is shown in the table (table 4) below. In table 4, the partition valves are umbrella valves of various diameters and with various drain hole patterns.

TABLE 4

| Config-uration # | Dia. [in] | Drain Hole Size [in] | Drain Hole Pattern | Total Drain Hole Area [in^2] | Hydrostatic "Crack" Pressure [mm H2O] | Drain rate [ml/sec] |
|---|---|---|---|---|---|---|
| 1 | 1.8 | 0.125 | 3 rings, 45 total holes | 0.55 | 10 | 56 |
| 2 | 1.4 | 0.130 | 2 rings, 25 holes | 0.31 | 2 | 59 |
| 3 | 0.8 | 0.100 | 1 ring, 10 holes | 0.08 | 1 | 23 |
| 4 | 0.8 | 0.050 | 2 rings, 34 holes | 0.07 | 3 | 22 |

In this example testing, the configuration #2 showed the best performance in crack pressure coupled with drain rate. FIGS. 35A-35B illustrate an example of an umbrella valve as described herein. In FIG. 35A, the valve is shown closed. FIG. 35B shows the valve opened, when the force pushing down on the valve (arrows) due to the weight of the blood in the upper chamber exceeds the crack pressure of the valve, the valve will open, and the blood may flow down. Note that if the pressure is not normalized (approximately equal) between the upper and lower chambers, the valve will not open.

FIG. 36A-36E illustrate the operation of a blood collection apparatus similar to that shown in FIG. 34. In this example, the apparatus includes an upper chamber 3441 and a lower chamber 3443, and the upper chamber (vacuum chamber) may initially be charged with a vacuum by turning on the pump (vacuum source 3421) and "charging" the upper chamber 3441 to a vacuum at the desired vacuum level (e.g., less than 1 atm) (FIG. 36B). Once charged, the vacuum may be turned off or alternatively the vacuum may be left on, though at a reduced level or directed (by a valve) away from the vacuum chamber. Any of these apparatuses may include a sensor to detect pressure within the upper chamber that may be used for control feedback. The upper and lower chambers may initially be empty of all solids and fluids at the start of a procedure (FIG. 36A). Once charged, the pump may be turned off, holding the charged vacuum in the upper chamber. Once the aspiration catheter is positioned at a target site in the vasculature, the aspiration valve 3413 may be opened, and fluid blood 3443 and thrombus material (clot material) 3444 may be drawn out of the vasculature through the aspiration catheter and aspiration line and into the upper chamber (FIG. 36C). Clot material 3444 from the aspiration catheter may collect on the top of the aspiration filter (e.g., coarse filter) 3423, while fluids (e.g., blood 3443) may pass through the filter and collect temporarily in the bottom of the upper chamber, as shown in FIG. 36D. At various times during the procedure, the aspiration may be reduced or turned off by closing the aspiration valve 3413 and the pressure between the upper and lower chambers can be normalized. For example, if the lower chamber includes an opening to atmosphere (e.g., a pressure regulation opening), the vacuum release valve 3417 may be opened to set both the upper and lower chambers to be approximately the same (e.g., atmospheric pressure). This may allow the partition valve 3433 to open, as shown in FIG. 36E, so that the blood in the upper chamber may drain (by gravity) into the lower chamber for storage. Once drained, the partition valve may again close, and the upper chamber may again be charged with vacuum, and the aspiration may continue. At any time thereafter, including when aspiration is being performed or applied, blood may be removed from the lower chamber via the reperfusion line 3431, e.g., by opening the reperfusion valve 3427.

The aspiration may be continued by repeating the steps above. Once the procedure is complete, and/or once it is determined to stop or pause aspiration, the vacuum release valve 3417 may be opened, and the solid clot material 3444 may be removed (e.g., in this example, an optional lid or door can be opened to allow for the removal of solid thrombus and or the solid/fluid filter with the thrombus). For example, the thrombus (clot material) can be flushed with saline, inspected, measured, and cleaned from the coarse filter 3423. The filter may be replaced, and the lid or door shut. The vacuum release valve 3417 may then be shut and the suction pump may again charge the vacuum in the canister, and the physician can conduct additional aspiration thrombectomy.

FIG. 37 shows another example of a schematic of an apparatus for collecting blood for reperfusion similar to that shown in FIG. 34. This example also includes a canister partitioned into an upper chamber 3741 and a lower chamber 3743 separated by a partition and a partition valve 3733, however in this example the coarse filter is part of a separate clot filtering (coarse filtering) chamber 3757 that is coupled in-line and upstream of the upper chamber 3741. The clot filtering chamber may be configured (e.g., in a planar configuration) to allow direct visualization of the clot material 3744 as it is strained and may connect distally to the aspiration line 3711 connecting to the suction catheter and proximally to the aspiration inlet 3715 (or inlet valve 3713) to the upper chamber 3741. The filtering chamber 3757 may be opened to allow removal of clot material from the coarse filter without disrupting the apparatus. The apparatus in FIG. 37 also includes the reperfusion valve 3727 and reperfusion line 3731 as well as the partition valve 3733 and partition 3742 between the upper and lower chambers. A vacuum source 3721 may optionally be coupled to the upper chamber through a vacuum outlet 3718. The upper chamber may also include a vacuum release valve 3717.

In use the blood collection apparatus such as those shown in FIG. 34 and FIG. 37 may be used as described above. For example, FIG. 38 schematically illustrates one method of reperfusing blood during a clot removal procedure. In this example, the upper chamber of the reperfusion system may be charged with a vacuum (e.g., to a desired negative pressure/vacuum), for example, by turning on a vacuum source, and opening a vacuum valve to couple the vacuum source to the upper chamber 3802. Once the upper chamber is charged with a vacuum, an aspiration catheter (e.g., suction catheter) may be used to remove clot material (and blood), by opening the aspiration valve between the aspiration catheter and the upper channel 3804. As clot material is removed, it may be filtered from the blood by a coarse filter that is in-line with the upper chamber or within the upper chamber 3806. At any point in this process the blood may be transferred from the upper chamber into a lower, blood storage chamber, by normalizing the pressure between the upper chamber and the lower chamber 3808. For example, the upper and lower chambers may both be normalized to atmospheric pressure, e.g., by opening a vacuum release valve in the upper chamber and a pressure regulation opening in the lower chamber (which may be constantly opened or may be opened/closed). Once the pressure is normalized, the partition valve between the two may be opened, allowing the blood to drain between the upper and lower chambers; the partition valve may then close and the upper chamber may again be charged, allowing the aspiration procedure to continue 3812, repeating the steps of aspirating then draining the blood to the lower chamber from the upper chamber. The collected blood may be kept warmed or chilled and kept at atmospheric pressure so that it may defoam; at any point it may be withdrawn through the reperfusion line and returned into the body of the patient 3810.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method. The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein. The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for removing, filtering, and reperfusing a patient's blood, said method comprising:

applying negative pressure to a first chamber and a second chamber connected in-line with an aspiration catheter having a distal end in a patient blood vessel and with a negative pressure source;

opening an aspiration valve connected between the aspiration catheter and the first chamber to allow the negative pressure to draw blood and clot into the first chamber and the second chamber so that blood flows from the first chamber to the second chamber, wherein filtered blood collects in the second chamber;

closing the aspiration valve;

venting the first chamber and the second chamber to return the pressure to atmospheric; and opening a reperfusion valve to allow the filtered blood in the second chamber to return to the patient only after the aspiration valve has been closed and the first chamber and the second chamber have been vented.

2. The method of claim 1, wherein applying negative pressure to the first chamber comprises pumping vacuum through a vacuum outlet in the first chamber while the aspiration valve and a vacuum release valve are closed.

3. The method of claim 1, wherein blood and clot are drawn into the first chamber through an aspiration inlet in the first chamber.

4. The method of claim 1, wherein venting comprises normalizing the pressures in the first and second chambers.

5. The method of claim 4, wherein normalizing the pressures in the first and second chambers comprises opening a vacuum release valve in the first chamber.

6. The method of claim 1, wherein gravity causes the blood to flow from the first chamber to the second chamber.

7. The method of claim 6, wherein the first chamber is positioned over the second chamber.

8. The method of claim 1, further wherein the reperfusion valve is located on a reperfusion outlet on a lower half of the second chamber.

9. The method of claim 1, further comprising removing a filter containing the clot.

10. The method of claim 5, wherein the vacuum release valve is in fluid communication with the first chamber.

11. The method of claim 1, wherein the reperfusion valve is opened only when the vacuum release valve is opened.

12. The method of claim 1, wherein the first chamber is separated from the second chamber by a filter.

13. The method of claim 12, further comprising opening a lid to the first chamber and removing thrombus from the filter after the vacuum has been vented.

14. The method of claim 1, wherein applying negative pressure to the first chamber and the second chamber comprises charging the first chamber with a vacuum source to a desired vacuum level and turning off the vacuum source to hold the charged vacuum in the first chamber, wherein the aspiration valve is opened after the aspiration catheter has been positioned at a target site in the patient's vasculature.

15. A method for removing, filtering, and reperfusing a patient's blood, said method comprising:

positioning a distal end of an aspiration catheter at a clot target site in the patient's vasculature;

turning on a pump to charge a chamber assembly to a desired vacuum level;

turning off the pump to hold the charged vacuum in the chamber assembly;

opening an aspiration valve connected between the aspiration catheter and the chamber assembly to allow the vacuum to draw blood and clot into the chamber assembly, wherein filtered blood collects in a lower portion of the chamber assembly;

closing the aspiration valve;

venting the chamber assembly to return the pressure to atmospheric; and opening a reperfusion valve to allow the filtered blood in the chamber assembly to return to the patient only after the aspiration valve has been closed and the chamber assembly has been vented.

16. The method of claim 15, wherein the pump pumps vacuum through a vacuum outlet in the chamber assembly while the aspiration valve and a vacuum release valve are closed.

17. The method of claim 15, wherein blood and clot are drawn into the chamber assembly through an aspiration inlet in an upper portion of chamber assembly.

18. The method of claim 17, wherein gravity causes the blood to flow from the upper portion of the chamber assembly to the lower portion of the chamber assembly.

19. The method of claim 15, wherein venting comprises opening a vacuum release valve in an upper portion of the chamber assembly.

20. The method of claim 15, wherein the chamber assembly comprises a first chamber positioned over a second chamber.

21. The method of claim 20, wherein the chamber assembly comprises a filter disposed between the first chamber and the second chamber.

22. The method of claim 21, further comprising opening the chamber assembly and removing clot material from the filter.

* * * * *